(12) United States Patent
DeJournett

(10) Patent No.: US 8,956,321 B2
(45) Date of Patent: Feb. 17, 2015

(54) COMPUTERIZED SYSTEM FOR BLOOD CHEMISTRY MONITORING

(75) Inventor: Leon DeJournett, Asheville, NC (US)

(73) Assignee: Ideal Medical Technologies Inc., Asheville, NC (US)

( * ) Notice: Subject to any disclaimer, the term of this patent is extended or adjusted under 35 U.S.C. 154(b) by 1099 days.

(21) Appl. No.: 12/713,934

(22) Filed: Feb. 26, 2010

(65) Prior Publication Data

US 2010/0217238 A1 Aug. 26, 2010

Related U.S. Application Data

(63) Continuation-in-part of application No. PCT/US2008/073959, filed on Aug. 22, 2008.

(60) Provisional application No. 60/969,582, filed on Aug. 31, 2007, provisional application No. 60/973,891, filed on Sep. 20, 2007.

(51) Int. Cl.
| | | |
|---|---|---|
| *A61M 31/00* | (2006.01) | |
| *A61B 5/145* | (2006.01) | |
| *A61B 5/1495* | (2006.01) | |
| *A61B 5/00* | (2006.01) | |
| *A61M 5/168* | (2006.01) | |
| *A61M 5/172* | (2006.01) | |
| *A61M 5/142* | (2006.01) | |

(52) U.S. Cl.
CPC ......... *A61B 5/14503* (2013.01); *A61B 5/14532* (2013.01); *A61B 5/1495* (2013.01); *A61B 5/4839* (2013.01); *A61M 5/16827* (2013.01); *A61M 5/1723* (2013.01); *A61M 2005/14208* (2013.01); *A61M 2230/201* (2013.01)
USPC ............................. 604/66; 600/316; 604/67

(58) Field of Classification Search
CPC .... A61B 5/4839; A61B 5/14532; A61B 5/00; A61M 2230/201; A61M 2205/50; A61M 5/158
USPC ........... 604/890.1, 503, 66, 67; 600/316, 365, 600/368
See application file for complete search history.

(56) References Cited

U.S. PATENT DOCUMENTS

| | | | |
|---|---|---|---|
| 4,072,146 | A | 2/1978 | Howes |
| 4,118,663 | A | 10/1978 | Barben, II |

(Continued)

FOREIGN PATENT DOCUMENTS

| | | |
|---|---|---|
| EP | 1 728 469 | 12/2006 |
| WO | 94/20602 | 9/1994 |

OTHER PUBLICATIONS

Search Report and Written Opinion of foreign counterpart Application No. PCT/US2008/073959 mailed Oct. 7, 2009.

(Continued)

*Primary Examiner* — Nicholas Lucchesi
*Assistant Examiner* — Gerald Landry, II
(74) *Attorney, Agent, or Firm* — R. Brian Johnson

(57) ABSTRACT

An apparatus and computerized method of intravenously monitoring a patient's blood chemistry transmits real time measurements to an electronically controlled closed loop system that auto-regulates blood osmolality and glucose level with medications infused through a catheter designed for such purpose. The closed loop system utilizes a glucose algorithm and an osmolality algorithm implemented in hardware and software to control the flow of dextrose, insulin and hypertonic saline to a patient in an effort to achieve better patient outcomes in instances of trauma, surgery and medical illnesses.

27 Claims, 9 Drawing Sheets

(56) References Cited

U.S. PATENT DOCUMENTS

| | | | |
|---|---|---|---|
| 4,380,237 A | | 4/1983 | Newbower |
| 4,403,984 A | | 9/1983 | Ash et al. |
| 4,526,568 A | * | 7/1985 | Clemens et al. ............. 604/4.01 |
| 4,808,931 A | | 2/1989 | Ling |
| 5,038,109 A | | 8/1991 | Goble et al. |
| 5,109,850 A | * | 5/1992 | Blanco et al. ................. 600/368 |
| 5,237,993 A | | 8/1993 | Skrabal |
| 5,474,552 A | * | 12/1995 | Palti ................................ 604/67 |
| 5,497,772 A | | 3/1996 | Schulman et al. |
| 5,531,679 A | | 7/1996 | Schulman et al. |
| 5,660,163 A | | 8/1997 | Schulman et al. |
| 5,827,192 A | | 10/1998 | Gopakumaran et al. |
| 5,842,998 A | | 12/1998 | Gopakumaran et al. |
| 6,424,847 B1 | * | 7/2002 | Mastrototaro et al. ........ 600/316 |
| 6,461,331 B1 | * | 10/2002 | Van Antwerp ................ 604/131 |
| 6,558,345 B1 | * | 5/2003 | Houben et al. .................. 604/66 |
| 6,740,072 B2 | | 5/2004 | Starkweather et al. |
| 7,204,823 B2 | * | 4/2007 | Estes et al. ...................... 604/65 |
| 7,833,157 B2 | | 11/2010 | Gottlieb et al. |
| 2003/0191376 A1 | * | 10/2003 | Samuels et al. ............... 600/309 |
| 2003/0208113 A1 | * | 11/2003 | Mault et al. ................... 600/316 |
| 2003/0235817 A1 | * | 12/2003 | Bartkowiak et al. ............. 435/5 |
| 2004/0064086 A1 | | 4/2004 | Gottlieb et al. |
| 2005/0154374 A1 | * | 7/2005 | Hunter et al. ............. 604/890.1 |
| 2005/0186245 A1 | * | 8/2005 | Hunter et al. ................. 424/423 |
| 2005/0245904 A1 | * | 11/2005 | Estes et al. ................. 604/890.1 |
| 2006/0063218 A1 | * | 3/2006 | Bartkowiak et al. ........... 435/14 |
| 2006/0107729 A1 | | 5/2006 | Sullivan et al. |
| 2007/0016127 A1 | * | 1/2007 | Staib et al. ...................... 604/66 |
| 2007/0173761 A1 | * | 7/2007 | Kanderian et al. ............ 604/131 |
| 2007/0191702 A1 | | 8/2007 | Yodfat et al. |
| 2008/0045825 A1 | * | 2/2008 | Melker et al. ................. 600/365 |
| 2008/0208026 A1 | * | 8/2008 | Noujaim et al. .............. 600/365 |
| 2009/0131861 A1 | * | 5/2009 | Braig et al. ...................... 604/66 |
| 2009/0163855 A1 | * | 6/2009 | Shin et al. ........................ 604/66 |
| 2010/0057043 A1 | * | 3/2010 | Kovatchev et al. ............ 604/504 |
| 2010/0069730 A1 | * | 3/2010 | Bergstrom et al. ........... 600/365 |
| 2011/0275904 A1 | * | 11/2011 | Lebel et al. ................... 600/300 |
| 2012/0190955 A1 | * | 7/2012 | Rao et al. ...................... 600/368 |
| 2014/0039383 A1 | * | 2/2014 | Dobbles et al. ................. 604/66 |

OTHER PUBLICATIONS

International Preliminary Report of Patentability of foreign counterpart Application No. PCT/US2008/073959 dated Mar. 2, 2010.

Office Action of European counterpart Application No. 08 798 440.7 dated Jul. 5, 2011.

Qui W, et al.; Effects of therapeutic mild hypothermia on patients with severe traumatic brain injury after craniotomy; Journal of Critical Care ; Sep. 22, 2007(3): 229-23.

Part 7.5: Postresuscitation Support, IV-85; Circulation 2005; American Heart Associate, Dec. 112 (Issue 24 Suppl).

Jeremitsky E, et al.; Harbingers of Poor Outcome the Day after Severe Brain Injury: Hypothermia, Hypoxia, and Hypoperfusion; The Journal of Trauma Injury, Infection, and Critical Care; 2003; vol. 54. No. 2; 312-319.

Gentile N, et al.; Decreased Mortality by Normalizing Blood Glucose after Acute Ischemic Stroke; Society for Academic Emergency Medicine 2006; 13, No. 2; 174-180.

Mullner M, et al.; Blood Glucose Concentration After Cardiopulmonary Resuscitation Influences Functional Neurological Recovery in Human Cardiac Arrest Survivors; Journal of Cerebral Blood Flow & Metabolism; 1997 No. 17; 430-436.

Van Den Berghe G, et al.; Intensive Insulin Therapy in Critically Ill Patients, The New England Journal of Medicine Nov. 8, 2001; vol. 345, No. 19; 1359-1367.

Krinsley; Effect of an Intensive Glucose Management Protocol on the Mortality of Critically Ill Adult Patients, Mayo Clinic Proceedings, Aug. 2004; vol. 79, No. 8; 992-1000.

Van Den Berghe, G, et al.; Intensive Insulin Therapy in the Medical ICU, The New England Journal of Medicine, Feb. 2006, vol. 354, No. 5; 449-461.

Furnary, A; Effect of Hyperglycemia and Continuous Intravenous Insulin Infusions on Outcomes of Cardiac Surgical Procedures: The Portland Diabetic Project; Endocrine Practice Mar./Apr. 2004; vol. 10, Suppl 2; 21-31.

Brunkhorst, F, et al.; Intensive Insulin Therapy and Pentastarch Resuscitation in Severe Sepsis; The New England Journal of Medicine, Jan. 10, 2008; vol. 358, No. 2; 125-139.

Bhardwaj, A, et al.; Hypertonic saline solutions in brain injury; Current Opinion in Critical Care 2004; vol. 10(2); 126-131.

Zadeh, L; Fuzzy Sets; Information and Control 1965; vol. 8: 338-353.

Van Den Berghe, G, et al.; Analysis of healthcare resource utilization with intensive insulin therapy in critically ill patients; Critical Care Medicine; 2006, vol. 34, No. 3; 612-616.

Verbrugge, L, et al.; Accuracy of a Prototype Central Venous Continuous Amperometric Glucose Sensor Following CABG; American Society of Anesthesiologists, Oct. 13-17, 2007 Conference, San Francisco, California; A1427.

Zisser, H, Accuracy of a novel intravascular fluorescent continuous glucose sensor. American Diabetes Association Meeting, Jun. 5-9, 2009, New Orleans, LA. Abstract 1-LB.

Goldberg P., Siegel M., et al. Implementation of a safe and effective insulin infusion protocol in a medical intensive care unit; Diabetes Care 2004; 27:461-467.

Beilman G., Joseph J., Practical Considerations for Glucose Control in Hospitalized Patients; Diabetes Technology & Therapeutics 2005; 7:823-830.

International Search Report of foreign counterpart application No. PCT/US2008/073959 mailed Oct. 7, 2009.

Davidson et al., "Glucommander," Diabetes Care, vol. 28, No. 10, Oct. 2005, pp. 2418-2423.

Stewart, "Refining Glucose Monitors," The Orange County Register, Jul. 12, 2007.

Endotool Glucose Management System; accessed Jan. 12, 2010 at http://www.hospira.com/products/endotoolaspx.

GlucoStabilizer; accessed Jan. 12, 2010 at http://www.glucostabilizer.net.

Glumetrics: Realizing the Benefitss of Glycemic Control; accessed Jan. 12, 2010 at http://www.glumetrics.com/index.php/product/clinical-need/.

Glumetrics: GluCath Intravascular Continuous Glucose Monitor; accessed Jan. 12, 2010 at http://.www.glumetrics.com/index.php/product/glucath/.

Lord, Osmosis, osmometry, and osmoregulation, Postgrad Medical Journal 1999, vol. 75; 67-73.

Conductivity Sensor Technical Education; accessed Apr. 10, 2007 at http://www.sensorex.com/support/education/conductivity_education.html.

Conductivity Guide accessed Apr. 10, 2007 at http://www.vl-pc.com/conductivityguide.html.

Sifrim et al., Technology Insight: the role of impedance testing for esophageal disorders; Nature Clinical Practice Gastroenterology & Hepatology, 2006, 3, 210-219—Abstract.

Physicsweb—Measuring the conductivity of blood; Nov. 13, 1998; abstract accessed at http://physicsworld.com/cws/article/news/3131.

Genain et al, Infinite dilution conductimetry of plasma and urine: correlation with osmolality; Clin Chim Acta., Aug. 15, 1978; 88(1):177-182—Abstract.

Goncalves et al., Urine Conductivity: A Simple Method for Estimating Ionic Concentration and Osmolality; Published by Univerisidade Estadual de Londrina-Brazil, JBN 2005; 27 (4).

Herrmann et al., Control of diabetes insipidus by continuous monitoring of the electrical conductivity of the urine with a simple device; Acta Neurochirurgica, Sep. 1975; vol. 32, Nos. 3-4—Summary.

David et al., Bioelectrical Impedance Monitoring in the Prevention of Intravasation Syndrome During Operative Hysteroscopy; Jun. 2006., vol. 22, No. 2 : 63-67—Abstract.

Fouke et al., Sensor for measuring surface fluid conductivity in vivo; Biomedical Engineering, IEEE Transactions on Publication Date Oct. 1988; on pp. 877-881—Abstract.

Wyatt, Blood flow and blood velocity measurement in vivo by electromagnetic induction; Medical and Biological Engineering and Computing; May 1984, vol. 22, No. 3—Abstract.

Glumetrics—A Breakthrough Technology in Glucose Sensing; accessed Nov. 19, 2009 at http://www.glumetrics.com.

* cited by examiner

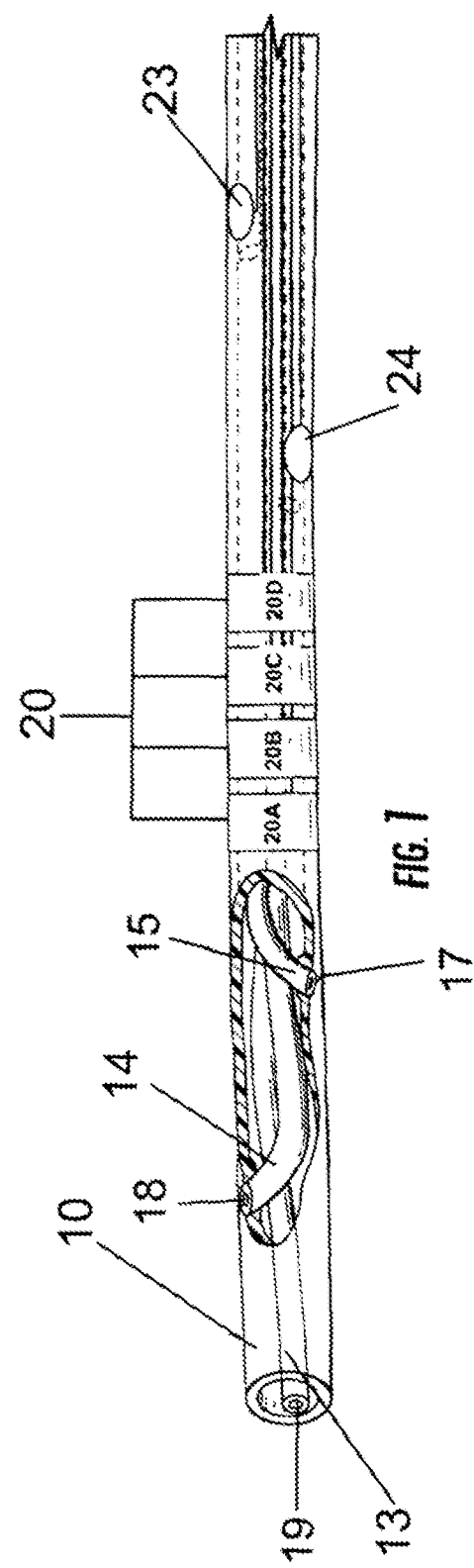

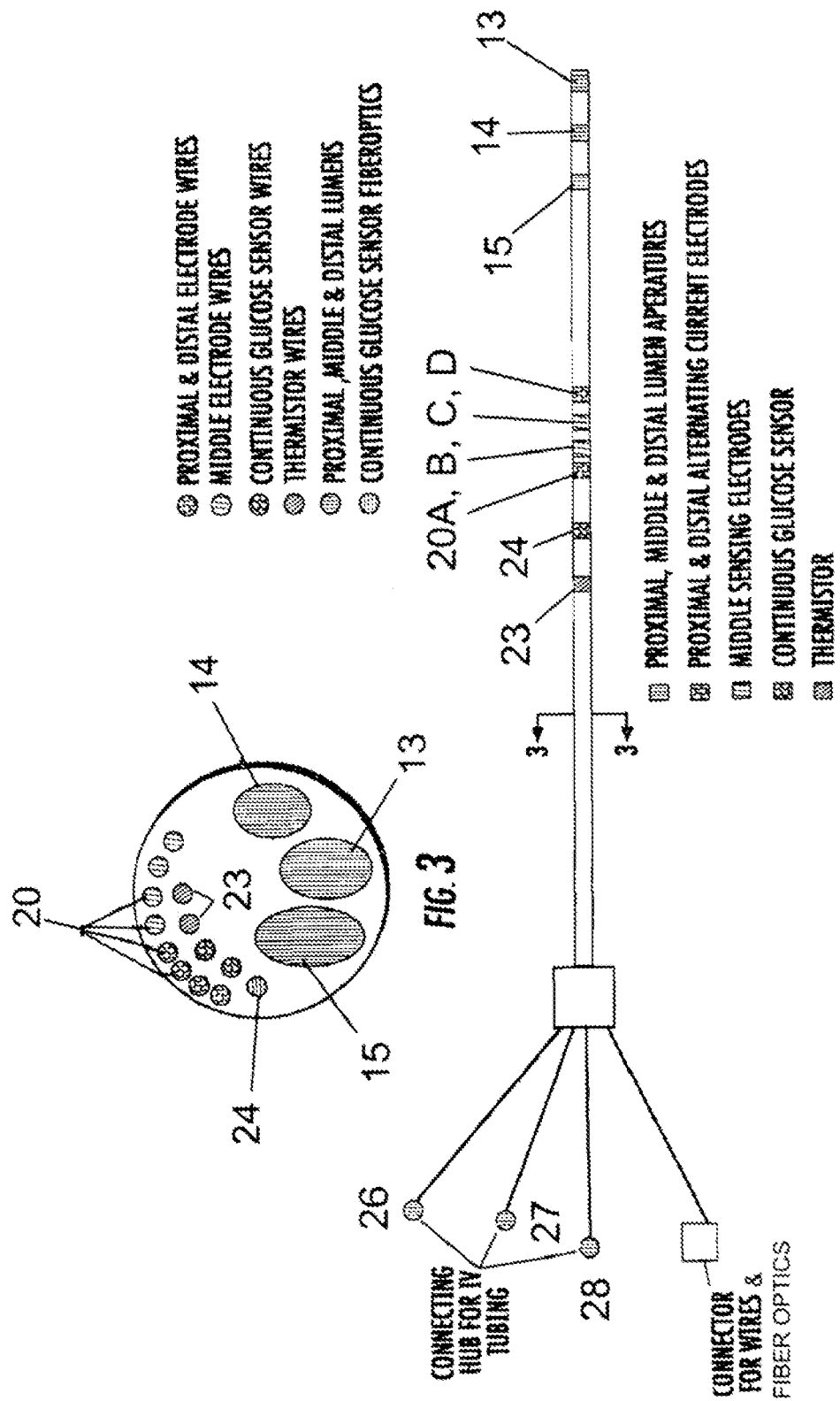

COMPUTERIZED SYSTEM FOR BLOOD CHEMISTRY MONITORING

CROSS-REFERENCE TO RELATED APPLICATIONS

This application is a continuation in part of international patent application Serial No. PCT/US08/73959 filed on Aug. 22, 2008, and published on Mar. 12, 2009, as WO 2009/032553, which is incorporated by reference in its entirety. The predecessor international application claims the benefit of priority based on U.S. Provisional Patent Application Ser. No. 60/969,582 filed in the United States Patent and Trademark Office on Aug. 31, 2007, which is hereby incorporated by reference in its entirety. The international case, as well as this application, also claims the benefit of U.S. Patent Application Ser. No. 60/973,891 filed on Sep. 20, 2007, which is incorporated by reference in its entirety.

FIELD OF THE INVENTION

The invention relates to a system of intravenously monitoring a patient's blood chemistry and transmitting real time measurements to an electronically controlled closed loop system that auto-regulates blood osmolality and glucose levels with medications infused through a new catheter design.

BACKGROUND OF THE INVENTION

In clinical medicine, swelling of the brain occurs in several common disease states such as (1) traumatic brain injury, (2) stroke, (3) survivors of cardiac arrest, (4) meningitis, (5) encephalitis and (6) brain tumors. Other less common conditions can also produce swelling of the brain. Physicians currently use several methods to treat both the brain swelling and the elevated intracranial pressure associated with it. These methodologies include intracranial pressure monitoring, removal of cerebrospinal fluid if an intraventricular catheter is in place, mechanical ventilation to prevent hypoxia and hypercarbia, strict control of fluid balance to provide for a normal intravascular fluid volume while avoiding hypo-osmolality, use of osmolar agents to create a hyperosmolar state, elevating the head of the bed, sedation and paralysis as needed. Routine surveillance of the intracranial vault with CT scans of the head is also used to rule out space occupying lesions that would be amenable to surgical removal.

Recent studies have also shown that use of hypothermia with body temperatures lowered to 32-34 degrees Celsius within 4 hours of the onset of traumatic brain injury[1] or cardiac arrest[2] can improve neurological outcome.

In addition, uncontrolled hyperglycemia has been shown to adversely affect mortality rates in traumatic brain injury[3], stroke[4], and cardiac arrest[5].

It has also been shown that strict control of blood glucose can improve mortality rates in post-operative patients and in medical ICU patients who remain in the ICU for at least three days.[6,7,8,9] Unfortunately, these studies and others[10] have shown that hypoglycaemia is a complication of strict glucose control utilizing an intravenous infusion of insulin.

In another treatment scenario, the continuous monitoring of serum osmolality, as provided by the catheter, will allow tighter control of serum osmolality, which may improve neurological outcome in patients with cerebral edema.[11] The iterative algorithm created to control an infusion of hypertonic saline will help clinicians achieve the goal of tight osmolality control.

Prior efforts in biomedical engineering have attempted to address similar goals. One of the earliest attempts at intravenous medical intervention is set forth in U.S. Pat. No. 4,072,146 (Howes 1978) entitled Venous Catheter Device. The Howes '146 patent discloses a catheter with a plurality of independent and non-communicating fluid conveying lumens housed within or formed in a single catheter. Each lumen transports a different fluid—or solution for entry into the patient's bloodstream.

U.S. Pat. No. 4,403,984 (Ash 1983) expands upon the concept of intravenous infusion and discloses a catheter with sensors for measuring in vivo the physical properties of blood. The signals from the sensor control infusion of medication, such as insulin, in response to a glucose measurement. The Ash '984 catheter measures osmolality via electrolytic conductivity of the blood. In one embodiment, Ash uses the osmolality reference signal as the insulin distribution control signal.

A series of patents issued to Schulman and granted as U.S. Pat. Nos. 5,497,772; 5,531,679; 5,660,163 show glucose sensors positioned within a patient's bloodstream for glucose and oxygen monitoring purposes. Schulman, however, does not show any in-depth means of adjusting glucose in a controlled process.

In determining blood conductivity, noted as useful in the Ash '984 patent above, U.S. Pat. No. 5,827,192 (Gopakumaran 1998) discloses an in vivo method of determining blood conductivity within the patient's heart. By utilizing spaced electrodes on a catheter, the Gopakumaran patent shows that blood conductivity can be determined from an induced voltage from a known current.

Still, however, none of the patents discussed above utilize a truly closed loop process for measuring multiple parameters, such as conductivity, osmolality, and glucose concentration, to adjust blood chemistry via infusions of multiple medicines or fluids. In regard to the osmolality measurements described herein, a conductivity sensor such as that of U.S. Pat. No. 4,380,237 (Newbower 1983) is available to provide blood conductivity measurements. Newbower, however, is limited in its disclosure to cardiac measurements that do not focus on glucose or osmolality readings. The Newbower '237 patent, then is limited in its disclosure.

The only known patent that even broaches the topic of a multi-variable closed loop system is U.S. Pat. No. 6,740,072 (Starkweather 2004). The Starkweather '072 patent discloses a system and method of providing closed loop infusion delivery systems that determine the volume of an infused substance via a sensed biological parameter. The Starkweather '072 controller is a multiple input single output controller using a proportional component and a derivative component of blood glucose measurements. The proportional component is simply the difference between the measured glucose level and the desired set point. The derivative component shows the rate of change for real time glucose level measurements. An appropriate controller then adjusts the single output—insulin dose. Starkweather, however, is limited in its ability to account for nonlinear physiological responses such as blood levels for glucose and osmolality. Specifically, in hypoglycaemic states the Starkweather controller's only response is to lower or stop the insulin infusion. It does not include any active interventions to raise the blood glucose level such as initiation of a glucagon infusion in the outpatient setting, or initiation of a glucagon or dextrose infusion in the inpatient setting.

Even in light of the above noted developments, there continues to be a need, in the art of blood chemistry intervention for a means of monitoring and controlling non-linear physiological responses in the blood stream. In particular, there is a need for a closed loop system that successfully adjusts blood chemistry parameters, including but not limited to glucose and osmolality, in real time emergency and non-emergency settings.

To accomplish these and other goals of the invention, the apparatus and system disclosed herein provide a means for closed loop electronic monitoring and blood chemistry regulation.

BRIEF SUMMARY OF THE INVENTION

A computerized glucose adjustment system intravenously controls a patient's blood chemistry on a real time basis. The system encompasses hardware including a catheter placed within the patient's vascular system, a glucose sensor attached to the catheter and in contact with the patient's bloodstream, and a pump connected to a source of insulin and a source of dextrose for distributing insulin and dextrose into a patient's bloodstream through the catheter. A computer processor is in electronic communication with the sensor and the pump such that the processor receives an electronic signal from the sensor to calculate the patient's real time average blood glucose level over a specified time period. A glucose control module stored in the processor sends output signals to the pump for controlling the rate at which the pump distributes insulin and dextrose into the patient. The glucose control module incorporates pump controlling commands to (i) determine where the patient's real time average blood glucose level lies along a continuum of glucose values; (ii) track the rate at which the average blood glucose level is changing over time; and (iii) iteratively adjust the dextrose flow rate and insulin flow rate into the patient's body to adjust the average glucose level closer to a known normal glucose range.

In one embodiment, the dextrose and insulin flow rates are functions of the patient's weight. The glucose control module adjusts pump output by analyzing current glucose readings in relation to set ranges programmed into the control module, which allows user input for customizing ranges. The system calculates the rate at which the average glucose level changes from one of said specified time periods to the next and determines an insulin flow rate adjustment factor and a dextrose flow rate adjustment factor. The adjustment-factors allow the pump to change insulin and dextrose flow rates to stabilize glucose levels in the patient toward a desired normal value.

The system may further include a blood osmolality adjustment system for intravenously controlling a patient's blood osmolality on a real time basis. In this embodiment, the system includes a catheter placed within the patient's vascular system, a conductivity sensor assembly attached to said catheter and in direct contact with the patient's bloodstream, a pump connected to a fluid source for infusing the fluid into a patient's bloodstream through the catheter, and a computer processor in electronic communication with the blood conductivity sensor assembly. The computer processor converts blood conductivity into an osmolality measurement. The processor is also in electronic communication with an associated fluid pump. A fluid infusion control module stored in the processor controls the pumped fluid flow rate. The fluid infusion control module comprises pump controlling commands to (i) determine where the patient's real time average osmolality lies along a continuum of osmolality values; (ii) track the rate at which the blood osmolality is changing over time; and (iii) iteratively adjust the pump output so that the fluid flow rate into the patient's body adjusts the average osmolality level closer to a known normal range. In one embodiment, the fluid is hypertonic saline. The system controls pump output by assigning a current average blood osmolality value to ranges along a continuum. The system iteratively adjusts flow rates pursuant to previously established instructions for each range.

BRIEF DESCRIPTION OF THE DRAWINGS

FIG. 1 schematically depicts a side view of the catheter according to the present invention and shows the multi-lumen interior through a cut-out view.

FIG. 2 is an overview schematic of the catheter including lumen ports and sensors.

FIG. 3 is a cross section view of the catheter of FIG. 2.

DETAILED DESCRIPTION

Overview

The method, system, and computer program product of this invention present a comprehensive algorithm, implemented via a computerized control system, for stabilizing a human's blood chemistry. While the features presented here are often described in terms of in-patient hospital medical procedures, the method and apparatus embodiments are not limited to any particular medical setting. The iterative method of this invention may utilize fuzzy logic mathematics[12] for greater accuracy in modifying infusion rates into the bloodstream.

The algorithms implemented by the computer program product set forth herein are set forth in the attached appendices. Tables A-D are incorporated by reference into this Detailed Description and represent respective embodiments of the control algorithms that adjust a patient's blood chemistry on a real time basis.

The blood chemistry predominantly at issue in this invention includes, but is not necessarily limited to, values for blood glucose and blood osmolality levels. In the glucose adjustment algorithm of this invention both an insulin infusion and a high dextrose infusion can be used to lower the likelihood of glycemic abnormalities. As it repeats itself over a specified time period and utilizes a closed loop control system, the algorithm responds to changes in blood chemistry values in a fashion similar to the normal human body's own pancreas and liver.

Specifically, the glucose algorithm, also referred to as a computerized glucose adjustment system, increases the insulin infusion in states of hyperglycaemia, or increasing glucose. In states of hypoglycaemia, or decreasing glucose, it lowers the insulin infusion and starts a high dextrose infusion. The infusion rate changes can be sudden or gradual depending on the real time measurements coming from the sensors (20, 23, 24) on the catheter (10) placed in the patient's blood stream. The control loop system is sufficiently automated to lessen the work required by a bedside nurse to achieve strict glucose control. The algorithm and associated computerized process for controlling blood chemistry in a medical setting will save not only lives but also health care resources.[13]

Figure 4:
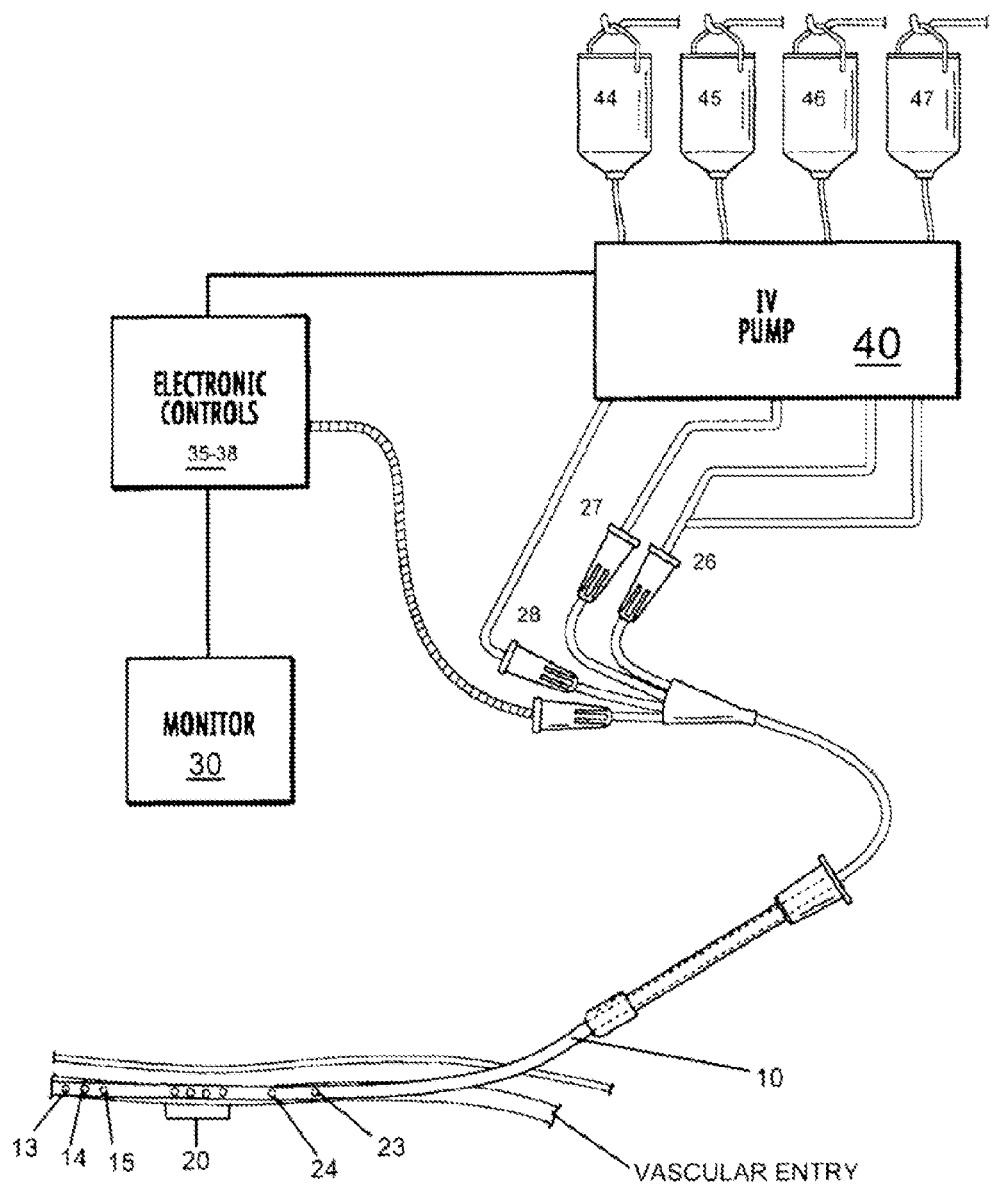
FIG. 4 shows the catheter according to this invention installed in its measuring/dispensing state and connected to the closed loop blood chemistry regulation system.
Figure 5:
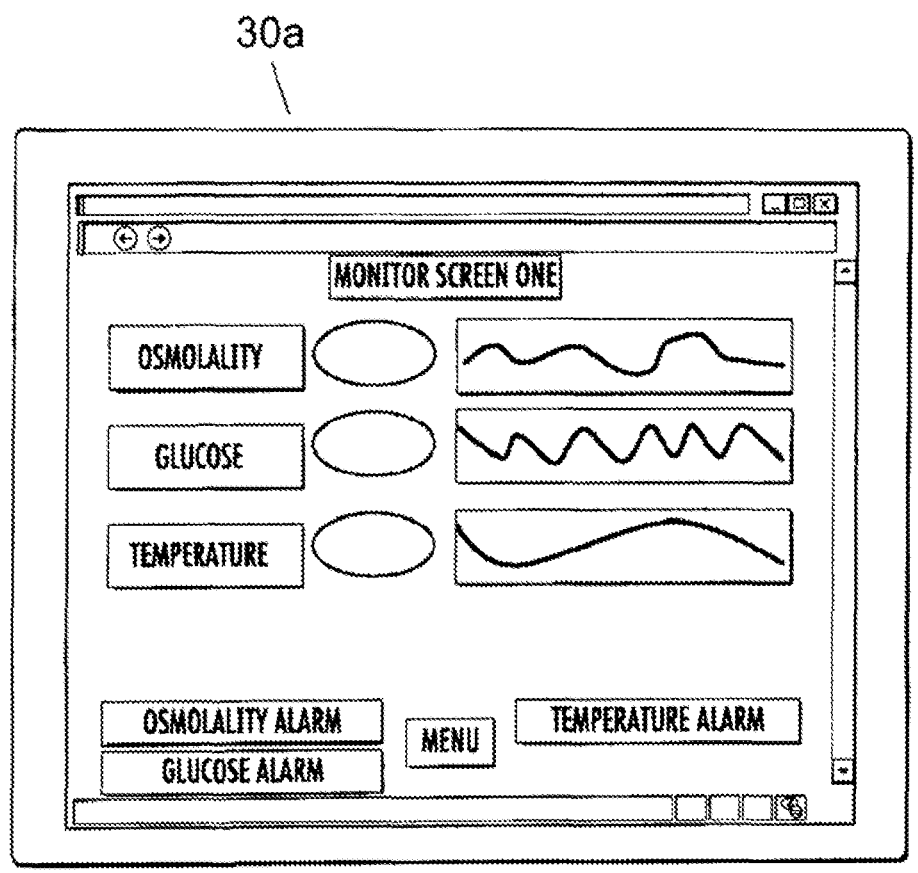
FIG. 5 shows a first screen available on a monitor included in the closed loop system along with alarms within the monitor.
Figure 6:
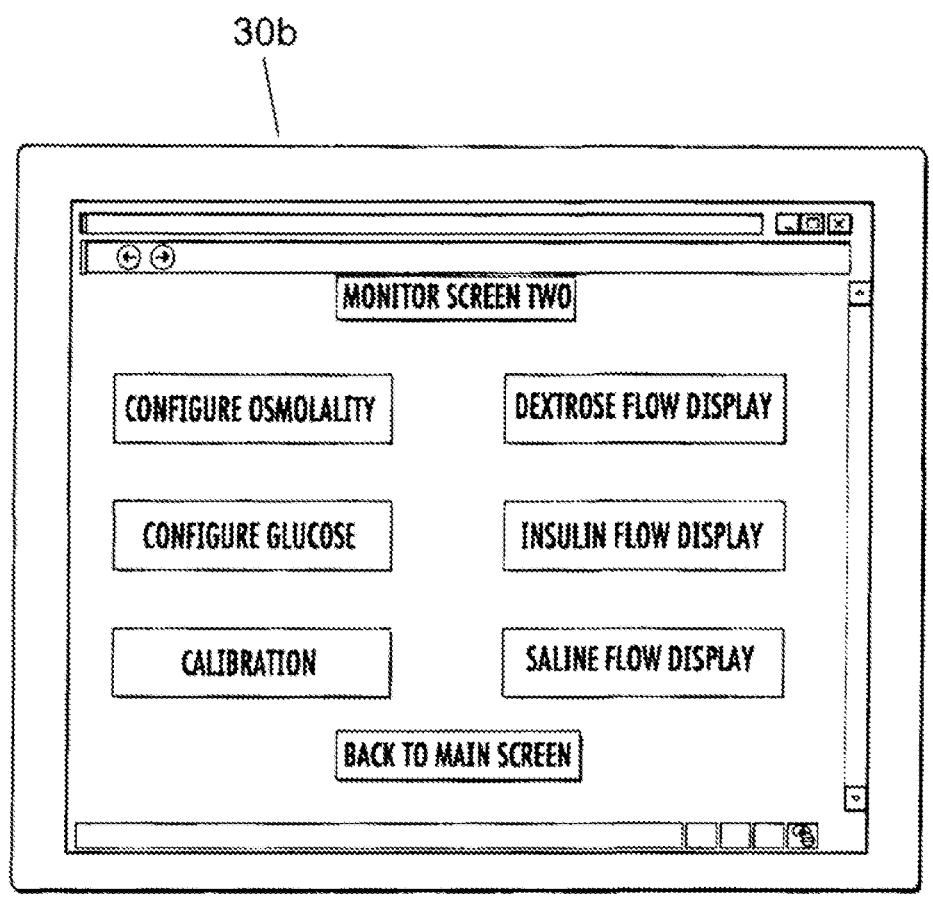
FIG. 6 shows a screen available on a monitor included in the closed loop system.

Referring to FIG. 1, an intravascular catheter (10) includes a plurality of lumens (13, 14, 15) designed for placement in a patient's vascular system, often the central venous system. Two or more lumens allow for administering intravenous fluids (e.g., electrolytes, nutrients, and medicine) and monitoring of the central venous pressure via a transducer connected to one of these lumens. As shown in FIG. 4, in one embodiment, the lumens (13, 14, 15) are connected to four intravenously administered fluid sources, which may include standard maintenance fluid (44), an insulin source (45), a dextrose source (46), and a source of hypertonic saline (47). The intravascular catheter (10) also contains the following three components: (i) a thermistor (23) for continuous real time temperature monitoring, (ii) a glucose sensor (24) for continuous real time blood glucose, level monitoring, and (iii) a conductivity cell (20), (with each electrode shown individually in FIG. 1 as 20A, 20B, 20C, and 20D) for continuous real time measurement of the blood's electrical conductivity. Each of the sensors (20, 23, 24) are known in the medical arts individually and can be implemented via standard equipment.

By using the computerized method of this invention, the electrical conductivity measurements from electrodes 20A to 20D can be converted to osmolality by using the formula:

$$\text{Serum osmolality} = 18.95 \text{ mOsm/mSiemen} \times (\text{measured conductivity(mSiemen)}).$$

The apertures (17, 18, and 19) of the plurality of lumens (13, 14, 15) may be located along the distal end of the intravascular catheter (10) with the most distal aperture (19) being at the farthest point into the vein. The proximal portions of the plurality of lumens (13, 14, 15) may be separate hollow tubes with proximal ends (26, 27, 28) that can be connected to standard intravenous tubing.

The three measuring components (20, 23, 24) electronically transmit their respective values to an electronic control system (35) (i.e., software and hardware programmed to accept and utilize this data). The electronic control system (35) may be integrally connected to hardware and software that implements algorithms for controlling fluid and medicine administration in the closed loop system. In this regard, the term "electronic control system" includes a computerized glucose adjustment system ("the glucose control module" (36)), a computerized osmolality adjustment system ("the osmolality control module" (38)), maintenance fluid commands, and electronic control hardware ("controllers" and/or "processors" (37)). The closed loop control system (35) maintains the readings on an associated monitor (30) that includes alarms for alerting medical personnel to a patient's blood chemistry fluctuation.

The monitor (30) according to this invention includes, but is not limited to, readings for blood temperature, blood osmolality, blood glucose level, and trends for all of these. The monitor may further show trends for dextrose flow rate, insulin flow rate, and hypertonic saline flow rate. As in typical bedside equipment, the monitor of this invention will have an on/off button, a calibration mode, and arrows to adjust monitor readings, just to name a few features.

The monitor (30) includes a plurality of displays including temperature with a range of 30° C. to 42° C. or 86° F. to 107.6° F., serum osmolality with a range of 240 to 380 mOsm/Kg and blood glucose with a range of 40 mg/dL to 400 mg/dL. Each measurement has a high and low alarm on the monitor, which is controlled by the programmable system.

In one embodiment, the osmolality and glucose measurements may be calibrated against the same measurements carried out on blood drawn from the patient. In the case of the glucose calibration, this calibration will be carried out at least every six hours. The blood for this calibration will come from either a finger-stick capillary sample, or central venous/arterial line sample. If the sample comes from an in-dwelling line, an amount of blood in sufficient quantity to clear the dead space of the line must be removed prior to obtaining the actual sample. In any case, the blood sample will be processed by a typical bedside glucose meter, bedside YSI glucose meter, or the hospital's central laboratory. After determining the glucose level of the blood sample the glucose meter will transmit this value along with the time the sample was taken to the intravenous pump at the bedside. This transfer of information from the glucose meter to the intravenous pump will occur via either infrared or wireless technology with the intravenous pump having an appropriate infrared sensor or wireless sensor to receive this information. For purposes of calibration, the glucose value and time of sample may also be manually entered into the intravenous pump. Each of the blood factors being measured—temperature, glucose level, and osmolality—provide significantly better patient outcomes when monitored closely and efficiently. The portable bedside monitor which is part of the intravenous pump assembly will be capable of exporting the temperature, glucose and osmolality values to the fixed bedside monitor which may or may not be part of a hospitals mainframe computer system. This transfer of information will occur via either a wire cable extending from the intravenous pump to the bedside monitor, or via wireless technology. Other important elements of patient care such as hourly fluid rates and hourly medication rates may also be exported from the portable bedside monitor to the fixed bedside monitor or hospital mainframe computer system. This exportation of data may occur via an electronic cable or via wireless technology. In addition, the temperature measurement will be capable of being exported to other bedside devices for purposes of controlling the patient's temperature.

In another method of calibrating the system, the nurse could use a finger prick capillary sample in a bedside glucose meter. After reading the patient's current glucose level, the nurse would have the ability to manually calibrate the system with data entry. In a meter with an even higher level of automation, the bedside glucose meter could read the glucose level from the finger prick sample and then wirelessly transmit the patient's current glucose reading to the processors for automatic system calibration.

The electronic control system (35-38) receives real time data from the sensors on the catheter (10). The electronic control system presented herein, which includes standard programmable computer processors (37), uses known data transmission techniques along with a new control system algorithm (described herein) to maintain and regulate peripheral bedside devices. As shown in FIG. 4, the controller can regulate a four channel intravenous pump (40) to maintain the total hourly rate at which fluids and medications (44-47) are administered through the catheter (10).

The electronic control system (35-37) includes a computerized method of utilizing the patient's temperature, osmolality, and glucose data, as retrieved from real-time blood stream measurements, to control fluid and medication (44-47) infusion rates. The computerized method, claimed herein, uses the measured blood chemistry values with known standards of care to automate the fluid and medicine infusion process that is currently managed manually by medical personnel. In particular, the computerized method adjusts the flow rate of dextrose and insulin according to the data from the glucose sensor; it further adjusts hypertonic saline flow in response to osmolality readings.

The system described herein employs statistical methodologies to eliminate the values that exceed two standard deviations from the mean, thus excluding outlying values. A running average for the physiological parameter at issue minimizes the effect of short term oscillations of data. The algorithms serving as the basis for the computerized method of this invention are attached as two Appendices—one for the glucose control algorithm and one for the osmolality control algorithm.

Glucose Embodiment

In a first embodiment, the control loop of this invention implements a computerized glucose adjustment system for intravenously controlling a patient's blood chemistry on a real time basis. A catheter (10) is placed within the patient's vascular system, often within the central venous system. The catheter (10) includes a glucose sensor (24) that is currently known within the art as having the capability to measure a patient's blood glucose level and transmit that information back to a central computer processor[14,15] (37). The system described herein also encompasses the use of a subcutaneous glucose monitor that measures the patient's glucose level from the tissue just under the skin. The system described herein also encompasses the use of an extracorporeal glucose sensor that measures a patient's glucose level on blood that is automatically and repetively withdrawn from the patient's body via an indwelling vascular catheter. The computerized system incorporates a pump (40) connected, at a minimum, to a source of insulin (45) and a source of dextrose (46) for distributing insulin and dextrose into a patient's bloodstream through the catheter.

A computer processor (37) receives the blood glucose level from the glucose sensor attached to the catheter (10). The computer processor (37) is in electronic communication with both the sensor (24) and the pump (40) to use the glucose measurement to control pump output. Upon receiving the glucose measurement signal, the computer processor (37) calculates the patient's real-time average blood glucose level over the specified time period.

A glucose control module (36) stored in the computer processor (37) utilizes input glucose measurements to create output signals. The glucose control module (36) sends the output to the pump (40) for controlling the rate at which the pump (40) distributes insulin and dextrose into the patient. The glucose control module includes pump controlling commands programmed therein. This control module implements software to (i) determine where the patient's real-time average blood glucose level ("Xa") lies along a continuum of glucose values; (ii) track the rate at which the average blood glucose level is changing over time; and (iii) iteratively adjust the weight based dextrose flow rate and weight based insulin flow rate into the patient's body to adjust the average glucose level closer to a user specified normal glucose range.

Although infusing insulin (45) and dextrose (46) into patients has been known for years, utilizing controlled insulin and dextrose flow rates, particularly those calculated as a function of the patient's weight in kilograms, offers added functionality to a closed loop glucose management and adjustment system.

Implementing the computer-controlled glucose adjustment system herein may begin by programming the processor to accept as an input the initial concentration of the dextrose being infused into the patient. Typically the dextrose formulation has a concentration selected from the group consisting of 5, 10, 12.5, 15, 20, and 25 in percent weight per volume. The insulin formulation will also be a known concentration measured in International Units (IU)/mL. The typical concentration used at this time is 1 IU/mL.

The computerized glucose adjustment system, which operates continuously on a real time basis, iteratively receives glucose measurements from the glucose sensor (24) on the catheter (10), analyzes these measurements, calculates the average glucose level over a specified time period, and sends an output signal to the pump (10) managing dextrose (46) and insulin (45) infusion. To ensure that the glucose adjustment system (36) described herein performs in optimal fashion, the system is capable of allowing a user to set a known normal glucose range between Xmin and Xmax. This range becomes the target that the computerized glucose adjustment system seeks to achieve in real-time blood glucose measurements.

As a first step in reaching blood glucose levels within the selected range, the glucose control module (36) calculates and stores in appropriate mathematical units (typically milligrams per deciliter) an average blood glucose level Xa for a specified time period. For example, the glucose control module may calculate and store a "current" blood glucose value Xt (i.e., glucose sensor measurement at time t) in milligrams per deciliter every 30 seconds and then calculate the average glucose level Xa in milligrams per deciliter over a specified time period (e.g. 10 minutes). In other words, the glucose adjustment system keeps a running average of the blood glucose level as measured by the catheter's glucose sensor (24) in the patient's bloodstream. At any given time, the controller (37) has available to it the average blood glucose level for the previous 10 minutes, or whatever time period has been selected by the user. This 10 minute average glucose value is labelled as Xa. In addition the computer processor, or controller (37), has available to it the running glucose average for the period prior to the just completed 10 minute period, or whatever time period has been selected by the user. This value is noted as Xb. In addition the computer processor, or controller (37), has available to it the running glucose average for the period just prior to Xb. This value is noted as Xc.

The control loop operates via a series of pump controlling commands on the processor (37) that determine the flow rate of insulin (45) and dextrose (46) into the patient. The pump controlling commands are divided into categories defined by glucose control ranges along the continuum of glucose values. The glucose adjustment system defined herein involves the glucose control module (36) calculating which of the pump controlling command categories is appropriate for a particular average blood glucose value (Xa). In other words, as the glucose sensor (24) on the catheter (10) transmits a current blood glucose value back to the computer processor (37), the processor stores this value, and when all values for the specified time period have been stored, the processor electronically calculates the average blood glucose value (Xa) for this time period. The processor then assigns the average blood glucose value (Xa) to a category of pump controlling commands.

The pump controlling command categories are further divided into groups determined by the amount which the current average blood glucose value that has just been calculated (Xa) differs from the user set range of Xmin to Xmax.

The next step in the algorithm implemented by the computerized system is for the glucose control module (36) to compare the current average glucose measurement (Xa) to the prior average glucose measurement (Xb). This calculation determines the rate at which the average glucose level is changing between measurements. In one embodiment of this invention, the time between glucose measurements can be set by the user.

The system intelligently groups real-time human physiological parameters and determines the appropriate command or electronic signal that directs the pump output (i.e., the amount of insulin and dextrose infused into the patient.) The glucose adjustment system, including the glucose control module (36), directs pump controlling commands for adjusting pump output. The pump controlling commands direct the pump (not shown) to control the flow rates of insulin (45) and dextrose (46) according to the category in which the most recent average glucose calculation fits and the rate at which the glucose level is changing.

For example, the pump controlling commands depend, at least in part, upon the following conditions: (i) the amount the average blood glucose level (Xa) differs from a known or desirable normal range between Xmin and Xmax, (ii) the amount the average blood glucose level (Xa) has changed from a previously calculated value (Xb), (iii) the amount the average blood glucose value (Xa) has changed from the glucose value Xc, (iv) the known weight-based flow rates of insulin (Insfp) and dextrose (Dexfp) effective at the time the glucose measurement was taken, and (v) the time interval between Xa and Xb, and the time interval between Xa and Xc. Using these factors, the algorithm implemented herein determines how the insulin and dextrose flow rates from the pump should be increased or decreased to optimize the real-time blood glucose value (Xt) for the patient at issue.

Stated differently, the algorithm of this invention utilizes a blood glucose value transmitted from a glucose sensor (24) on an intravenous catheter (10) to the computerized glucose adjustment system. The glucose sensor (24) transmits real-time blood glucose measurements taken in vivo for the patient at hand. In one embodiment, the computer processor (37) is programmed to receive glucose sensor measurements at a specified time interval, such as every 30 seconds.

Once the average blood glucose level Xa has been calculated for a selected time period and the appropriate pump controlling command set determined, the computer processor turns to the steps involved in directing pump (40) output. As part of the glucose control module, the rates of insulin and dextrose infusion are maintained in electronic format for use by the controller. A medical professional sets initial values for insulin flow and dextrose flow. In the computer processor, these values would be the first values used for "previous" insulin and dextrose flow rates, referred to herein as Insfp and Dexfp respectively. Over each glucose measurement iteration, the processor uses the average blood glucose value Xa, the difference between (Xa) and the prior average glucose value (Xb), along with the most recent pump state for Insfp and Dexfp to determine how to calculate an updated pump command for the "next" insulin and dextrose flow rates, Insfn and Dexfn. In the initial run through the glucose control algorithm, the value of Xb is set equal to the measured value of Xa, such that: Xa−Xb=0.

In one embodiment of this invention, the pump controlling commands adjust the insulin (45) and dextrose (46) flow rates going into the patient as a function of the patient's weight in kilograms (Wt). For insulin flow, the pump controlling commands use a multiplier, such as a value between 0 and 1.7, times the prior insulin flow rate to determine the extent to which the weight-based insulin flow rate should be changed. For dextrose flow, the pump controlling commands include, but are not limited to, using flow rate multipliers divided by the initial dextrose concentration (C) value set by the medical professional and multiplied by the patient's weight in kilograms (Wt). These insulin and dextrose flow rate calculations determine which of several flow rate adjustment factors can be used and converted to pump controlling command output signals. As noted above, the pump controlling commands direct the pump to change the infusion flow rate for the respective insulin and/or dextrose. The pump used in this embodiment can be any one of a number of standard multi-channel pumps known in the industry. In a preferred embodiment, the pump is capable of controlling fluid flow rates with an accuracy down to one tenth of a milliliter per hour.

To further assist the medical professional in monitoring a patient, the system includes software for setting high and low alarm set points for glucose values, insulin and dextrose flow, and for differentials between consecutive glucose measurements. For example and without limiting the invention, a nurse tending a patient might set the low glucose alarm at 60 mg/dL, and the high glucose alarm at 240 mg/dL. Similarly, the controller can activate an alarm if the differential between the current average glucose value Xa and immediately prior average glucose value Xb is greater than 25 or less than −25 mg/dL. Where these kinds of glucose changes previously required drawn blood, lab work, and nurse or physician review, the system of this invention makes the information and alarm almost immediately available for attention.

Another way of describing the glucose adjustment embodiment of this invention is in terms of the method of using insulin and dextrose flow rate adjustment factors to optimize glucose levels. As set forth herein, a computerized method of adjusting a patient's blood chemistry on a real time basis includes adjusting the patient's average glucose level toward a user-specified normal range by multiplying a currently known weight-based insulin flow rate and a currently known weight-based dextrose flow rate by adjustment factors. The adjusted flow rates control the amount of insulin and dextrose pumped into a patient's bloodstream. The method of this invention begins by continuously measuring the patient's real time glucose level, storing each real time glucose level in a computer processor, and calculating via a computer processor an average glucose level, Xa, over a specified time period.

The method further includes electronically assigning the average glucose level to one of a series of glucose control ranges. By calculating the rate at which the average glucose level changes from one specified time period to the next, the method determines the insulin flow rate adjustment factor and the dextrose flow rate adjustment factor necessary to achieve a normal glucose range as specified by the bedside clinician.

The insulin flow rate adjustment factor and the dextrose flow rate adjustment factor depend upon the state of the respective weight-based insulin and dextrose flow rates already in effect for the patient at hand. The adjustment factors are not static numbers that remain the same for every patient, but rather, the adjustment factors generally depend upon the difference between the measured glucose level and the desired range, the rate of change of the glucose level from one time period to the next, and the previous weight-based flow rates of insulin and dextrose. For example, and without limiting the invention, one useful calculation in adjusting insulin flow rate involves comparing the previous insulin flow rate to a patient's weight in kilograms (Wt). In this embodiment, the next insulin flow rate (Insfn) depends upon where, along a range of weight-based flow rates, the previous insulin flow rate (Insfp) falls. The next dextrose flow rate (Dexfn) depends upon where, along a range of weight-based flow rates, the previous dextrose flow rate (Dexfp) falls. In addition, other factors such as the difference between the measured glucose level and the desired range, the rate of change of the glucose level from one time period to the next and the prior weight-based flow rates of insulin and dextrose are taken into account. In order to account for differences in dextrose concentrations used, the inverse of the dextrose concentration is multiplied times the patient's weight in kilograms to determine the dextrose flow rate in mL/hour. This will result in a dextrose flow rate in grams per kilogram per hour that is independent of the user specified dextrose concentration. In it's current format, the glucose control algorithm assumes that the insulin concentration used will be 1 international unit/mL. If an alternative insulin concentration is used, the INSfn, as determined by the algorithm, will need to be multiplied by the inverse of the insulin concentration. As an example, if an insulin concentration of 0.5 international units/mL is used, then INSfn will by multiplied by (1/0.5=2) to come up with the appropriate flow rate of INSfn in mL/hour.

Stated differently, the computerized glucose adjustment system of FIG. 4 implements software to (i) determine where the patient's real-time average blood glucose level ("Xa") lies along a continuum of glucose values; (ii) track the rate at which the average blood glucose level is changing over time; (iii) determine the status of the previous weight based insulin flow rate; and (iv) determine the status of the previous weight-based dextrose flow rate. By determining these four parameters, the system of this invention utilizes pre-programmed insulin flow rate adjustment factors and dextrose flow rate adjustment factors to change the flow rates for the next time period. The system continuously updates this process with new measurements from the glucose sensor (24) and any changes input manually by a medical professional.

The computer processor's glucose control module groups the following values in determining the insulin and dextrose adjustment factors: (i) difference between the most recently calculated average blood glucose value and the desired glucose range; (ii) the rate at which the average blood glucose value is changing over a specified time period; (iii) the value of the weight-based insulin flow rate; and (iv) the value of the weight-based dextrose flow rate. By grouping these parameters each time a new average glucose level Xa is calculated, the system better selects the appropriate insulin and dextrose flow rate adjustment factors. In some cases, the insulin and dextrose flow rates will be changed from zero to a positive value greater than zero. At other times, the insulin and dextrose flow rates will be changed from a positive value to zero.

In one embodiment, the dextrose adjustment factor is selected from the group consisting of 0, 0.7, 0.75, 0.8, 0.85, 0.9, 0.95, 1.0, 1.05, 1.1, 1.2, 1.25, 1.3, 1.4, 1.5, and 1.7. Additionally, the insulin adjustment factor may be selected from the group consisting of 0, 0.5, 0.75, 0.80, 0.85, 0.9, 0.95, 1.0, 1.05, 1.1, 1.15, 1.2, 1.3, 1.4, 1.5, 1.6, and 1.7. In order to improve its speed at arriving at the user specified normal glucose range, the system may be programmed with a step of administering bolus doses of insulin for all glucose values greater than or equal to Xmax+20 mg/dL, and when the rules of either 218, 219, or 220 are met. These bolus doses may not be administered more often than every 30 minutes. As mentioned above, the medical personnel may manually set the values of an initial insulin flow rate and an initial dextrose flow rate prior to the step of continuously measuring the patient's real time glucose, level.

In other embodiments, the dextrose flow rate and the insulin flow rate are adjusted by an amount determined according to the patient's weight. As noted above, the dextrose formulation typically has a concentration (C) selected from the group consisting of 5, 10, 12.5, 15, 20, and 25 in percent weight per volume. The dextrose flow rate may be adjusted in a computer controlled process that determines the next flow rate as a multiple of 1/C multiplied by the patient's weight. In some instances, the above numerator 1 may be changed to 2, 3 or 6. In weight based insulin flow management, a known weight multiplier (e.g. 0.01, 0.02, 0.03) may be multiplied by the patient's weight to determine the next insulin flow rate when the previous insulin flow rate was zero.

As noted in the attached Table, when the closed loop system detects glucose levels above a certain maximum, the insulin flow rate would include a calculated flow rate according to the algorithm plus a bolus dose to rapidly adjust the glucose level to a normal range.

The algorithm for setting the next insulin infusion rate (INSfn) includes an additional checking protocol to account for critical situations in which the glucose values are outside the desired range and varying widely. The checking protocol for these situations is referred to herein as the Secondary Controller. The Algorithm for the Secondary Controller is set forth in more detail below. Without limiting the invention to any one set of instructions, the Secondary controller may include instructions for fine tuning the next insulin flow rate (INSfn) to an adjusted value (INSfn2c) output from the Secondary Controller (referred to as "2C").

The Secondary Controller accounts for situations in which the currently averaged glucose value Xa is less than the minimum desired value (Xmin). In addition, the secondary controller is designed to handle outlier situations whereby the glucose is rising or falling at an excessive rate, such that the primary controller may not be able to keep up with the rate of change. The secondary controller can change the cycle interval of the glucose controller from its standard interval of ten minutes to five minutes, and back to ten minutes as needed. This provides additional feedback to the system for adjusting the glucose value more rapidly when the glucose is too low, or rising/falling too rapidly.

The Secondary Controller is actually a series of secondary controllers that are executed one after another until all 27 rules have been assessed for relevancy to the current situation at hand. The order and function of the series of secondary controllers is as follows:

a) Rules 1-8: These rules modify INSfn when Xa is <Xmax and the rate of glucose change (Xa−Xb) is excessive given the current glucose level=Xa.

b) Rule 9: This rule serves to initiate a dextrose infusion when the current glucose level Xa is <100 mg/dL and the rate of fall of glucose is <−12 mg/dL per 10 minute period=a rate of fall<−1.2 mg/dL/min and the primary glucose controller rule for Dexfn is 0.

c) Rules 10-11: These rules modify Dexfn when the rate of fall or rise of glucose is excessive and the rule for Dexfn is >0 mL/hour.

d) Rules 12-19: These rules modify INSfn when the current glucose value Xa is Xmax and the rate of rise or fall of glucose is excessive.

e) Rules 20-27: These rules switch the cycle interval between the standard interval of 10 minutes and a more frequent cycle of 5 minutes based on the current glucose level (Xa) and the rate of rise or fall of glucose.

Thus, the cycle interval is not fixed; rather, it fluctuates based on the values of Xa and (Xa−Xb). If the cycle interval is changed to 5 minutes, the subsequent values of (Xa−Xb) must be multiplied by 2 before the (Xa−Xb) value is run through the primary and secondary glucose control algorithms, as the algorithms were built on a standard cycle interval of 10 minutes. There will be no modification of (Xa−Xb) if the cycle interval is 10 minutes. Details of the Secondary Controller are set forth at Paragraph 113 following the Osmolality Algorithm Table below.

The pump (40) receives the updated insulin/dextrose data from the glucose control module (36) and adjusts output accordingly.

Figure 7:
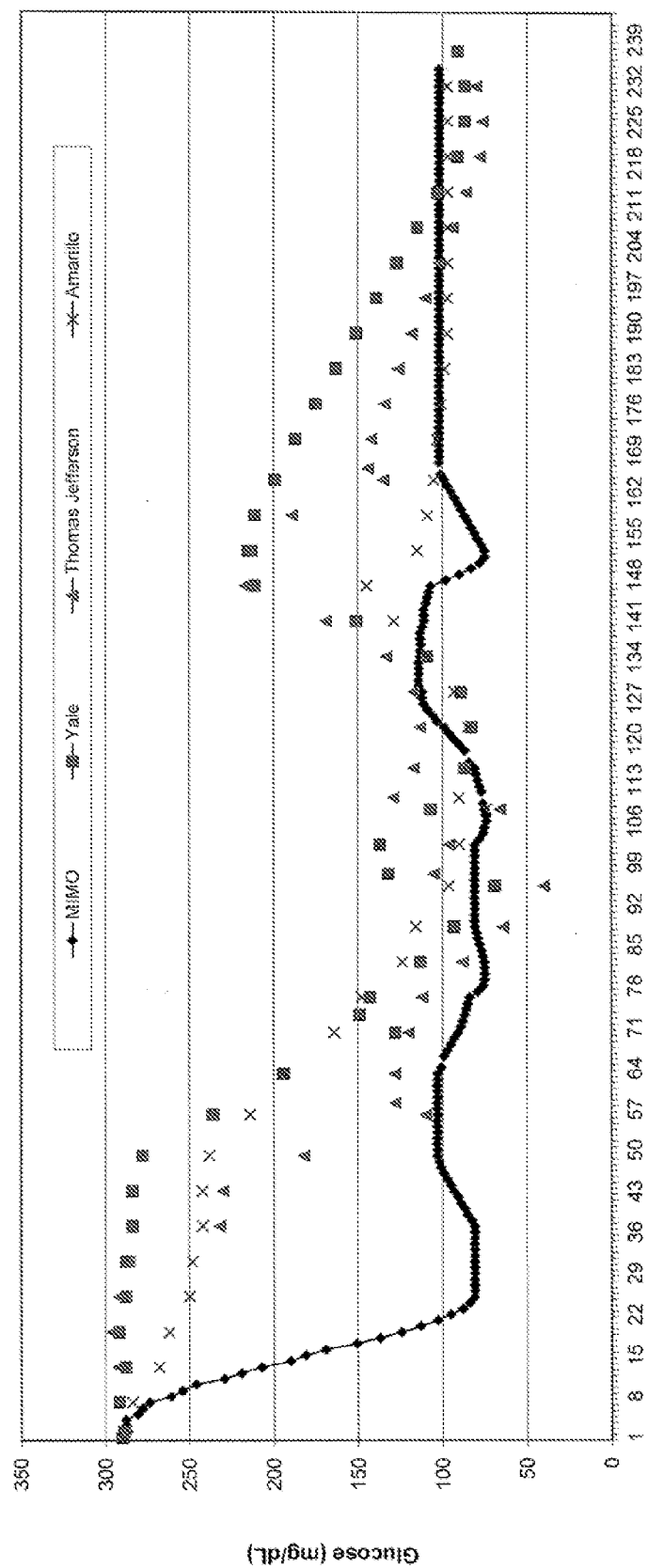
FIG. 7 is a plot of glucose levels over time for the protocol described herein as compared to other published protocols for real time glucose management.

The glucose adjustment system disclosed herein exceeds the accuracy of previously known protocols used in numerous medical settings. FIG. 7 shows a plot comparing (i) the glucose levels that would be attained using the currently described automated protocol (denoted "MIMO" for multiple input multiple output) with 10 minute cycling intervals and (ii) paper protocols previously used to adjust glucose levels with nurse or physician supervision (i.e., Yale[16], Thomas Jefferson[17], and Amarillo[18] paper protocols). The results of the paper protocols are compared to those of the new MIMO system utilizing a new simplified ICU glucose-insulin model to estimate results that the paper protocols would most likely achieve. FIG. 7 indicates that the automated protocol described herein achieves a tighter glucose control more quickly than the paper protocols.

Figure 8:
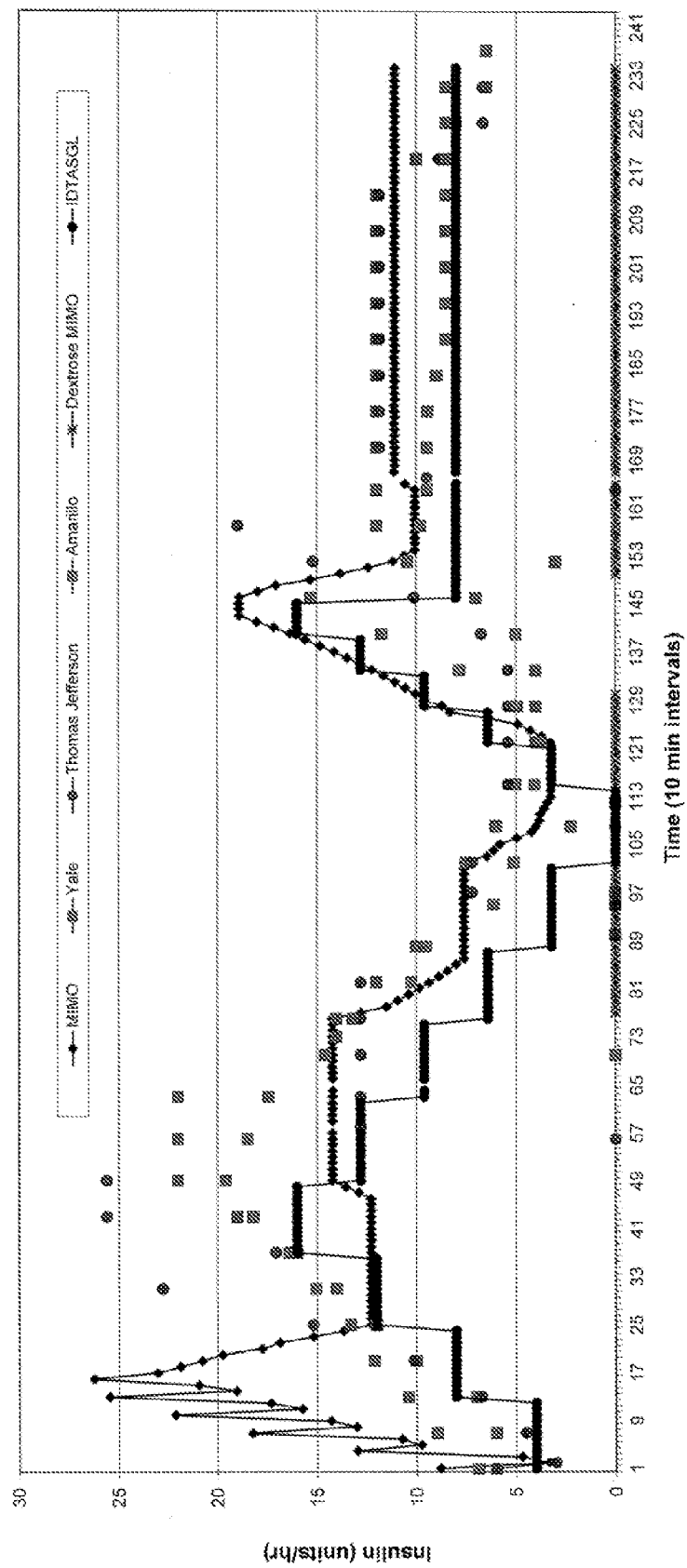
FIG. 8 is a plot of insulin flow rate over time as compared to other published protocols for real time glucose management.

FIG. 8 shows the corresponding insulin flow rates for each protocol of FIG. 7. FIG. 8 further illustrates that, in addition to utilizing a continuous infusion of intravenous insulin to lower elevated glucose levels, the automated model also uses a continuous infusion of dextrose in states of hypoglycemia to account for glycogenolysis/gluconeogenesis.

Overall, FIGS. 7 and 8 illustrate a simplified patient model to test the results of the new controller against known paper based insulin protocols. The concept of the Insulin Dose To Achieve Static Glucose Level (IDTASGL) is shown in FIG. 8. This is the exogenous insulin dose at which the glucose elevating effects of stress hormones, intravenous dextrose, enteral feeds, steroids, etc are balanced by the glucose lowering properties of the exogenous insulin, and the blood glucose, regardless of its level, will remain static. Rules are provided in the simplified ICU glucose-insulin model to account for the rate of rise of blood glucose when the exogenous insulin dose is less than the IDTASGL, and the rate of fall when the exogenous insulin dose exceeds the IDTASGL. In the examples of FIGS. 7 and 8, the controller adjusts its insulin dose every ten minutes. The insulin protocols used for comparison are cycled as frequently as allowed by the protocol.

Figure 9:
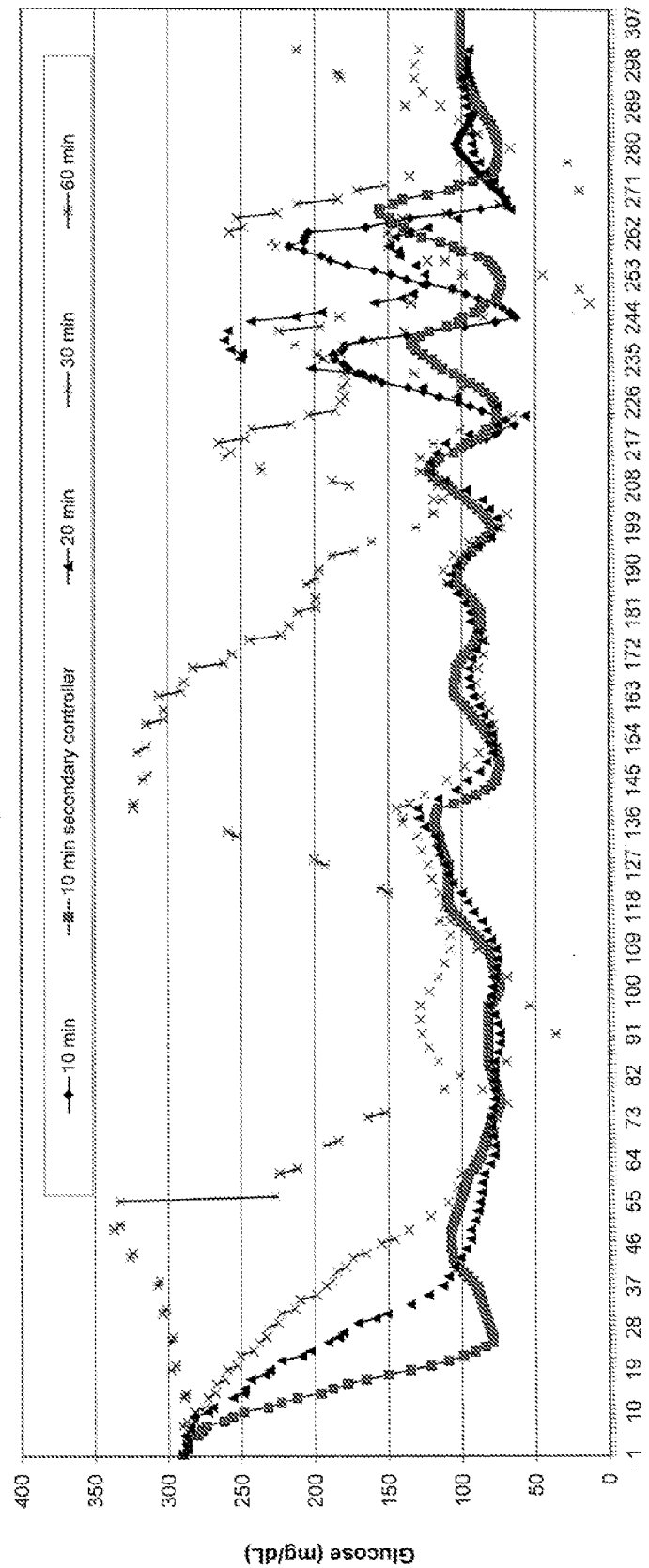
FIG. 9 is a plot of glucose levels over time when the protocol disclosed herein is used at varying time intervals.

FIG. 9 illustrates the results when the MIMO protocol is also compared to itself using different cycle intervals. The shorter cycling intervals produce tighter glucose control. For ease of calculation, each new insulin dose is judged to have effect only during the period of that doses infusion. The IDTASGL changes throughout the test period to simulate that which occurs in real life. In the comparison of different cycle interval scenario, the insulin effects were increased by 300% at the $26^{th}$ hour or $156^{th}$ time interval mark.

Figure 10:
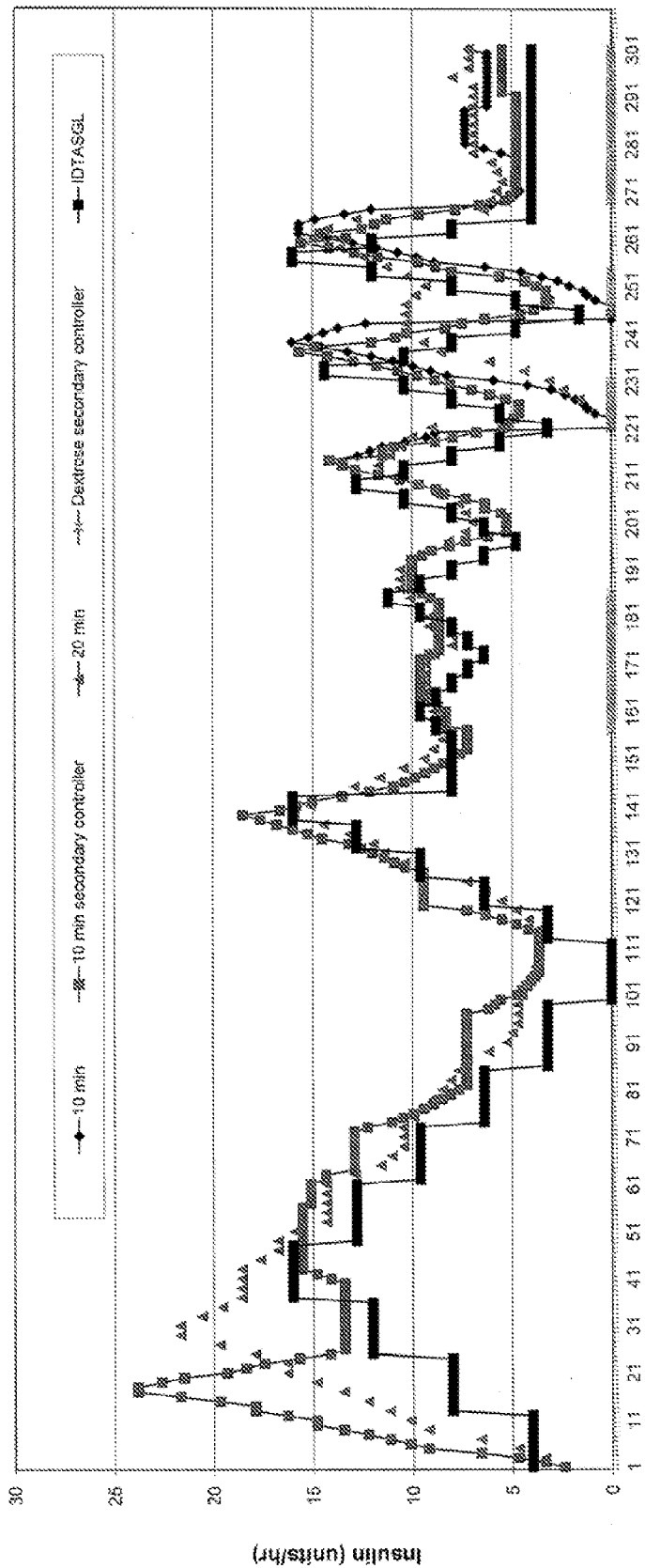
FIG. 10 is a plot of insulin flow rate over time when the protocol disclosed herein is used at varying time intervals.

FIG. 10 shows the insulin flow rates corresponding to the glucose management of FIG. 9 using the MIMO protocol described herein.

Osmolality Embodiment

In a different embodiment of the system, the computerized method accomplishes blood osmolality management via a blood osmolality adjustment system. As noted above, the system includes a catheter (10) placed within the patient's vascular system for direct contact with the bloodstream. The catheter (10) includes a conductivity sensor (20) attached to the catheter. The conductivity sensor (20) may be formed of various configurations that are commonly used in the art of biomedical engineering. In general, however, one particularly useful embodiment of the conductivity sensor (20) includes four electrodes (20A, 20B, 20C, and 20D) in direct contact with the bloodstream. A current driven across one pair of the electrodes (20A, 20D) passes through the bloodstream and induces a voltage across two other sensing electrodes (20B, 20C). The voltage signal transmits back to a computer processor (37) which converts the signal to an osmolality measurement by the following formula:

Serum osmolality(mOsm)=18.95 mOsm/mSiemen× Measured conductivity(mSiemen))

In line with the glucose embodiment detailed above, the system of this invention includes the ability to regulate blood osmolality with a fluid infusion from an electronically controlled pump (40). In one embodiment, the pump (40) is connected to a source of saline (47) and adjusts the amount of saline infused into the patient's bloodstream in response to blood conductivity measurements from the conductivity sensor (20). In a preferred embodiment, the saline is hypertonic saline.

A computer processor (37) calculates the osmolality level as a function of the blood conductivity measured from the voltage signal transmitted from the conductivity sensor (20) attached to the catheter (10). The computer processor (37) is in electronic communication with both the sensor (20) and the fluid pump (40) to use the blood conductivity/osmolality measurement to control pump output. Upon receiving the osmolality calculations from the blood conductivity measurements, the computer processor (37) calculates the patient's real-time average osmolality level over the specified time period.

A fluid infusion control module stored in the computer processor (37) utilizes input osmolality measurements to create output signals. The fluid infusion control module sends the output signals to the pump for controlling the rate at which the pump distributes saline into the patient. The fluid infusion control module includes pump controlling commands programmed therein. These commands implement software to (i) determine where the patient's real-time average blood osmolality level ("Ya") lies along a continuum of osmolality values; (ii) track the rate at which the average blood osmolality measurement is changing over time; and (iii) iteratively adjust the saline fluid flow rate into the patient's body to adjust the average osmolality level closer to a known normal osmolality range.

Although infusing saline into patients has been known for decades for treating numerous conditions, utilizing controlled saline flow rates, particularly those calculated as a function of the patient's weight in kilograms, offers added functionality to a closed loop osmolality management system.

Implementing the controlled osmolality adjustment system herein may begin by programming the processor (37) to accept as an input the initial concentration of the saline being infused into the patient. For convenience, this initial concentration of hypertonic saline is referred to as "Z".

The computerized osmolality adjustment system, which operates continuously on a real time basis, iteratively receives osmolality calculations derived from the conductivity sensor (20) measurements transmitted from the catheter (10), analyzes those calculations, calculates the average osmolality level over a specified time period, and sends an output signal to the pump (40) managing fluid infusion. The fluid is typically hypertonic saline, but other medically suitable formulations would also fall within the scope of this system.

To ensure that the osmolality adjustment system described herein performs in optimal fashion, the system is capable of allowing a user to set a user specified normal osmolality range between OsmS1 and OsmSh. The minimum osmolality value, OsmS1, is also referred to as the low osmolality set point (OsmS1). The maximum osmolality set point is known as the high osmolality set point (OsmSh). This range between OsmS1 and OsmSh becomes the target that the computerized osmolality adjustment system seeks to achieve in real-time blood osmolality calculations.

As a first step toward achieving blood osmolality levels within the selected range, the fluid infusion control module calculates and stores in appropriate mathematical units (typically milliosmoles/Kg) an average blood osmolality level Ya for a specified time period. For example, the Osmolality control module may calculate and store a "current" blood Osmolality value Yt (i.e., blood osmolality calculation at time t) every 30 seconds and calculate the average osmolality level Ya over a specified time period equal to 10 minutes, or whatever time period is specified by the user. In other words, the osmolality adjustment system keeps a running average of the average blood osmolality level as measured by the catheter's conductivity sensor in the patient's bloodstream. At any given time, the controller has available to it the average blood osmolality level for the previous 10 minutes, or whatever time period has been selected by the user.

The control loop operates via pump controlling commands that determine the flow rate of fluid, such as hypertonic saline, into the patient. The pump controlling commands are divided into categories defined by osmolality control ranges along the continuum of osmolality values. The osmolality adjustment system defined herein involves the control module calculating which of the pump controlling command categories is appropriate for a particular average blood osmolality value Ya. In other words, as the conductivity sensor (20) on the catheter (10) transmits blood conductivity data back to the computer processor, the processor electronically calculates the average blood osmolality value, and assigns the average osmolality value (Ya) to a category of pump controlling commands.

The pump controlling command categories are further divided into groups determined by finite formulas based on OsmS1 and OsmSh. In one such formula, the pump controlling command categories are defined by the amount that the currently averaged blood osmolality value that has just been calculated (Ya) differs from the minimum acceptable value for blood osmolality for this patient (OsmS1). Other categories are based on the difference between Ya and OsmSh.

The next step in the algorithm implemented by the computerized system of this invention is for the control module to compare the current average osmolality measurement Ya to the prior average osmolality measurement Yb. This calculation determines the rate at which the average blood osmolality level is changing between measurements. In one embodiment of this invention, the time between osmolality measurements can be set by the user.

The system intelligently groups real-time human physiological parameters and determines the appropriate command or electronic signal that directs the pump output (i.e., the amount of hypertonic saline infused into the patient.) The osmolality adjustment system utilizes the fluid infusion control module to direct pump controlling commands for adjusting pump output. The pump controlling commands direct the pump to control the flow rates of hypertonic saline according to the category in which the most recent average osmolality calculation fits and the rate at which the osmolality level is changing.

For example, the pump controlling commands depend, at least in part, upon the following conditions: (i) the amount the average blood osmolality level (Ya) differs from a known or desirable normal range between OsmS1 and OsmSh, (ii) the amount the average blood osmolality level (Ya) has changed from a previously calculated value (Yb), and (iii) the known weight based flow rate of hypertonic saline (HTSfp) effective at the time the average osmolality calculation was calculated. Using these factors, the algorithm implemented herein determines how the hypertonic saline flow rate from the pump (40) should be adjusted to optimize the real-time blood osmolality value (Yt) for the patient at issue.

Stated differently, the algorithm of this invention utilizes a blood osmolality value calculated from blood conductivity data transmitted from a blood conductivity sensor (20) on an intravenous catheter (10) to the computerized osmolality adjustment system. In one embodiment, the computer processor (37) is programmed to receive sensor measurements at a specified time interval such as every 30 seconds. The processor (37) calculates blood osmolality from the conductivity measurements.

Once the average blood osmolality level Ya has been calculated for a selected time period and the appropriate pump controlling command set determined, the computer processor (37) turns to the steps involved in directing pump output. As part of the blood osmolality control module, the rate of fluid infusion, typically hypertonic saline infusion, is maintained in electronic format for use by the controller. A medical professional sets initial values for fluid flow rate. In the computer processor, this value would be the first value used for "previous" flow rate (HTSfp) in the calculations at hand. For example, in one embodiment, the previous (or current) flow rate for hypertonic saline is referred to herein as HTSfp. Over each osmolality measurement iteration, the processor uses the average blood osmolality value Ya, the just prior average blood Osmolality value Yb, and the most recent pump state for hypertonic saline flow rate (HTSfp) to determine how to calculate an updated pump command for the next hypertonic saline flow rate (HTSfn).

In one embodiment of this invention, the pump controlling commands set the hypertonic saline flow rate into the patient as a function of the patient's weight in kilograms (Wt). The pump controlling commands use a multiplier divided by the initial hypertonic saline concentration (Z) value set by the medical professional multiplied by the patient's weight in kilograms (Wt). The hypertonic flow rate calculations determine which of several flow rate adjustment factors can be used and converted to pump controlling command output signals. As noted above, the pump controlling commands direct the pump to change the infusion flow rate for the fluid, such as hypertonic saline, that adjusts blood osmolality.

To further assist the medical professional in monitoring a patient, the system includes software for setting low and high alarm set points for osmolality values, hypertonic saline flow, and for differentials between various blood osmolality measurements. The system also encompasses a method of calibrating the osmolality algorithm. In a preferred embodiment, the system will be calibrated at least every twelve hours. The blood for this calibration will be obtained from an arterial/venous draw, or from an indwelling arterial/venous line after the dead space of the line has been sufficiently cleared.

Another way of describing the osmolality adjustment embodiment of this invention is in terms of the computerized method of using hypertonic saline flow rate adjustment factors to optimize blood osmolality levels. As set forth herein, a computerized method of adjusting a patient's blood chemistry on a real time basis includes adjusting the patient's average blood osmolality level toward a known user specified normal range by multiplying a currently known hypertonic saline flow rate by adjustment factors. The adjusted flow rates control the amount of saline pumped into a patient's bloodstream. The method of this invention begins by continuously measuring the patient's real time blood conductivity and calculating blood osmolality from that measurement. Next, the system stores each real time blood osmolality level in a computer processor, and calculates via the computer processor an average osmolality level, Ya, over a specified time period.

The method further includes electronically assigning the average osmolality level to one of a series of osmolality control ranges. By calculating the rate at which the average osmolality level changes from one of the specified time periods to the next, and also taking into consideration the current weight based hypertonic saline flow rate (HTSfp) the method determines the fluid flow rate adjustment factor necessary to achieve an average osmolality level as specified by the bedside clinician.

The flow rate adjustment factor depends upon the state of the previous flow rate already in effect for the patient at hand. The adjustment factors are not static numbers that remain the same for every patient, but rather, the adjustment factors generally depend upon the previous weight based flow rate, the difference of the blood Osmolality measurement from a user defined range of blood Osmolality and the rate of change of the blood Osmolality over time.

Stated differently, the computerized blood osmolality adjustment system of FIG. 4 implements software to (i) determine where the patient's real-time average blood osmolality level ("Ya") lies along a continuum of blood osmolality values; (ii) track the rate at which the average blood osmolality level is changing over time; and (iii) determine the status of the currently effective, or previous, weight based hypertonic saline flow rate. By determining these parameters, the system of this invention utilizes pre-programmed fluid flow rate adjustment factors to change the flow rates for the next time period. The system continuously updates this process with new measurements from the catheter and any changes input manually by a medical professional.

The computer processor's fluid infusion control module groups the following values in determining the hypertonic saline's adjustment factors: (i) difference between the most recently calculated average blood osmolality value and the desired osmolality range; (ii) the rate at which the average blood osmolality value is changing over a specified time period; and (iii) the value of the weight based hypertonic saline flow rate. By grouping these parameters each time a new average blood osmolality level Ya is calculated, the system better selects the appropriate fluid flow rate adjustment factors.

In one embodiment, the saline adjustment factor is selected from the group consisting of 0, 0.5, 0.6, 0.7, 0.8, 0.85, 0.86, 0.87, 0.9, 0.92, 0.94, 0.95, 0.96, 0.97, 0.98, 0.99, 1.0, 1.01, 1.02, 1.03, 1.04, 1.05, 1.06, 1.07, 1.1, 1.15, 1.2, 1.24, 1.25, 1.3, 1.4 and some other value calculated as a function of the initial fluid concentration (Z) and the patient's weight. As mentioned above, the medical personnel may manually set the values of an initial saline flow rate prior to the step of continuously measuring the patient's real time blood osmolality.

Similar to the dextrose flow adjustment described above, the hypertonic saline flow is also a weight based value. In clinical practice, the nurse selects the hypertonic saline concentration on start up (e.g., 3%, 7.5%, etc.). In calculating the initial hypertonic saline infusion rate, the hypertonic concentration number (e.g. 3, 7.5) is considered a variable Z in the computerized system. In other words, the concentration number is the percent concentration value expressed as a real number. The computerized system tracks the hypertonic saline flow rate according to ranges based on a multiple of the inverse hypertonic saline concentration number and the patient's weight adjusted by a multiplier. For example, the hypertonic saline flow rate might be expressed in values similar to the following expression:

$$0.6*Wt*3/Z < HTSfp \leq 1*Wt*3/Z.$$

In the above expression, Wt=the patient's weight in kilograms, Z=the hypertonic saline concentration number, 0.6 is the weight multiplier, and 3 is the multiplier for the inverse hypertonic saline concentration number. Depending upon the osmolality trends in the patient's bloodstream and the previous hypertonic saline flow rate HTSfp, the next hypertonic saline flow rate, HTSfn, is adjusted by either a straight multiplier or if HTSfp was zero, it is begun at an amount determined by the patient's weight and a multiplier (i.e., $0.15*Wt*3/Z$).

Those having skill in the art will recognize that the invention may be embodied in many different types of computerized algorithms. Accordingly, the invention is not limited to the particular structures or software illustrated herein.

In the drawings and specification there has been set forth a preferred embodiment of the invention, and although specific terms have been employed, they are used in a generic and descriptive sense only and not for purposes of limitation, the scope of the invention being defined in the claims.

Endnotes for Above Referenced Citations:
1. Qiu W, Journal of Critical Care 2007; September 22(3): 229-235.
2. Circulation 2005; December 112 (Issue 24 Suppl): IV Part 7.5.
3. Jeremitsky E, Journal of Trauma 2003; 54(2): 312-319.
4. Gentile N, Academy of Emergency Medicine 2006; 13(2): 174-180.
5. Mullner M, Journal of Cerebral Blood Flow & Metabolism 1997; 17: 430-436.
6. Van Den Berghe G, New England Journal of Medicine 2001; 345: 1359-1367.
7. Krinsley J, Mayo Clinic Proceedings 2004; 79(8):992-1000.
8. Van Den Berghe G, New England Journal of Medicine 2006; 354: 449-461.
9. Furnary A, Endocrine Practice 2004; 10(Suppl 2): 21-31.
10. Brunkhorst F, New England Journal of Medicine 2008; 358:125-139.
11. Bhardwaj A, Current Opinion in Critical Care 2004; 10(2): 126-131.
12. Zadeh L, Information and Control 1965; 8: 338-353.
13. Van Den Berghe G, Critical Care Medicine 2006; 34(3): 612-616.
14. Verbrugge L, Anesthesiology 2007; 107: A1427.
15. Zisser H, Accuracy of a novel intravascular fluorescent continuous glucose sensor. American Diabetes Association Meeting, Jun. 5-9, 2009, New Orleans, La. Abstract 1-LB.
16. Goldberg P., Siegel M., et al. Implementation of a safe and effective insulin infusion protocol in a medical intensive care unit; Diabetes Care 2004; 27:461-467.
17. Beilman G., Joseph J., Practical Considerations for Glucose Control in Hospitalized Patients; Diabetes Technology & Therapeutics 2005; 7:823-830.
18. www.amarillomed.com/diabetes/hospform.htm Glucose Algorithm Definitions/Characteristics
1. $X_t$=Glucose value measured at time t with time measured in seconds.
2. $X_a$=Average glucose value measured over previous 10 minutes.
3. $X_a$=($X_0$+$X_{30}$+$X_{60}$+$X_{90}$+$X_{120}$+$X_{150}$+$X_{180}$+$X_{210}$+$X_{240}$+$X_{270}$+$X_{300}$+$X_{330}$+$X_{360}$+$X_{390}$+$X_{420}$+$X_{450}$+$X_{480}$+$X_{510}$+$X_{540}$+$X_{570}$)/20, wherein these are glucose values measured every 30 seconds over the previous 10 minute period.

4. For all values of Xt whereby Xt<Xa−2 standard deviations or Xt>Xa+2 standard deviations, then Xt is not included in calculation of Xa.
5. Xb=Average glucose value measured over 10 minute period immediately prior to Xa
5a. Xc=Average glucose value measured over 10 minute period immediately prior to Xb.
6. Xmin=Set point for "Low end of glucose range"
7. Xmax=Set point for "High end of glucose range"
8. INSSh=Set point for "Maximum Insulin Infusion Rate"
9. INSf=Insulin flow rate in Units/hour
10. INSfp=Insulin flow rate in Units/hour over previous 10 minutes
11. INSfn=Insulin flow rate in Units/hour over next 10 minutes
12. Dexf=Dextrose flow rate in mL/hour
13. Dexfp=Dextrose flow rate in mL/hour over previous 10 minutes
14. Dexfn=Dextrose flow rate in mL/hour over next 10 minutes
15. Wt=Patient's weight in Kilograms
16. 18 mg/dl glucose=1 mmol/L glucose
17. On start up initial insulin flow (INSf) set by nurse/physician=INSfp
18. On start up initial dextrose flow (Dexf) set by nurse/physician=Dexfp
19. Algorithm begins on start up after two average (Xa & Xb) glucose values obtained; however nurse may set INSf and Dexf which will be used as "INSfp" and "Dexfp" for the first cycle through the algorithm
20. Glucose average values calculated and algorithm adjusts Dexfn & INSfn every 10 minutes (12:00, 12:10, 12:20, etc)
21. Temp=intravascular temperature measured by thermistor
22. Nurse selects Dextrose concentration (weight/volume) on start up and in calculating initial glucose infusion rate entered Dextrose concentration number (5, 10, 12.5, 15, 20, 25) is considered variable "C".
23. If Xmin<80 mg/dL glucose then Xmin=80 mg/dL glucose
24. DexSh=Maximum dextrose rate in mL/hour set by nurse/physician
25. MIVFR=Maintenance intravenous fluid rate calculated by algorithm
26. TIVFR=Total intravenous fluid rate set by nurse/physician
27. Glucose algorithm assumes three separate infusions will be used which will consist of: 1) High dextrose solution with electrolyte composition to match that of maintenance intravenous fluid, 2) Insulin infusion with concentration of insulin infusion in "IU/mL" to be entered by nurse on start up, 3) Maintenance intravenous fluid
28. Glucose value as measured by glucose sensor on neurocatheter will be calibrated against blood glucose obtained from patient at least every 6 hours
29. Conc=concentration of insulin infusion in International Units (IU)/mL
30. When Xa<Xmin, the algorithm will measure glucose values every five minutes as follows: Xa=X0+X30+X60+X90+X120+X150+X180+X210+X240+X270/10. The resulting value for Xa will be run through the algorithm as with all values of Xa≥Xmin, utilizing the immediately prior glucose value as Xb. This process will continue until Xa≥Xmin at which point the algorithm will return to ten minute intervals of calculation/adjustment, unless otherwise directed by the secondary controller.
31. When the rules of either 218, 219 or 220 are met, a bolus dose of insulin will be infused over the subsequent 10 minutes and will be given concurrently with INSfn as calculated by the algorithm. The bolus doses of insulin may not be given more frequently than every 30 minutes. While bolus dose of insulin is infusing monitor will display "Bolus Dose of Insulin Infusing"
32. Intravenous pump will display rates of high dextrose solution, insulin infusion and maintenance intravenous solution in mL/hour. Below this display there will be an additional display that will scroll horizontally every 10 seconds the following: 1) for the high dextrose solution grams dextrose/hour will be displayed (ex. "dextrose 2 grams/hour"); 2) for the insulin infusion the insulin dose in units/Kg/hour will be displayed ("insulin 0.1 units/Kg/hour")
33. If (Xmax−Xmin)<30 mg/dL then Xmax=Xmin+30 mg/dL Glucose Alarm Events 1. "Low Glucose" alarm sounded when measured glucose is less than "Lower Glucose Alarm Limit" which may be the same or less than Xmin. This lower glucose alarm limit is set by the nurse/physician.
2. "High Glucose" alarm sounded when measured glucose is greater than "Upper Glucose Alarm Limit" which may be the same or greater than Xmax. This upper glucose alarm limit is set by the nurse/physician.
3. "Check Capillary Blood Glucose" alarm sounded whenever the "Low Glucose" or "High Glucose" alarms are sounded. In addition, if Xa−Xb<−25 mg/dL glucose or >25 mg/dL glucose activate alarm "Check Capillary Blood Glucose" & display "Time vs Glucose Value" graph
4. "Check Catheter Position" alarm sounded if Xa<40 mg/dL glucose or Temperature<32 degrees Celsius/89.6 degress Fahrenheit.
5. "Maximum Insulin Infusion Rate" alarm sounded if INSfn>INSSh.
6. If INSfn=0 units/hour and Dexfn>0 mL/hour then display "Insulin Infusion Off" & "Dextrose Infusing"
7. "Maximum Dextrose Infusion Rate" alarm sounded if (Dexfn≥DexSh).

1. If (Xa−Xmin<−10 mg/dL) and (Dexfp=0 mL/hour) and (INSfp>0 units/hour) then Dexfn=(6/X*Wt) mL/hour and INSfn=(INSfp*0.5)
2. If (Xa−Xmin<−10 mg/dL) and (Xa−Xb<−3 mg/dL) and (Dexfp>0 mL/hour) and (Dexfp<(2/X*Wt) mL/hour) and (INSfp>0 units/hour) and (INSfp<(0.05*Wt) units/hour) then Dexfn=(Dexfp*1.7) and INSfn=0 units/hour
3. If (Xa−Xmin<−10 mg/dL) and (Xa−Xb<−3 mg/dL) and (Dexfp>0 mL/hour) and (Dexfp<(2/X*Wt) mL/hour) and (INSfp>(0.05*Wt) units/hour) then Dexfn=(Dexfp*1.7) and INSfn=(INSfp*0.85)
4. If (Xa−Xmin<−10 mg/dL) and (Xa−Xb<−3 mg/dL) and (Dexfp>(2/X*Wt) mL/hour) and (Dex<(6/X*Wt) mL/hour) and (INSfp>0 units/hour) and (INSfp<(0.05*Wt) units/hour) then Dexfn=(Dexfp*1.2) and INSfn=0 units/hour
5. If (Xa−Xmin<−10 mg/dL) and (Xa−Xb<−3 mg/dL) and (Dexfp>(2/X*Wt) mL/hour) and (Dex<(6/X*Wt) mL/hour) and (INSfp≥(0.05*Wt) units/hour) then Dexfn=(Dexfp*1.2) and INSfn=(INSfp*0.85)
6. If (Xa−Xmin<−10 mg/dL) and (Xa−Xb<−3 mg/dL) and (Dexfp>(6/X*Wt) mL/hour) and (INSfp>0 units/hour) and (INSfp<(0.05*Wt) units/hour) then Dexfn=(Dexfp*1.1) and INSfn=0 units/hour
7. If (Xa−Xmin<−10 mg/dL) and (Xa−Xb<−3 mg/dL) and (Dexfp>(6/X*Wt) mL/hour) and (INSfp>(0.05*Wt) units/hour) then Dexfn=(Dexfp*1.1) and INSfn=(INSfp*0.85)
8. If (Xa−Xmin<−10 mg/dL) and (Xa−Xb≥−3 mg/dL) and (Dexfp>0 mL/hour) and (Dexfp≤(2/X*Wt) mL/hour) and (INSfp>0 units/hour) and (INSfp≤(0.02*Wt) units/hour) then Dexfn=(Dexfp*1.3) and INSfn=0 units/hour 9. If (Xa−Xmin<−10 mg/dL) and (Xa−Xb≥−3 mg/dL) and (Dexfp>0 mL/hour) and and (Dexfp≤(2/X*Wt) mL/hour) and (INSfp>(0.02*Wt) units/hour) then Dexfn=(Dexfp*1.3) and INSfn=(INSfp*0.85)

10. If (Xa−Xmin<−10 mg/dL) and (Xa−Xb≥−3 mg/dL) and (Dexfp>(2/X*Wt) mL/hour) and (Dexfp≤(6/X*Wt) mL/hour) and (INSfp>0 units/hour) and (INSfp<(0.02*Wt) units/hour) then Dexfn=(Dexfp*1.2) and INSfn=0 units/hour 11. If (Xa−Xmin<−10 mg/dL) and (Xa−Xb≥−3 mg/dL) and (Dexfp>(2/X*Wt) mL/hour) and (Dexfp≤(6/X*Wt) mL/hour) and (INSfp>(0.02*Wt) units/hour) then Dexfn=(Dexfp*1.2) and INSfn=(INSfp*0.85)

12. If (Xa−Xmin<−10 mg/dL) and (Xa−Xb≥−3 mg/dL) and (Dexfp>(6/X*Wt) mL/hour) and (INSfp>0 units/hour) and (INSfp≤(0.02*Wt) units/hour) then Dexfn=(Dexfp*1.1) and INSfn=0 units/hour 13. If (Xa−Xmin<−10 mg/dL) and (Xa−Xb≥−3 mg/dL) and (Dexfp>(6/X*Wt) mL/hour) and (INSfp>(0.02*Wt) units/hour) then Dexfn=(Dexfp*1.1) and INSfn=(INSfp*0.75)

14. If (Xa−Xmin<−10 mg/dL) and (Xa−Xb<−3 mg/dL) and (Dexfp>0 mL/hour) and (Dexfp≤(2/X*Wt) mL/hour) and (INSfp=0 units/hour) then Dexfn=(Dexfp*1.7) and INSfn=INSfp 15. If (Xa−Xmin<−10 mg/dL) and (Xa−Xb<−3 mg/dL) and (Dexfp>(2/X*Wt) mL/hour) and (Dexfp≤(6/X*Wt) mL/hour) and (INSfp=0 units/hour) then Dexfn=(Dexfp*1.4) and INSfn=INSfp 16. If (Xa−Xmin<−10 mg/dL) and (Xa−Xb<−3 mg/dL) and (Dexfp>(6/X*Wt) mL/hour) and (INSfp=0 units/hour) then Dexfn=(Dexfp*1.2) and INSfn=INSfp 17. If (Xa−Xmin<−10 mg/dL) and (Xa−Xb≥−3 mg/dL) and (Dexfp>0 mL/hour) and (Dexfp≤(2/X*Wt) mL/hour) and (INSfp=0 units/hour) then Dexfn=(Dexfp*1.5) and INSfn=INSfp 18. If (Xa−Xmin<−10 mg/dL) and (Xa−Xb≥−3 mg/dL) and (Dexfp>(2/X*Wt) mL/hour) and (Dexfp≤(6/X*Wt) mL/hour) and (INSfp=0 units/hour) then Dexfn=(Dexfp*1.3) and INSfn=INSfp 19. If (Xa−Xmin<−10 mg/dL) and (Xa−Xb≥−3 mg/dL) and (Dexfp>(6/X*Wt) mL/hour) and (INSfp=0 units/hour) then Dexfn=(Dexfp*1.2) and INSfn=INSfp 20. If (Xa−Xmin<−10 mg/dL) and (Dexfp=0 mL/hour) and (INSfp=0 units/hour) then Dexfn=(6/x*Wt) mL/hour and INSfn=INSfp 21. If (Xa−Xmin≥−10 mg/dL) and (Xa−Xmin<−5 mg/dL) and (Xa−Xb<0 mg/dL) and (Dexfp=0 mL/hour) and (INSfp>0 units/hour) and (INSfp≤(0.01*Wt) units/hour) then Dexfn=(3/X*Wt) mL/hour and INSfn=0 units/hour 22. If (Xa−Xmin≥−10 mg/dL) and (Xa−Xmin<−5 mg/dL) and (Xa−Xb<0 mg/dL) and (Dexfp=0 mL/hour) and (INSfp>(0.01*Wt) units/hour) and (INSfp<(0.1*Wt) units/hour) then Dexfn=(3/X*Wt) mL/hour and INSfn=(INSfp*0.85)

23. If (Xa−Xmin≥−10 mg/dL) and (Xa−Xmin<−5 mg/dL) and (Xa−Xb<0 mg/dL) and (Dexfp=0 mL/hour) and (INSfp>(0.1*Wt) units/hour) then Dexfn=(3/X*Wt) mL/hour and INSfn=(INSfp*0.9)

24. If (Xa−Xmin≥−10 mg/dL) and (Xa−Xmin<−5 mg/dL) and (Xa−Xb≥0 mg/dL) and (Dexfp=0 mL/hour) and (INSfp>0 units/hour) and (INSfp≤(0.01*Wt) units/hour) then Dexfn=Dexfp and INSfn=0 units/hour 25. If (Xa−Xmin≥−10 mg/dL) and (Xa−Xmin<−5 mg/dL) and (Xa−Xb≥0 mg/dL) and (Dexfp=0 mL/hour) and (IN-Sfp>(0.01*Wt) units/hour) and (INSfp<(0.1*Wt) units/hour) then Dexfn=Dexfp and INSfn=(INSfp*0.9)

26. If (Xa−Xmin≥−10 mg/dL) and (Xa−Xmin<−5 mg/dL) and (Xa−Xb≥0 mg/dL) and (Dexfp=0 mL/hour) and (INSfp>(0.1*Wt) units/hour) then Dexfn=Dexfp and INSfn=(INSfp*0.85)

27. If (Xa−Xmin≥−10 mg/dL) and (Xa−Xmin<−5 mg/dL) and (Xa−Xb<−3 mg/dL) and (Dexfp>0 mL/hour) and (Dexfp≤(2/X*Wt) mL/hour) and (INSfp>0 units/hour) and (INSfp≤(0.01*Wt) units/hour) then Dexfn=(Dexfp*1.5) and INSfn=0 units/hour 28. If (Xa−Xmin≥−10 mg/dL) and (Xa−Xmin<−5 mg/dL) and (Xa−Xb<−3 mg/dL) and (Dexfp>0 mL/hour) and (Dexfp≤(2/X*Wt) mL/hour) and (INSfp>(0.01*Wt) units/hour) and (INSfp≤(0.1*Wt) units/hour) then Dexfn=(Dexfp*1.5) and INSfn=(INSfp*0.8)

29. If (Xa−Xmin≥−10 mg/dL) and (Xa−Xmin<−5 mg/dL) and (Xa−Xb<−3 mg/dL) and (Dexfp>0 mL/hour) and (Dexfp≤(2/X*Wt) mL/hour) and (INSfp>(0.1*Wt) units/hour) then Dexfn=(Dexfp*1.5) and INSfn=(INSfp*0.9)

30. If (Xa−Xmin≥−10 mg/dL) and (Xa−Xmin<−5 mg/dL) and (Xa−Xb<−3 mg/dL) and (Dexfp>(2/X*Wt) mL/hour) and (Dexfp≤(6/X*Wt) mL/hour) and (INSfp>0 units/hour) and (INSfp≤(0.01*Wt) units/hour) then Dexfn=(Dexfp*1.3) and INSfn=0 units/hour 31. If (Xa−Xmin.≥−10 mg/dL) and (Xa−Xmin<−5 mg/dL) and (Xa−Xb<−3 mg/dL) and (Dexfp>(2/X*Wt) mL/hour) And (Dexfp≤(6/X*Wt) mL/hour) and (INSfp>(0.01*Wt) units/hour) and (INSfp≤(0.1*Wt units/hour) then Dexfn=(Dexfp*1.3) and INSfn=(INSfp*0.8)

32. If (Xa−Xmin≥−10 mg/dL) and (Xa−Xmin<−5 mg/dL) and (Xa−Xb<−3 mg/dL) and (Dexfp>(2/X*Wt) mL/hour) and (Dexfp≤(6/X*Wt) mL/hour) and (INSfp>(0.1*Wt) units/hour) then Dexfn=(Dexfp*1.3) and INSfn=(INSfp*0.9)

33. If (Xa−Xmin≥−10 mg/dL) and (Xa−Xmin<−5 mg/dL) and (Xa−Xb<−3 mg/dL) and (Dexfp>(6/X*Wt) mL/hour) and (INSfp>0 units/hour) and (INSfp≤(0.01*Wt) units/hour) then Dexfn=(Dexfp*1.2) and INSfn=0 units/hour 34. If (Xa−Xmin≥−10 mg/dL) and (Xa−Xmin<−5 mg/dL) and (Xa−Xb<−3 mg/dL) and (Dexfp>(6/X*Wt) mL/hour) and (INSfp>(0.01*Wt) units/hour) and (INSfp≤(0.1*Wt) units/hour) then Dexfn=(Dexfp*1.1) and INSfn=(INSfp*0.8)

35. If (Xa−Xmin≥−10 mg/dL) and (Xa−Xmin<−5 mg/dL) and (Xa−Xb<−3 mg/dL) and (Dexfp>(6/X*Wt) mL/hour) and (INSfp>(0.1*Wt) units/hour) then Dexfn=(Dexfp*1.1) and INSfn=(INSfp*0.9)

36. If (Xa−Xmin≥−10 mg/dL) and (Xa−Xmin<−5 mg/dL) and (Xa−Xb≥−3 mg/dL) and (Xa−Xb≤1 mg/dL) and (Dexfp>0 mL/hour) and (INSfp>0 units/hour) and (INSfp<(0.01*Wt) units/hour) then Dexfn=(Dexfp*1.1) and INSfn=0 units/hour 37. If (Xa−Xmin≥−10 mg/dL) and (Xa−Xmin<−5 mg/dL) and (Xa−Xb≥−3 mg/dL) and (Xa−Xb≤1 mg/dL) and (Dexfp>0 mL/hour) and (INSfp>(0.01*Wt) units/hour) and (INSfp≤(0.1*Wt) units/hour) then Dexfn=(Dexfp*1.1) and INSfn=(INSfp*0.85)

38. If (Xa−Xmin≥−10 mg/dL) and (Xa−Xmin<−5 mg/dL) and (Xa−Xb≥−3 mg/dL) and (Xa−Xb≤1 mg/dL) and (Dexfp>0 mL/hour) and (INSfp>(0.1*Wt) units/hour) then Dexfn=(Dexfp*1.1) and INSfn=(INSfp*0.95)

39. If (Xa−Xmin≥−10 mg/dL) and (Xa−Xmin<−5 mg/dL) and (Xa−Xb>1 mg/dL) and (Dexfp>0 mL/hour) and (INSfp>0 units/hour) then Dexfn=(Dexfp*1.1) and INSfn=(INSfp*0.95)

40. If (Xa−Xmin≥−10 mg/dL) and (Xa−Xmin<−5 mg/dL) and (Xa−Xb<−1 mg/dL) and (Dexfp>0 mL/hour) and (Dexfp≤(2/X*Wt) mL/hour) and (INSfp=0 units/hour) then Dexfn=(Dexfp*1.5) and INSfn=0 units/hour 41. If (Xa−Xmin≥−10 mg/dL) and (Xa−Xmin<−5 mg/dL) and (Xa−Xb<−1 mg/dL) and (Dexfp>(2/X*Wt) mL/hour) and (Dexfp≤6/X*Wt) mL/hour) and (INSfp=0 units/hour) then Dexfn=(Dexfp*1.3) mL/hour and INSfn=0 units/hour 42. If (Xa−Xmin≥−10 mg/dL) and (Xa−Xmin<−5 mg/dL) and (Xa−Xb<−1 mg/dL) and (Dexfp>(6/X*Wt) mL/hour) and (INSfp=0 units/hour) then Dexfn=(Dexfp*1.1) mL/hour and INSfn=0 units/hour 43. If (Xa−Xmin≥−10 mg/dL) and (Xa−Xmin<−5 mg/dL) and (Xa−Xb≥−1 mg/dL) and (Dexfp>0 mL/hour) and (INSfp=0 units/hour) then Dexfn=(Dexfp*1.1) mL/hour and INSfn=0 units/hour 44. If (Xa−Xmin≥−10 mg/dL) and (Xa−Xmin<−5 mg/dL) and (Xa−Xb<−1 mg/dL) and (Dexfp=0 mL/hour) and (INSfp=0 units/hour) then Dexfn=(3/X*Wt) mL/hour and INSfn=INSfp 45. If (Xa−Xmin≥−10 mg/dL) and (Xa−Xmin<−5 mg/dL) and (Xa−Xb≥−1 mg/dL) and (Dexfp=0 mL/hour) and (INSfp=0 units/hour) then Dexfn=(2/X*Wt) mL/hour and INSfn=INSfp 46. If (Xa−Xmin>−5 mg/dL) and (Xa<Xmin mg/dL) and (Xa−Xb<−2 mg/dL) and (Dexfp=0 mL/hour) and (INSfp>0 units/hour) and (INSfp≤(0.01*Wt) units/hour) then Dexfn=(2/X*Wt) mL/hour and INSfn=0 units/hour 47. If (Xa−Xmin≥−5 mg/dL) and (Xa<Xmin mg/dL) and (Xa−Xb<−2 mg/dL) and (Dexfp=0 mL/hour) and (INSfp>(0.01*Wt) units/hour) and (INSfp≤(0.1*Wt) units/hour) then Dexfn=(2/X*Wt) mL/hour and INSfn=(INSfp*0.8)

48. If (Xa−Xmin≥−5 mg/dL) and (Xa<Xmin mg/dL) and (Xa−Xb<−2 mg/dL) and (Dexfp=0 mL/hour) and (INSfp>(0.1*Wt) units/hour) then Dexfn=(2/X*Wt) mL/hour and INSfn=(INSfp*0.9)

49. If (Xa−Xmin≥−5 mg/dL) and (Xa<Xmin mg/dL) and (Xa−Xb≥−2 mg/dL) and (Dexfp=0 mL/hour) and (INSfp>0 units/hour) and (INSfp≤(0.01*Wt) units/hour) then Dexfn=Dexfp and INSfn=0 units/hour 50. If (Xa−Xmin≥−5 mg/dL) and (Xa<Xmin mg/dL) and (Xa−Xb>−2 mg/dL) and (Dexfp=0 mL/hour) and (INSfp>(0.01*Wt) units/hour) and (INSfp≤(0.1*Wt) units/hour) then Dexfn=Dexfp and INSfn=(INSfp*0.85)

51. If (Xa−Xmin≥−5 mg/dL) and (Xa<Xmin mg/dL) and (Xa−Xb>−2 mg/dL) and (Dexfp=0 mL/hour) and (INSfp>(0.1*Wt) units/hour) then Dexfn=Dexfp and INSfn=(INSfp*0.95)

52. If (Xa−Xmin≥−5 mg/dL) and (Xa<Xmin mg/dL) and (Xa−Xb<−2 mg/dL) and (Dexfp>0 mL/hour) and (Dexfp≤(2/X*Wt) mL/hour) and (INSfp>0 units/hour) and (INSfp≤(0.01*Wt) units/hour) then Dexfn=(Dexfp*1.5) and INSfn=0 units/hour 53. If (Xa−Xmin≥−5 mg/dL) and (Xa<Xmin mg/dL) and (Xa−Xb<−2 mg/dL) and (Dexfp>0 mL/hour) and (Dexfp≤(2/X*Wt) mL/hour) and (INSfp>(0.01*Wt) units/hour) and (INSfp≤(0.1*Wt) units/hour) then Dexfn=(Dexfp*1.5) and INSfn=(INSfp*0.85)

54. If (Xa−Xmin≥−5 mg/dL) and (Xa<Xmin mg/dL) and (Xa−Xb<−2 mg/dL) and (Dexfp>0 mL/hour) and (Dexfp≤(2/X*Wt) mL/hour) and (INSfp>(0.1*Wt) units/hour) then Dexfn=(Dexfp*1.5) and INSfn=(INSfp*0.9)

55. If (Xa−Xmin≥−5 mg/dL) and (Xa<Xmin mg/dL) and (Xa−Xb<−2 mg/dL) and (Dexfp>(2/X*Wt) mL/hour) and (Dexfp≤6/X*Wt) mL/hour) and (INSfp>0 units/hour) and (INSfp≤(0.01*Wt) units/hour) then Dexfn=(Dexfp*1.25) mL/hour and INSfn=0 units/hour 56. If (Xa−Xmin≥−5 mg/dL) and (Xa<Xmin mg/dL) and (Xa−Xb<−2 mg/dL) and (Dexfp>(2/X*Wt) mL/hour) and (Dexfp≤6/X*Wt) mL/hour) and (INSfp>(0.01*Wt) units/hour) and (INSfp≤(0.1*Wt) units/hour) then Dexfn=(Dexfp*1.25) mL/hour and INSfn=(INSfp*0.85)

57. If (Xa−Xmin≥−5 mg/dL) and (Xa<Xmin mg/dL) and (Xa−Xb<−2 mg/dL) and (Dexfp>(2/X*Wt) mL/hour) and (Dexfp≤6/X*Wt) mL/hour) and (INSfp>(0.1*Wt) units/hour) then Dexfn=(Dexfp*1.25) mL/hour and INSfn=(INSp*0.9)

58. If (Xa−Xmin≥−5 mg/dL) and (Xa<Xmin mg/dL) and (Xa−Xb<−2 mg/dL) and (Dexfp>(6/X*Wt) mL/hour) and (INSfp>0 units/hour) and (INSfp<(0.01*Wt) units/hour) then Dexfn=(Dexfp*1.1) mL/hour and INSfn=0 units/hour 59. If (Xa−Xmin≥−5 mg/dL) and (Xa<Xmin mg/dL) and (Xa−Xb<−2 mg/dL) and (Dexfp>(6/X*Wt) mL/hour) and (INSfp>(0.01*Wt) units/hour) and (INSfp≤(0.1*Wt) units/hour) then Dexfn=(Dexfp*1.1) mL/hour and INSfn=(INSfp*0.85)

60. If (Xa−Xmin≥−5 mg/dL) and (Xa<Xmin mg/dL) and (Xa−Xb<−2 mg/dL) and (Dexfp>(6/X*Wt) mL/hour) and (INSfp>(0.1*Wt) units/hour) then Dexfn=(Dexfp*1.1) mL/hour and INSfn=(INSfp*0.9)

61. If (Xa−Xmin≥−5 mg/dL) and (Xa<Xmin mg/dL) and (Xa−Xb≥−2 mg/dL) and (Dexfp>0 mL/hour) and (INSfp>0 units/hour) and (INSfp≤(0.01*Wt) units/hour) then Dexfn=Dexfp and INSfn=0 units/hour 62. If (Xa−Xmin≥−5 mg/dL) and (Xa<Xmin mg/dL) and (Xa−Xb≥−2 mg/dL) and (Dexfp>0 mL/hour) and (INSfp>(0.01*Wt) units/hour) then Dexfn=Dexfp and INSfn=(INSfp*0.95)

63. If (Xa−Xmin≥−5 mg/dL) and (Xa<Xmin mg/dL) and (Xa−Xb<−1 mg/dL) and (Dexfp>0 mL/hour) and (Dexfp≤(2/X*Wt) mL/hour) and (INSfp=0 units/hour) then Dexfn=(Dexfp 1.5) and INSfn=INSfp 64. If (Xa−Xmin≥−5 mg/dL) and (Xa<Xmin mg/dL) and (Xa−Xb<−1 mg/dL) and (Dexfp>(2/X*Wt) mL/hour) and (Dexfp≤(6/X*Wt) mL/hour) and (INSfp=0 units/hour) then Dexfn=(Dexfp*1.25) and INSfn=INSfp 65. If (Xa−Xmin≥−5 mg/dL) and (Xa<Xmin mg/dL) and (Xa−Xb<−1 mg/dL) and (Dexfp>(6/X*Wt) mL/hour) and (INSfp=0 units/hour) then Dexfn=(Dexfp*1.1) and INSfn=INSfp 66. If (Xa−Xmin≥−5 mg/dL) and (Xa<Xmin mg/dL) and (Xa−Xb≥−1 mg/dL) and (Dexfp>0 mL/hour) and (INSfp=0 units/hour) then Dexfn=Dexfp and INSfn=INSfp 67. If (Xa−Xmin≥−5 mg/dL) and (Xa<Xmin mg/dL) and (Xa−Xb<−1 mg/dL) and (Dexfp=0 mL/hour) and (INSfp=0 units/hour) then Dexfn=(2/X*Wt) mL/hour and INSfn=INSfp 68. If (Xa−Xmin≥−5 mg/dL) and (Xa<Xmin mg/dL) and (Xa−Xb≥−1 mg/dL) and (Dexfp=0 mL/hour) and (INSfp=0 units/hour) then Dexfn=Dexfp and INSfn=INSfp 69. If (Xa≥Xmin mg/dL) and (Xa<(Xmin+(Xmax−Xmin)/3) mg/dL) and (Xa−Xb≤−2 mg/dL) and (Dexfp=0 mL/hour) and (INSfp>0 units/hour) and (INSfp<(0.01*Wt) units/hour) then Dexfn=Dexfp and INSfn=0 units/hour 70. If (Xa≥Xmin mg/dL) and (Xa<(Xmin+(Xmax−Xmin)/3) mg/dL) and (Xa−Xb≤−2 mg/dL) and (Dexfp=0 mL/hour) and (INSfp>(0.01*Wt) units/hour) and (INSfp≤(0.1*Wt) units/hour) then Dexfn=Dexfp and INSfn=(INSfp*0.85)

71. If (Xa>Xmin mg/dL) and (Xa<(Xmin+(Xmax−Xmin)/3) mg/dL) and (Xa−Xb≤−2 mg/dL) and (Dexfp=0 mL/hour) and (INSfp>(0.1*Wt) units/hour) then Dexfn=Dexfp and INSfn=(INSfp*0.9)

72. If (Xa≥Xmin mg/dL) and (Xa<(Xmin+(Xmax−Xmin)/3) mg/dL) and (Xa−Xb>−2 mg/dL) and (Xa−Xb≤3 mg/dL)

and (Dexfp=0 mL/hour) and (INSfp>0 units/hour) then Dexfn=Dexfp and INSfn=INSfp

73. If (Xa≥Xmin mg/dL) and (Xa<(Xmin+(Xmax−Xmin)/3) mg/dL) and (Xa−Xb>3 mg/dL) and (Dexfp=0 mL/hour) and (INSfp>0 units/hour) then Dexfn=Dexfp and INSfn=(INSfp*1.05)

74. If (Xa≥Xmin mg/dL) and (Xa<(Xmin+(Xmax−Xmin)/3) mg/dL) and (Xa−Xb≤−2 mg/dL) and (Dexfp>0 mL/hour) and (Dexfp≤(2/X*Wt) mL/hour) and (INSfp>0 units/hour) and (INSfp≤(0.01*Wt) units/hour) then Dexfn=(Dexfp*1.5) and INSfn=0 units/hour 75. If (Xa≥Xmin mg/dL) and (Xa<(Xmin+(Xmax−Xmin)/3) mg/dL) and (Xa−Xb≤−2 mg/dL) and (Dexfp>0 mL/hour) and (Dexfp≤(2/X*Wt) mL/hour) and (INSfp>(0.01*Wt) units/hour) and (INSfp≤(0.1*Wt) units/hour) then Dexfn=(Dexfp*1.5) and INSfn=(INSfp*0.85)

76. If (Xa≥Xmin mg/dL) and (Xa<(Xmin+(Xmax−Xmin)/3) mg/dL) and (Xa−Xb≤−2 mg/dL) and (Dexfp>0 mL/hour) and (Dexfp≤(2/X*Wt) mL/hour) and (INSfp>(0.1*Wt) units/hour) then Dexfn=(Dexfp 1.5) and INSfn=(INSfp*0.9)

77. If (Xa≥Xmin mg/dL) and (Xa<(Xmin+(Xmax−Xmin)/3) mg/dL) and (Xa−Xb≤−2 mg/dL) and (Dexfp>(2/X*Wt) mL/hour) and (Dexfp≤(6/X*Wt) mL/hour) and (INSfp>0 units/hour) and (INSfp≤(0.01*Wt) units/hour) then Dexfn=(Dexfp*1.25) and INSfn=0 units/hour 78. If (Xa≥Xmin mg/dL) and (Xa<(Xmin+(Xmax−Xmin)/3) mg/dL) and (Xa−Xb≤−2 mg/dL) and (Dexfp>(2/X*Wt) mL/hour) and (Dexfp≤(6/X*Wt) mL/hour) and (INSfp>(0.01*Wt) units/hour) and (INSfp≤(0.1*Wt) units/hour) then Dexfn=(Dexfp*1.25) and INSfn=(INSfp*0.85)

79. If (Xa≥Xmin mg/dL) and (Xa<(Xmin+(Xmax−Xmin)/3) mg/dL) and (Xa−Xb≤−2 mg/dL) and (Dexfp>(2/X*Wt) mL/hour) and (Dexfp<(6/X*Wt) mL/hour) and (INSfp>(0.1*Wt) units/hour) then Dexfn=(Dexfp*1.25) and INSfn=(INSfp*0.9)

80. If (Xa≥Xmin mg/dL) and (Xa<(Xmin+(Xmax−Xmin)/3) mg/dL) and (Xa−Xb≤−2 mg/dL) and (Dexfp>(6/X*Wt) mL/hour) and (INSfp>0 units/hour) and (INSfp≤(0.01*Wt) units/hour) then Dexfn=(Dexfp*1.1) and INSfn=0 units/hour 81. If (Xa≥Xmin mg/dL) and (Xa<(Xmin+(Xmax−Xmin)/3) mg/dL) and (Xa−Xb≤−2 mg/dL) and (Dexfp>(6/X*Wt) mL/hour) and (INSfp>(0.01*Wt) units/hour) and (INSfp≤(0.1*Wt) units/hour) then Dexfn=(Dexfp*1.1) and INSfn=(INSfp 0.85)

82. If (Xa≥Xmin mg/dL) and (Xa<(Xmin+(Xmax−Xmin)/3) mg/dL) and (Xa−Xb≤−2 mg/dL) and (Dexfp>(6/X*Wt) mL/hour) and (INSfp>(0.1*Wt) units/hour) then Dexfn=(Dexfp*1.1) and INSfn=(INSfp*0.9)

83. If (Xa≥Xmin mg/dL) and (Xa<(Xmin+(Xmax−Xmin)/3) mg/dL) and (Xa−Xb>−2 mg/dL) and (Xa−Xb≤3 mg/dL) and (Dexfp>0 mL/hour) and (INSfp>0 units/hour) then Dexfn=Dexfp and INSfn=INSfp 84. If (Xa>Xmin mg/dL) and (Xa<(Xmin+(Xmax−Xmin)/3) mg/dL) and (Xa−Xb>3 mg/dL) and (Dexfp>0 mL/hour) and (Dexfp<(1/X*Wt) mL/hour) and (INSfp>0 units/hour) then Dexfn=0 mL/hour and INSfn=(INSfp*1.05)

85. If (Xa≥Xmin mg/dL) and (Xa<(Xmin+(Xmax−Xmin)/3) mg/dL) and (Xa−Xb>3 mg/dL) and (Dexfp>(1/X*Wt) mL/hour) and (INSfp>0 units/hour) then Dexfn=(Dexfp*0.95) and INSfn=(INSfp*1.05)

86. If (Xa≥Xmin mg/dL) and (Xa<(Xmin+(Xmax−Xmin)/3) mg/dL) and (Xa−Xb≤−2 mg/dL) and (Dexfp>0 mL/hour) and (Dexfp≤(2/X*Wt) mL/hour) and (INSfp=0 units/hour) then Dexfn=(Dexfp*1.5) and INSfn=INSfp 87. If (Xa≥Xmin mg/dL) and (Xa<(Xmin+(Xmax−Xmin)/3) mg/dL) and (Xa−Xb≤−2 mg/dL) and (Dexfp>(2/X*Wt) mL/hour) and (Dexfp≤(6/X*Wt) mL/hour) and (INSfp=0 units/hour) then Dexfn=(Dexfp*1.25) and INSfn=INSfp 88. If (Xa≥Xmin mg/dL) and (Xa<(Xmin+(Xmax−Xmin)/3) mg/dL) and (Xa−Xb≤−2 mg/dL) and (Dexfp>(6/X*Wt) mL/hour) and (INSfp=0 units/hour) then Dexfn=(Dexfp*1.1) and INSfn=INSfp 89. If (Xa≥Xmin mg/dL) and (Xa<(Xmin+(Xmax−Xmin)/3) mg/dL) and (Xa−Xb>−2 mg/dL) and (Xa−Xb≤3 mg/dL) and (Dexfp>0 mL/hour) and (INSfp=0 units/hour) then Dexfn=Dexfp and INSfn=INSfp 90. If (Xa≥Xmin mg/dL) and (Xa<(Xmin+(Xmax−Xmin)/3) mg/dL) and (Xa−Xb>3 mg/dL) and (Dexfp>0 mL/hour) and (Dexfp≤(1/X*Wt) mL/hour) and (INSfp=0 units/hour) then Dexfn=0 mL/hour and INSfn=(0.01*Wt) units/hour 91. If (Xa≥Xmin mg/dL) and (Xa<(Xmin+(Xmax−Xmin)/3) mg/dL) and (Xa−Xb>3 mg/dL) and (Dexfp>(1/X*Wt) mL/hour) and (INSfp=0 units/hour) then Dexfn=(Dexfp*0.95) and INSfn=(0.01*Wt) units/hour 92. If (Xa≥Xmin mg/dL) and (Xa<(Xmin+(Xmax−Xmin)/3) mg/dL) and (Xa−Xb≤−3 mg/dL) and (Dexfp=0 mL/hour) and (INSfp=0 units/hour) then Dexfn=(2/X*Wt) mL/hour and INSfn=INSfp 93. If (Xa≥Xmin mg/dL) and (Xa<(Xmin+(Xmax−Xmin)/3) mg/dL) and (Xa−Xb>−3 mg/dL) and (Xa−Xb≤3 mg/dL) and (Dexfp=0 mL/hour) and (INSfp=0 units/hour) then Dexfn=Dexfp and INSfn=INSfp 94. If (Xa≥Xmin mg/dL) and (Xa<(Xmin+(Xmax−Xmin)/3) mg/dL) and (Xa−Xb>3 mg/dL) and (Dexfp=0 mL/hour) and (INSfp=0 units/hour) then Dexfn=Dexfp and INSfn=(0.01*Wt) units/hour 95. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp=0 mL/hour) and (INSfp>0 units/hour) and (INSfp≤(0.01*Wt) units/hour) then Dexfn=Dexfp and INSfn=0 units/hour 96. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp=0 mL/hour) and (INSfp>(0.01*Wt) units/hour) and (INSfp≤0.1*Wt) units/hour) then Dexfn=Dexfp and INSfn=(INSfp*0.9)

97. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp=0 mL/hour) and (INSfp>(0.1*Wt) units/hour) then Dexfn=Dexfp and INSfn=(INSfp*0.95)

98. If (Xa≥(Xmin+(Xmax−Xmin)/3) mg/dL) and (Xa<(Xmin+2(Xmax−Xmin)/3) mg/dL) and (Xa−Xb>−3 mg/dL) and (Xa−Xb≤3 mg/dL) and (Dexfp=0 mL/hour) and (INSfp>0 units/hour) then Dexfn=Dexfp and INSfn=INSfp 99. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp=0 mL/hour) and (INSfp>0 units/hour) and (INSfp<(0.01*Wt) units/hour) then Dexfn=Dexfp and INSfn=(INSfp 1.5)

100. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp=0 mL/hour) and (INSfp>(0.01*Wt) units/hour) and (INSfp≤(0.1*Wt) units/hour) then Dexfn=Dexfp and INSfn=(INSfp*1.15)

101. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp=0 mL/hour) and (INSfp>(0.1*Wt) units/hour) then Dexfn=Dexfp and INSfn=(INSfp*1.1)

102. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp>0 mL/hour) and (INSfp>0 units/hour) and (INSfp≤(0.01*Wt) units/hour) then Dexfn=Dexfp and INSfn=0 units/hour 103. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp>0 mL/hour) and (INSfp>(0.01*Wt) units/hour) and (INSfp≤(0.1*Wt) units/hour) then Dexfn=Dexfp and INSfn=(INSfp*0.9)

104. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp>0 mL/hour) and (INSfp>(0.1*Wt) units/hour) then Dexfn=Dexfp and INSfn=(INSfp*0.95)

105. If (Xa≥(Xmin+(Xmax−Xmin)/3) mg/dL) and (Xa<(Xmin+2(Xmax−Xmin)/3) mg/dL) and (Xa−Xb>−3 mg/dL) and (Xa−Xb≤3 mg/dL) and (Dexfp>0 mL/hour) and (INSfp>0 units/hour) then Dexfn=Dexfp and INSfn=INSfp 106. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>0 mL/hour) and (Dexfp≤(1/X*Wt) mL/hour) and (INSfp>0 units/hour) and (INSfp≤(0.01*Wt) units/hour) then Dexfn=0 mL/hour and INSfn=(INSfp*1.5)

107. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>0 mL/hour) and (Dexfp≤(1/X*Wt) mL/hour) and (INSfp>(0.01*Wt) units/hour) and (INSfp≤(0.1*Wt) units/hour) then Dexfn=0 mL/hour and INSfn=(INSfp*1.15)

108. Lf (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>0 mL/hour) and (Dexfp≤(1/X*Wt) mL/hour) and (INSfp>(0.1*Wt) units/hour) then Dexfn=0 mL/hour and INSfn=(INSfp*1.05)

109. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>(1/X*Wt) mL/hour) and (Dexfp≤(6/X*Wt) mL/hour) and (INSfp>0 units/hour) and (INSfp<(0.01*Wt) units/hour) then Dexfn=(Dexfp*0.85) and INSfn=(INSfp*1.5)

110. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>(1/X*Wt) mL/hour) and (Dexfp≤(6/X*Wt) mL/hour) and (INSfp>(0.01*Wt) units/hour) and (INSfp≤(0.1*Wt) units/hour) then Dexfn=(Dexfp*0.85) and INSfn=(INSfp*1.15)

111. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>(1/X*Wt) mL/hour) and (Dexfp≤(6/X*Wt) mL/hour) and (INSfp>(0.1*Wt) units/hour) then Dexfn=(Dexfp*0.85) and INSfn=(INSfp*1.05)

112. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>(6/X*Wt) mL/hour) and (INSfp>0 units/hour) and (INSfp≤(0.01*Wt) units/hour) then Dexfn=(Dexfp*0.9) and INSfn=(INSfp*1.5)

113. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>(6/X*Wt) mL/hour) and (INSfp>(0.01*Wt) units/hour) and (INSfp≤0.1*Wt) units/hour) then Dexfn=(Dexfp*0.9) and INSfn=(INSfp*1.15)

114. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>(6/X*Wt) mL/hour) and (INSfp>(0.1*Wt) units/hour) then Dexfn=(Dexfp*0.9) and INSfn=(INSfp*1.05)

115. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp>0 mL/hour) and (Dexfp≤(1/X*Wt) mL/hour) and (INSfp=0 units/hour) then Dexfn=(Dexfp*1.3) and INSfn=INSfp 116. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp>(1/X*Wt) mL/hour) and (Dexfp≤(6/X*Wt) mL/hour) and (INSfp=0 units/hour) then Dexfn=(Dexfp*1.1) and INSfn=INSfp 117. If (Xa≥(Xmin+(Xmax−Xmin)/3) mg/dL) and (Xa<(Xmin+2(Xmax−Xmin)/3) mg/dL) and (Xa−Xb≤−3 mg/dL) and (Dexfp>(6/X*Wt) mL/hour) and (INSfp=0 units/hour) then Dexfn=(Dexfp*1.05) and INSfn=INSfp 118. If (Xa≥(Xmin+(Xmax−Xmin)/3) mg/dL) and (Xa<(Xmin+2(Xmax−Xmin)/3) mg/dL) and (Xa−Xb>−3 mg/dL) and (Xa−Xb≤3 mg/dL) and (Dexfp>0 mL/hour) and (INSfp=0 units/hour) then Dexfn=Dexfp and INSfn=INSfp 119. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>0 mL/hour) and (Dexfp≤(1/X*Wt) mL/hour) and (INSfp=0 units/hour) then Dexfn=0 mL/hour and INSfn=(0.02*Wt) units/hour 120. If (Xa≥(Xmin+(Xmax−Xmin)/3) mg/dL) and (Xa<(Xmin+2(Xmax−Xmin)/3) mg/dL) and (Xa−Xb>3 mg/dL) and (Dexfp>(1/X*Wt) mL/hour) and (INSfp=0 units/hour) then Dexfn=(Dexfp*0.9) and INSfn=(0.02*Wt) units/hour 121. If (Xa≥(Xmin+(Xmax−Xmin)/3) mg/dL) and (Xa<(Xmin+2(Xmax−Xmin)/3) mg/dL) and (Xa−Xb≤2 mg/dL) and (Dexfp=0 mL/hour) and (INSfp=0 units/hour) then Dexfn=Dexfp and INSfn=INSfp 122. If (Xa≥(Xmin+(Xmax−Xmin)/3) mg/dL) and (Xa<(Xmin+2(Xmax−Xmin)/3) mg/dL) and (Xa−Xb>2 mg/dL) and (Dexfp=0 mL/hour) and (INSfp=0 units/hour) then Dexfn=Dexfp and INSfn=(0.02*Wt) units/hour 123. If (Xa≥(Xmin+2(Xmax−Xmin)/3) mg/dL) and (Xa<Xmax mg/dL) and (Xa−Xb≤−5 mg/dL) and (Dexfp=0 mL/hour) and (INSfp>0 units/hour) and (INSfp≤(0.01*Wt) units/hour) then Dexfn=Dexfp and INSfn=0 units/hour 124. If (Xa≥(Xmin+2(Xmax−Xmin)/3) mg/dL) and (Xa<Xmax mg/dL) and (Xa−Xb≤−5 mg/dL) and (Dexfp=0 mL/hour) and (INSfp>(0.01*Wt) units/hour) and (INSfp≤(0.1*Wt) units/hour) then Dexfn=Dexfp and INSfn=(INSfp*0.85)

125. If (Xa≥(Xmin+2(Xmax−Xmin)/3) mg/dL) and (Xa<Xmax mg/dL) and (Xa−Xb≤−5 mg/dL) and (Dexfp=0 mL/hour) and (INSfp>(0.1*Wt) units/hour) then Dexfn=Dexfp and INSfn=(INSfp*0.9)

126. If (Xa≥(Xmin+2(Xmax−Xmin)/3) mg/dL) and (Xa<Xmax mg/dL) and (Xa−Xb≥−5 mg/dL) and (Xa−Xb≤0 mg/dL) and (Dexfp=0 mL/hour) and (INSfp>0 units/hour) then Dexfn=Dexfp and INSfn=INSfp 127. If (Xa≥(Xmin+2(Xmax−Xmin)/3) mg/dL) and (Xa<Xmax mg/dL) and (Xa−Xb>0 mg/dL) and (Dexfp=0 mL/hour) and (INSfp>0 units/hour) and (INSfp≤(0.02*Wt) units/hour) then Dexfn=Dexfp and INSfn=(INSfp*1.5)

128. If (Xa≥(Xmin+2(Xmax−Xmin)/3) mg/dL) and (Xa<Xmax mg/dL) and (Xa−Xb>0 mg/dL) and (Dexfp=0 mL/hour) and (INSfp>(0.02*Wt) units/hour) and (INSfp≤(0.1*Wt) units/hour) then Dexfn=Dexfp and INSfn=(INSfp*1.15)

129. If (Xa≥(Xmin+2(Xmax−Xmin)/3) mg/dL) and (Xa<Xmax mg/dL) and (Xa−Xb>0 mg/dL) and (Dexfp=0 mL/hour) and (INSfp>(0.1*Wt) units/hour) then Dexfn=Dexfp and INSfn=(INSfp*1.05)

130. If (Xa≥(Xmin+2(Xmax−Xmin)/3) mg/dL) and (Xa<Xmax mg/dL) and (Xa−Xb≤−5 mg/dL) and (Dexfp>0 mL/hour) and (INSfp>0 units/hour) and (INSfp≤(0.01*Wt) units/hour) then Dexfn=Dexfp and INSfn=0 units/hour 131. If (Xa≥(Xmin+2(Xmax−Xmin)/3) mg/dL) and (Xa<Xmax mg/dL) and (Xa−Xb≤−5 mg/dL) and (Dexfp>0 mL/hour) and (INSfp>(0.01*Wt) units/hour) then Dexfn=Dexfp and INSfn=(INSfp*0.95)

132. If (Xa≥(Xmin+2(Xmax−Xmin)/3) mg/dL) and (Xa<Xmax mg/dL) and (Xa−Xb≥−5 mg/dL) and (Xa−Xb≤0 mg/dL) and (Dexfp>0 mL/hour) and (INSfp>0 units/hour) then Dexfn=Dexfp and INSfn=INSfp 133. If (Xa≥(Xmin+2(Xmax−Xmin)/3) mg/dL) and (Xa<Xmax mg/dL) and (Xa−Xb>0 mg/dL) and (Dexfp>0 mL/hour) and (Dexfp≤(1/X*Wt) mL/hour) and (INSfp>0 units/hour) and (INSfp≤(0.01*Wt) units/hour) then Dexfn=0 mL/hour and INSfn=(INSfp*1.5)

134. If (Xa≥(Xmin+2(Xmax−Xmin)/3) mg/dL) and (Xa<Xmax mg/dL) and (Xa−Xb>0 mg/dL) and (Dexfp>0 mL/hour) and (Dexfp≤(1/X*Wt) mL/hour) and (INSfp>(0.01*Wt) units/hour) and (INSfp≤(0.1*Wt) units/hour) then Dexfn=0 mL/hour and INSfn=(INSfp*1.15)

135. If (Xa≥(Xmin+2(Xmax−Xmin)/3) mg/dL) and (Xa<Xmax mg/dL) and (Xa−Xb>0 mg/dL) and (Dexfp>0 mL/hour) and (Dexfp≤(1/X*Wt) mL/hour) and (INSfp>(0.1*Wt) units/hour) then Dexfn=0 mL/hour and INSfn=(INSfp*1.05)

136. If (Xa≥(Xmin+2(Xmax−Xmin)/3) mg/dL) and (Xa<Xmax mg/dL) and (Xa−Xb>0 mg/dL) and (Dexfp>(1/X*Wt) mL/hour) and (Dexfp≤(6/X*Wt) mL/hour) and (INSfp>0 units/hour) and (INSfp≤(0.01*Wt) units/hour) then Dexfn=(Dexfp*0.8) and INSfn=(INSfp*1.5)

137. If (Xa≥(Xmin+2(Xmax−Xmin)/3) mg/dL) and (Xa<Xmax mg/dL) and (Xa−Xb>0 mg/dL) and (Dexfp>(1/X*Wt) mL/hour) and (Dexfp≤(6/X*Wt) mL/hour) and (INSfp>(0.01*Wt) units/hour) and (INSfp≤(0.1*Wt) units/hour) then Dexfn=(Dexfp*0.8) and INSfn=(INSfp*1.15)

138. If (Xa≥(Xmin+2(Xmax−Xmin)/3) mg/dL) and (Xa<Xmax mg/dL) and (Xa−Xb>0 mg/dL) and (Dexfp>(1/X*Wt) mL/hour) and (Dexfp≤(6/X*Wt) mL/hour) and (INSfp>(0.1*Wt) units/hour) then Dexfn=(Dexfp*0.8) and INSfn=(INSfp*1.05)

139. If (Xa≥(Xmin+2(Xmax−Xmin)/3) mg/dL) and (Xa<Xmax mg/dL) and (Xa−Xb>0 mg/dL) and (Dexfp>(6/X*Wt) mL/hour) and (INSfp>0 units/hour) and (INSfp≤(0.01*Wt) units/hour) then Dexfn=(Dexfp*0.85) and INSfn=(INSfp*1.5)

140. If (Xa≥(Xmin+2(Xmax−Xmin)/3) mg/dL) and (Xa<Xmax mg/dL) and (Xa−Xb>0 mg/dL) and (Dexfp>(6/X*Wt) mL/hour) and (INSfp>(0.01*Wt) units/hour) and (INSfp≤(0.1*Wt) units/hour) then Dexfn=(Dexfp*0.85) and INSfn=(INSfp*1.15)

141. If (Xa≥(Xmin+2(Xmax−Xmin)/3) mg/dL) and (Xa<Xmax mg/dL) and (Xa−Xb>0 mg/dL) and (Dexfp>(6/X*Wt) mL/hour) and (INSfp>(0.1*Wt) units/hour) then Dexfn=(Dexfp*0.85) and INSfn=(INSfp*1.05)

142. If (Xa≥(Xmin+2(Xmax−Xmin)/3) mg/dL) and (Xa<Xmax mg/dL) and (Xa−Xb≤−3 mg/dL) and (Dexfp>0 mL/hour) and (INSfp=0 units/hour) then Dexfn=Dexfp and INSfn=INSfp 143. If (Xa≥(Xmin+2(Xmax−Xmin)/3) mg/dL) and (Xa<Xmax mg/dL) and (Xa−Xb>−3 mg/dL) and (Xa−Xb≤0 mg/dL) and (Dexfp>0 mL/hour) and (Dexfp≤(1/X*Wt) mL/hour) and (INSfp=0 units/hour) then Dexfn=0 mL/hour and INSfn=INSfp 144. If (Xa≥(Xmin+2(Xmax−Xmin)/3) mg/dL) and (Xa<Xmax mg/dL) and (Xa−Xb>−3 mg/dL) and (Xa−Xb≤0 mg/dL) and (Dexfp>(1/X*Wt) mL/hour) and (INSfp=0 units/hour) then Dexfn=(Dexfp*0.95) and INSfn=INSfp 145. If (Xa≥(Xmin+2(Xmax−Xmin)/3) mg/dL) and (Xa<Xmax mg/dL) and (Xa−Xb>0 mg/dL) and (Dexfp>0 mL/hour) and (Dexfp≤(1/X*Wt) mL/hour) and (INSfp=0 units/hour) then Dexfn=0 mL/hour and INSfn=(0.02*Wt) units/hour 146. If (Xa≥(Xmin+2(Xmax−Xmin)/3) mg/dL) and (Xa<Xmax mg/dL) and (Xa−Xb>0 mg/dL) and (Dexfp>(1/X*Wt) mL/hour) and (INSfp=0 units/hour) then Dexfn=(Dexfp*0.9) and INSfn=(0.02*Wt) units/hour 147. If (Xa≥(Xmin+2(Xmax−Xmin)/3) mg/dL) and (Xa<Xmax mg/dL) and (Xa−Xb≤0 mg/dL) and (Dexfp=0 mL/hour) and (INSfp=0 units/hour) then Dexfn=Dexfp and INSfn=INSfp 148. If (Xa≥(Xmin+2(Xmax−Xmin)/3) mg/dL) and (Xa<Xmax mg/dL) and (Xa−Xb>0 mg/dL) and (Dexfp=0 mL/hour) and (INSfp=0 units/hour) then Dexfn=Dexfp and INSfn=(0.02*Wt) units/hour 149. If (Xa>Xmax mg/dL) and (Xa<(Xmax+10) mg/dL) and (Xa−Xb≤−4 mg/dL) and (Dexfp=0 mL/hour) and (INSfp>0 units/hour) and (INSfp≤(0.1*Wt) units/hour) then Dexfn=Dexfp and INSfn=(INSfp*0.9)

150. If (Xa>Xmax mg/dL) and (Xa<(Xmax+10) mg/dL) and (Xa−Xb≤−4 mg/dL) and (Dexfp=0 mL/hour) and (INSfp>(0.1*Wt) units/hour) then Dexfn=Dexfp and INSfn=(INSfp*0.95)

151. If (Xa>Xmax mg/dL) and (Xa<(Xmax+10) mg/dL) and (Xa−Xb>−4 mg/dL) and (Xa−Xb≤1 mg/dL) and (Dexfp=0 mL/hour) and (INSfp>0 units/hour) and (INSfp≤(0.02*Wt) units/hour) then Dexfn=Dexfp and INSfn=(INSfp*1.3)

152. If (Xa>Xmax mg/dL) and (Xa<(Xmax+10) mg/dL) and (Xa−Xb>−4 mg/dL) and (Xa−Xb≤1 mg/dL) and (Dexfp=0 mL/hour) and (INSfp>(0.02*Wt) units/hour) and (INSfp≥(0.1*Wt) units/hour) then Dexfn=Dexfp and INSfn=(INSfp*1.15)

153. If (Xa>Xmax mg/dL) and (Xa<(Xmax+10) mg/dL) and (Xa−Xb>−4 mg/dL) and (Xa−Xb≥1 mg/dL) and (Dexfp=0 mL/hour) and (INSfp>(0.1*Wt) units/hour) then Dexfn=Dexfp and INSfn=(INSfp*1.05)

154. If (Xa>Xmax mg/dL) and (Xa<(Xmax+10) mg/dL) and (Xa−Xb>1 mg/dL) and (Dexfp=0 mL/hour) and (INSfp>0 units/hour) and (INSfp≤(0.01*Wt) units/hour) then Dexfn=Dexfp and INSfn=(INSfp*1.5)

155. If (Xa>Xmax mg/dL) and (Xa<(Xmax+10) mg/dL) and (Xa−Xb>1 mg/dL) and (Dexfp=0 mL/hour) and (INSfp>(0.01*Wt) units/hour) and (INSfp≤(0.1*Wt) units/hour) then Dexfn=Dexfp and INSfn=(INSfp*1.3)

156. If (Xa>Xmax mg/dL) and (Xa<(Xmax+10) mg/dL) and (Xa−Xb>1 mg/dL) and (Dexfp=0 mL/hour) and (INSfp>(0.1*Wt) units/hour) then Dexfn=Dexfp and INSfn=(INSfp*1.1)

157. If (Xa>Xmax mg/dL) and (Xa<(Xmax+10) mg/dL) and (Xa−Xb≤−4 mg/dL) and (Dexfp>0 mL/hour) and (Dexfp≤(1/X*Wt) mL/hour) and (INSfp>0 units/hour) then Dexfn=0 mL/hour and INSfn=INSfp 158. If (Xa>Xmax mg/dL) and (Xa<(Xmax+10) mg/dL) and (Xa−Xb≤−4 mg/dL) and (Dexfp>(1/X*Wt) mL/hour) and (INSfp>0 units/hour) then Dexfn=(Dexfp×0.95) and INSfn=(INSfp*1.05)

159. If (Xa≥Xmax mg/dL) and (Xa<(Xmax+10) mg/dL) and (Xa−Xb>−4 mg/dL) and (Xa−Xb≤0 mg/dL) and (Dexfp>0 mL/hour) and (Dexfp<(1/X*Wt) mL/hour) and (INSfp>0 units/hour) then Dexfn=0 mL/hour and INSfn=(INSfp*1.05)
160. If (Xa≥Xmax mg/dL) and (Xa<(Xmax+10) mg/dL) and (Xa−Xb>−4 mg/dL) and (Xa−Xb≤0 mg/dL) and (Dexfp>(1/X*Wt) mL/hour) and (INSfp>0 units/hour) then Dexfn=(Dexfp*0.9) and INSfn=(INSfp*1.05)
161. If (Xa≥Xmax mg/dL) and (Xa<(Xmax+10) mg/dL) and (Xa−Xb>0 mg/dL) and (Dexfp>0 mL/hour) and (Dexfp≤(1/X*Wt) mL/hour) and (INSfp>0 units/hour) and (INSfp≥(0.01*Wt) units/hour) then Dexfn=0 mL/hour and INSfn=(INSfp*1.5)
162. If (Xa≥Xmax mg/dL) and (Xa<(Xmax+10) mg/dL) and (Xa−Xb>0 mg/dL) and (Dexfp>0 mL/hour) and (Dexfp≥(1/X*Wt) mL/hour) and (INSfp>(0.01*Wt) units/hour) and (INSfp<(0.1*Wt) units/hour) then Dexfn=0 mL/hour and INSfn=(INSfp*1.3)
163. If (Xa≥Xmax mg/dL) and (Xa<(Xmax+10) mg/dL) and (Xa−Xb>0 mg/dL) and (Dexfp>0 mL/hour) and (Dexfp≤(1/X*Wt) mL/hour) and (INSfp>(0.1*Wt) units/hour) then Dexfn=0 mL/hour and INSfn=(INSfp*1.1)
164. If (Xa≥Xmax mg/dL) and (Xa<(Xmax+10) mg/dL) and (Xa−Xb>0 mg/dL) and (Dexfp>(1/X*Wt) mL/hour) and (INSfp>0 units/hour) and (INSfp≤(0.01*Wt) units/hour) then Dexfn=(Dexfp*0.8) and INSfn=(INSfp*1.5)
165. If (Xa≥Xmax mg/dL) and (Xa<(Xmax+10) mg/dL) and (Xa−Xb>0 mg/dL) and (Dexfp>(1/X*Wt) mL/hour) and (INSfp>(0.01*Wt) units/hour) and (INSfp≤(0.1*Wt) units/hour) then Dexfn=(Dexfp*0.8) and INSfn=(INSfp*1.3)
166. If (Xa≥Xmax mg/dL) and (Xa<(Xmax+10) mg/dL) and (Xa−Xb>0 mg/dL) and (Dexfp>(1/X*Wt) mL/hour) and (INSfp>(0.1*Wt) units/hour) then Dexfn=(Dexfp*0.8) and INSfn=(INSfp*1.1)
167. If (Xa≥Xmax mg/dL) and (Xa<(Xmax+10) mg/dL) and (Xa−Xb≤0 mg/dL) and (Dexfp>0 mL/hour) and (Dexfp≤(1/X*Wt) mL/hour) and (INSfp=0 units/hour) then Dexfn=0 mL/hour and INSfn=INSfp
168. If (Xa≥Xmax mg/dL) and (Xa<(Xmax+10) mg/dL) and (Xa−Xb≤0 mg/dL) and (Dexfp>(1/X*Wt) mL/hour) and (INSfp=0 units/hour) then Dexfn=(Dexfp*0.9) mL/hour and INSfn=INSfp
169. If (Xa≥Xmax mg/dL) and (Xa<(Xmax+10) mg/dL) and (Xa−Xb>0 mg/dL) and (Dexfp>0 mL/hour) and (Dexfp≤(1/X*Wt) mL/hour) and (INSfp=0 units/hour) then Dexfn=0 mL/hour and INSfn=(0.02*Wt) units/hour
170. If (Xa≥Xmax mg/dL) and (Xa<(Xmax+10) mg/dL) and (Xa−Xb>0 mg/dL) and (Dexfp>(1/X*Wt) mL/hour) and (INSfp=0 units/hour) then Dexfn=(Dexfp*0.8) mL/hour and INSfn=(0.02*Wt) units/hour
171. If (Xa≥Xmax mg/dL) and (Xa<(Xmax+10) mg/dL) and (Xa−Xb≤−3 mg/dL) and (Dexfp=0 mL/hour) and (INSfp=0 units/hour) then Dexfn=Dexfp and INSfn=INSfp
172. If (Xa≥Xmax mg/dL) and (Xa<(Xmax+10) mg/dL) and (Xa−Xb>−3 mg/dL) and (Dexfp=0 mL/hour) and (INSfp=0 units/hour) then Dexfn=Dexfp and INSfn=(0.02*Wt) units/hour
173. If (Xa≥(Xmax+10) mg/dL) and (Xa<(Xmax+30) mg/dL) and (Xa−Xb≤−6 mg/dL) and (Dexfp=0 mL/hour) and (INSfp>0 units/hour) and (INSfp≤(0.1*Wt) units/hour) then Dexfn=Dexfp and INSfn=(INSfp*0.9)
174. If (Xa≥(Xmax+10) mg/dL) and (Xa<(Xmax+30) mg/dL) and (Xa−Xb≤−6 mg/dL) and (Dexfp=0 mL/hour) and (INSfp>(0.1*Wt) units/hour) then Dexfn=Dexfp and INSfn=(INSfp*0.95)
175. If (Xa≥(Xmax+10) mg/dL) and (Xa<(Xmax+30) mg/dL) and (Xa−Xb>−6 mg/dL) and (Xa−Xb≤0 mg/dL) and (Dexfp=0 mL/hour) and (INSfp>0 units/hour) and (INSfp≤(0.02*Wt) units/hour) then Dexfn=Dexfp and INSfn=(INSfp 1.4)
176. If (Xa≥(Xmax+10) mg/dL) and (Xa<(Xmax+30) mg/dL) and (Xa−Xb>−6 mg/dL) and (Xa−Xb≤0 mg/dL) and (Dexfp=0 mL/hour) and (INSfp>(0.02*Wt) units/hour) and (INSfp≤(0.1*Wt) units/hour) then Dexfn=Dexfp and INSfn=(INSfp*1.2)
177. If (Xa≥(Xmax+10) mg/dL) and (Xa<(Xmax+30) mg/dL) and (Xa−Xb>−6 mg/dL) and (Xa−Xb≤0 mg/dL) and (Dexfp=0 mL/hour) and (INSfp>(0.1*Wt) units/hour) then Dexfn=Dexfp and INSfn=(INSfp*1.1)
178. If (Xa≥(Xmax+10) mg/dL) and (Xa<(Xmax+30) mg/dL) and (Xa−Xb>0 mg/dL) and (Dexfp=0 mL/hour) and (INSfp>0 units/hour) and (INSfp<(0.02*Wt) units/hour) then Dexfn=Dexfp and INSfn=(INSfp*1.5)
179. If (Xa≥(Xmax+10) mg/dL) and (Xa<(Xmax+30) mg/dL) and (Xa−Xb>0 mg/dL) and (Dexfp=0 mL/hour) and (INSfp>(0.02*Wt) units/hour) and (INSfp≤(0.1*Wt) units/hour) then Dexfn=Dexfp and INSfn=(INSfp*1.3)
180. If (Xa≥(Xmax+10) mg/dL) and (Xa<(Xmax+30) mg/dL) and (Xa−Xb>0 mg/dL) and (Dexfp=0 mL/hour) and (INSfp>(0.1*Wt) units/hour) then Dexfn=Dexfp and INSfn=(INSfp*1.1)
181. If (Xa≥(Xmax+10) mg/dL) and (Xa<(Xmax+30) mg/dL) and (Xa−Xb≤−6 mg/dL) and (Dexfp>0 mL/hour) and (Dexfp≤(2/X*Wt) mL/hour) and (INSfp>0 units/hour) then Dexfn=0 mL/hour and INSfn=(INSfp*1.1)
182. If (Xa≥(Xmax+10) mg/dL) and (Xa<(Xmax+30) mg/dL) and (Xa−Xb≤−6 mg/dL) and (Dexfp>(2/X*Wt) mL/hour) and (Dexfp≤(6/X*Wt) mL/hour) and (INSfp>0 units/hour) then Dexfn=(Dexfp*0.8) and INSfn=(INSfp*1.1)
183. If (Xa≥(Xmax+10) mg/dL) and (Xa<(Xmax+30) mg/dL) and (Xa−Xb≤−6 mg/dL) and (Dexfp>(6/X*Wt) mL/hour) and (INSfp>0 units/hour) then Dexfn=(Dexfp*0.9) and INSfn=(INSfp*1.1)
184. If (Xa≥(Xmax+10) mg/dL) and (Xa<(Xmax+30) mg/dL) and (Xa−Xb>−6 mg/dL) and (Dexfp>0 mL/hour) and (Dexfp≤(2/X*Wt) mL/hour) and (INSfp>0 units/hour) and (INSfp≤(0.02*Wt) units/hour) then Dexfn=0 mL/hour and INSfn=(INSfp*1.5)
185. If (Xa≥(Xmax+10) mg/dL) and (Xa<(Xmax+30) mg/dL) and (Xa−Xb>−6 mg/dL) and (Dexfp>0 mL/hour) and (Dexfp≤(2/X*Wt) mL/hour) and (INSfp>(0.02*Wt) units/hour) and (INSfp≤(0.1*Wt) units/hour) then Dexfn=0 mL/hour and INSfn=(INSfp*1.3)
186. If (Xa≥(Xmax+10) mg/dL) and (Xa<(Xmax+30) mg/dL) and (Xa−Xb>−6 mg/dL) and (Dexfp>0 mL/hour) and (Dexfp≤(2/X*Wt) mL/hour) and (INSfp>(0.1*Wt) units/hour) then Dexfn=0 mL/hour and INSfn=(INSfp*1.1)
187. If (Xa≥(Xmax+10) mg/dL) and (Xa<(Xmax+30) mg/dL) and (Xa−Xb>−6 mg/dL) and (Dexfp>(2/X*Wt) mL/hour) and (INSfp>0 units/hour) and (INSfp≤(0.02*Wt) units/hour) then Dexfn=(Dexfp*0.8) and INSfn=(INSfp*1.5)
188. If (Xa≥(Xmax+10) mg/dL) and (Xa<(Xmax+30) mg/dL) and (Xa−Xb>−6 mg/dL) and (Dexfp>(2/X*Wt) mL/hour) and (INSfp>(0.02*Wt) units/hour) and (INSfp≤(0.1*Wt) units/hour) then Dexfn=(Dexfp*0.8) and INSfn=(INSfp*1.3)
189. If (Xa≥(Xmax+10) mg/dL) and (Xa<(Xmax+30) mg/dL) and (Xa−Xb>−6 mg/dL) and (Dexfp>(2/X*Wt)

190. If (Xa≥(Xmax+10) mg/dL) and (Xa<(Xmax+30) mg/dL) and (Xa−Xb≤1 mg/dL) and (Dexfp>0 mL/hour) and (Dexfp≤(1/X*Wt) mL/hour) and (INSfp=0 units/hour) then Dexfn=0 mL/hour and INSfn=(0.03*Wt) units/hour 191. If (Xa≥(Xmax+10) mg/dL) and (Xa<(Xmax+30) mg/dL) and (Xa−Xb≤1 mg/dL) and (Dexfp>(1/X*Wt) mL/hour) and (INSfp=0 units/hour) then Dexfn=(Dexfp*0.8) mL/hour and INSfn=(0.03*Wt) units/hour 192. If (Xa≥(Xmax+10) mg/dL) and (Xa<(Xmax+30) mg/dL) and (Xa−Xb>1 mg/dL) and (Dexfp>0 mL/hour) and (Dexfp≤(1/X*Wt) mL/hour) and (INSfp=0 units/hour) then Dexfn=0 mL/hour and INSfn=(0.03*Wt) units/hour 193. If (Xa≥(Xmax+10) mg/dL) and (Xa<(Xmax+30) mg/dL) and (Xa−Xb>1 mg/dL) and (Dexfp>(1/X*Wt) mL/hour) and (INSfp=0 units/hour) then Dexfn=(Dexfp*0.7) mL/hour and INSfn=(0.03*Wt) units/hour 194. If (Xa≥(Xmax+10) mg/dL) and (Xa<(Xmax+30) mg/dL) and (Xa−Xb≤−3 mg/dL) and (Dexfp=0 mL/hour) and (INSfp=0 units/hour) then Dexfn=Dexfp and INSfn=(0.02*Wt) units/hour 195. If (Xa≥(Xmax+10) mg/dL) and (Xa<(Xmax+30) mg/dL) and (Xa−Xb>−3 mg/dL) and (Dexfp=0 mL/hour) and (INSfp=0 units/hour) then Dexfn=0 mL/hour and INSfn=(0.03*Wt) units/hour 196. If (Xa≥(Xmax+30) mg/dL) and (Xa−Xb≤−15 mg/dL) and (Dexfp=0 mL/hour) and (INSfp>0 units/hour) then Dexfn=0 mL/hour and INSfn=INSfp 197. If (Xa≥(Xmax+30) mg/dL) and (Xa−Xb>−15 mg/dL) and (Dexfp=0 mL/hour) and (INSfp>0 units/hour) and (INSfp≤(0.02*Wt) units/hour) then Dexfn=Dexfp and INSfn=(INSfp*1.6)

198. If (Xa≥(Xmax+30) mg/dL) and (Xa−Xb>−15 mg/dL) and (Dexfp=0 mL/hour) and (INSfp>(0.02*Wt) units/hour) and (INSfp≤(0.1*Wt) units/hour) then Dexfn=Dexfp and INSfn=(INSfp*1.4)

199. If (Xa≥(Xmax+30) mg/dL) and (Xa−Xb>−15 mg/dL) and (Dexfp=0 mL/hour) and (INSfp>(0.1*Wt) units/hour) then Dexfn=Dexfp and INSfn=(INSfp*1.1)

200. If (Xa≥(Xmax+30) mg/dL) and (Xa−Xb≤−15 mg/dL) and (Dexfp>0 mL/hour) and (Dexfp≤(2/X*Wt) mL/hour) and (INSfp>0 units/hour) and (INSfp≤(0.02*Wt) units/hour) then Dexfn=0 mL/hour and INSfn=(INSfp*1.5)

201. If (Xa≥(Xmax+30) mg/dL) and (Xa−Xb≤−15 mg/dL) and (Dexfp>0 mL/hour) and (Dexfp≤(2/X*Wt) mL/hour) and (INSfp>(0.02*Wt) units/hour) and (INSfp≤(0.1*Wt) units/hour) then Dexfn=0 mL/hour and INSfn=(INSfp*1.2)

202. If (Xa≥(Xmax+30) mg/dL) and (Xa−Xb≤−15 mg/dL) and (Dexfp>0 mL/hour) and (Dexfp≤(2/X*Wt) mL/hour) and (INSfp>(0.1*Wt) units/hour) then Dexfn=0 mL/hour and INSfn=(INSfp*1.05)

203. If (Xa≥(Xmax+30) mg/dL) and (Xa−Xb≤−15 mg/dL) and (Dexfp>(2/X*Wt) mL/hour) and (INSfp>0 units/hour) and (INSfp≤(0.02*Wt)) units/hour) then Dexfn=(Dexfp*0.9) and INSfn=(INSfp*1.5)

204. If (Xa≥(Xmax+30) mg/dL) and (Xa−Xb≤−15 mg/dL) and (Dexfp>(2/X*Wt) mL/hour) and (INSfp>(0.02*Wt) units/hour) and (INSfp≤(0.1*Wt) units/hour) then Dexfn=(Dexfp*0.9) and INSfn=(INSfp*1.2)

205. If (Xa≥(Xmax+30) mg/dL) and (Xa−Xb≤−15 mg/dL) and (Dexfp>(2/X*Wt) mL/hour) and (INSfp>(0.1*Wt) units/hour) then Dexfn=(Dexfp*0.9) and INSfn=(INSfp*1.05)

206. If (Xa≥(Xmax+30) mg/dL) and (Xa−Xb>−15 mg/dL) and (Dexfp>0 mL/hour) and (Dexfp≤(2/X*Wt) mL/hour) and (INSfp>0 units/hour) and (INSfp≤(0.02*Wt) units/hour) then Dexfn=0 mL/hour and INSfn=(INSfp*1.7)

207. If (Xa≥(Xmax+30) mg/dL) and (Xa−Xb>−15 mg/dL) and (Dexfp>0 mL/hour) and (Dexfp≤(2/X*Wt) mL/hour) and (INSfp>(0.02*Wt) units/hour) and (INSfp<(0.1*Wt) units/hour) then Dexfn=0 mL/hour and INSfn=(INSfp*1.3)

208. If (Xa≥(Xmax+30) mg/dL) and (Xa−Xb>−15 mg/dL) and (Dexfp>0 mL/hour) and (Dexfp≤(2/X*Wt) mL/hour) and (INSfp>(0.1*Wt) units/hour) then Dexfn=0 mL/hour and INSfn=(INSfp 1.1)

209. If (Xa≥(Xmax+30) mg/dL) and (Xa−Xb>−15 mg/dL) and (Dexfp>(2/X*Wt) mL/hour) and (INSfp>0 units/hour) and (INSfp≤(0.02*Wt) units/hour) then Dexfn=(Dexfp*0.Xmin) and INSfn=(INSfp*1.7)

210. If (Xa≥(Xmax+30) mg/dL) and (Xa−Xb>−15 mg/dL) and (Dexfp>(2/X*Wt) mL/hour) and (INSfp>(0.02*Wt) units/hour) and (INSfp≤(0.1*Wt) units/hour) then Dexfn=(Dexfp*0.Xmin) and INSfn=(INSfp*1.3)

211. If (Xa≥(Xmax+30) mg/dL) and (Xa−Xb>−15 mg/dL) and (Dexfp>(2/X*Wt) mL/hour) and (INSfp>(0.1*Wt) units/hour) then Dexfn=(Dexfp*0.75) and INSfn=(INSfp*1.1)

212. If (Xa≥(Xmax+30) mg/dL) and (Xa−Xb≤−15 mg/dL) and (Dexfp>0 mL/hour) and (Dexfp≤(1/X*Wt) mL/hour) and (INSfp=0 units/hour) then Dexfn=0 mL/hour and INSfn=(0.01*Wt) units/hour 213. If (Xa≥(Xmax+30) mg/dL) and (Xa−Xb≤−15 mg/dL) and (Dexfp>(1/X*Wt) mL/hour) and (INSfp=0 units/hour) then Dexfn=(Dexfp*0.9) and INSfn=(0.01*Wt) units/hour 214. If (Xa≥(Xmax+30) mg/dL) and (Xa−Xb>−15 mg/dL) and (Dexfp>0 mL/hour) and (Dexfp≤(2/X*Wt) mL/hour) and (INSfp=0 units/hour) then Dexfn=0 mL/hour and INSfn=(0.03*Wt) units/hour 215. If (Xa≥(Xmax+30) mg/dL) and (Xa−Xb>−15 mg/dL) and (Dexfp>(2/X*Wt) mL/hour) and (INSfp=0 units/hour) then Dexfn=(Dexfp*0.7) and INSfn=(0.03*Wt) units/hour 216. If (Xa≥(Xmax+30) mg/dL) and (Xa−Xb≤−15 mg/dL) and (Dexfp=0 mL/hour) and (INSfp=0 units/hour) then Dexfn=Dexfp and INSfn=(0.01*Wt) units/hour 217. If (Xa≥(Xmax+30) mg/dL) and (Xa−Xb>−15 mg/dL) and (Dexfp=0 mL/hour) and (INSfp=0 units/hour) then Dexfn=Dexfp and INSfn=(0.03*Wt) units/hour 218. If (Xa≥(Xmax+20 mg/dL) and (Xa<(Xmax+50 mg/dL) and (Xa−Xb≥−5 mg/dL) then (give bolus dose insulin=(0.04 units*Wt) over 10 minutes) in addition to INSfn as calculated by algorithm.

219. If (Xa≥(Xmax+50) mg/dL) and (Xa<(Xmax+90) mg/dL) and (Xa−Xb>−15 mg/dL) then (give bolus dose insulin=(0.04 units*Wt) over 10 minutes) in addition to INSfn as calculated by algorithm 220. If (Xa≥(Xmax+90) mg/dL) and (Xa−Xb>−20 mg/dL) then (give bolus dose insulin=(0.08 units*Wt) over 10 minutes) in addition to INSfn as calculated by algorithm 221. If (Dexfn≥DexSh) then Dexfn=DexSh and activate alarm "Maximum Dextrose Infusion Rate"

222. If (INSfn≥INSSh) then INSfn=INSSh and activate alarm "Maximum Insulin Infusion Rate"

223. MIVFR=TIVFR−(Dexfn+(INSfn*Conc$^{-1}$)

| | Glucose Algorithm Table | | |
|---|---|---|---|
| | Xa (mg/dL) | AND Xa − Xb (mg/dL) | AND Dexfp (mL/hr) |
| 1 | Xa − Xmin < −10 | | Dexfp = 0 |
| 2 | Xa − Xmin < −10 | Xa − Xb < −3 | 0 < Dexfp ≤ 2/C * Wt |
| 3 | Xa − Xmin < −10 | Xa − Xb < −3 | 0 < Dexfp ≤ 2/C * Wt |
| 4 | Xa − Xmin < −10 | Xa − Xb < −3 | 2/C * Wt < Dexfp ≤ 6/C * Wt |
| 5 | Xa − Xmin < −10 | Xa − Xb < −3 | 2/C * Wt < Dexfp ≤ 6/C * Wt |
| 6 | Xa − Xmin < −10 | Xa − Xb < −3 | 6/C * Wt < Dexfp |
| 7 | Xa − Xmin < −10 | Xa − Xb < −3 | 6/C * Wt < Dexfp |
| 8 | Xa − Xmin < −10 | −3 ≤ Xa − Xb | 0 < Dexfp ≤ 2/C * Wt |
| 9 | Xa − Xmin < −10 | −3 ≤ Xa − Xb | 0 < Dexfp ≤ 2/C * Wt |
| 10 | Xa − Xmin < −10 | −3 ≤ Xa − Xb | 2/C * Wt < Dexfp ≤ 6/C * Wt |
| 11 | Xa − Xmin < −10 | −3 ≤ Xa − Xb | 2/C * Wt < Dexfp ≤ 6/C * Wt |
| 12 | Xa − Xmin < −10 | −3 ≤ Xa − Xb | 6/C * Wt < Dexfp |
| 13 | Xa − Xmin < −10 | −3 ≤ Xa − Xb | 6/C * Wt < Dexfp |
| 14 | Xa − Xmin < −10 | Xa − Xb < −3 | 0 < Dexfp ≤ 2/C * Wt |
| 15 | Xa − Xmin < −10 | Xa − Xb < −3 | 2/C * Wt < Dexfp ≤ 6/C * Wt |
| 16 | Xa − Xmin < −10 | Xa − Xb < −3 | 6/C * Wt < Dexfp |
| 17 | Xa − Xmin < −10 | −3 ≤ Xa − Xb | 0 < Dexfp ≤ 2/C * Wt |
| 18 | Xa − Xmin < −10 | −3 ≤ Xa − Xb | 2/C * Wt < Dexfp ≤ 6/C * Wt |
| 19 | Xa − Xmin < −10 | −3 ≤ Xa − Xb | 6/C * Wt < Dexfp |
| 20 | Xa − Xmin < −10 | | Dexfp = 0 |
| 21 | −10 ≤ Xa − Xmin < −5 | Xa − Xb < 0 | Dexfp = 0 |
| 22 | −10 ≤ Xa − Xmin < −5 | Xa − Xb < 0 | Dexfp = 0 |
| 23 | −10 ≤ Xa − Xmin < −5 | Xa − Xb < 0 | Dexfp = 0 |
| 24 | −10 ≤ Xa − Xmin < −5 | 0 ≤ Xa − Xb | Dexfp = 0 |
| 25 | −10 ≤ Xa − Xmin < −5 | 0 ≤ Xa − Xb | Dexfp = 0 |
| 26 | −10 ≤ Xa − Xmin < −5 | 0 ≤ Xa − Xb | Dexfp = 0 |
| 27 | −10 ≤ Xa − Xmin < −5 | Xa − Xb < −3 | 0 < Dexfp ≤ 2/C * Wt |
| 28 | −10 ≤ Xa − Xmin < −5 | Xa − Xb < −3 | 0 < Dexfp ≤ 2/C * Wt |
| 29 | −10 ≤ Xa − Xmin < −5 | Xa − Xb < −3 | 0 < Dexfp ≤ 2/C * Wt |
| 30 | −10 ≤ Xa − Xmin < −5 | Xa − Xb < −3 | 2/C * Wt < Dexfp ≤ 6/C * Wt |
| 31 | −10 ≤ Xa − Xmin < −5 | Xa − Xb < −3 | 2/C * Wt < Dexfp ≤ 6/C * Wt |
| 32 | −10 ≤ Xa − Xmin < −5 | Xa − Xb < −3 | 2/C * Wt < Dexfp ≤ 6/C * Wt |
| 33 | −10 ≤ Xa − Xmin < −5 | Xa − Xb < −3 | 6/C * Wt < Dexfp |
| 34 | −10 ≤ Xa − Xmin < −5 | Xa − Xb < −3 | 6/C * Wt < Dexfp |
| 35 | −10 ≤ Xa − Xmin < −5 | Xa − Xb < −3 | 6/C * Wt < Dexfp |
| 36 | −10 ≤ Xa − Xmin < −5 | −3 ≤ Xa − Xb ≤ 1 | 0 < Dexfp |
| 37 | −10 ≤ Xa − Xmin < −5 | −3 ≤ Xa − Xb ≤ 1 | 0 < Dexfp |
| 38 | −10 ≤ Xa − Xmin < −5 | −3 ≤ Xa − Xb ≤ 1 | 0 < Dexfp |
| 39 | −10 ≤ Xa − Xmin < −5 | 1 < Xa − Xb | 0 < Dexfp |
| 40 | −10 ≤ Xa − Xmin < −5 | Xa − Xb < −1 | 0 < Dexfp ≤ 2/C * Wt |
| 41 | −10 ≤ Xa − Xmin < −5 | Xa − Xb < −1 | 2/C * Wt < Dexfp ≤ 6/C * Wt |
| 42 | −10 ≤ Xa − Xmin < −5 | Xa − Xb < −1 | 6/C * Wt < Dexfp |
| 43 | −10 ≤ Xa − Xmin < −5 | −1 ≤ Xa − Xb | 0 < Dexfp |
| 44 | −10 ≤ Xa − Xmin < −5 | Xa − Xb < −1 | Dexfp = 0 |
| 45 | −10 ≤ Xa − Xmin < −5 | −1 ≤ Xa − Xb | Dexfp = 0 |
| 46 | −5 ≤ Xa − Xmin < 0 | Xa − Xb < −2 | Dexfp = 0 |
| 47 | −5 ≤ Xa − Xmin < 0 | Xa − Xb < −2 | Dexfp = 0 |
| 48 | −5 ≤ Xa − Xmin < 0 | Xa − Xb < −2 | Dexfp = 0 |
| 49 | −5 ≤ Xa − Xmin < 0 | −2 ≤ Xa − Xb | Dexfp = 0 |
| 50 | −5 ≤ Xa − Xmin < 0 | −2 ≤ Xa − Xb | Dexfp = 0 |
| 51 | −5 ≤ Xa − Xmin < 0 | −2 ≤ Xa − Xb | Dexfp = 0 |
| 52 | −5 ≤ Xa − Xmin < 0 | Xa − Xb < −2 | 0 < Dexfp ≤ 2/C * Wt |
| 53 | −5 ≤ Xa − Xmin < 0 | Xa − Xb < −2 | 0 < Dexfp ≤ 2/C * Wt |
| 54 | −5 ≤ Xa − Xmin < 0 | Xa − Xb < −2 | 0 < Dexfp ≤ 2/C * Wt |
| 55 | −5 ≤ Xa − Xmin < 0 | Xa − Xb < −2 | 2/C * Wt < Dexfp ≤ 6/C * Wt |
| 56 | −5 ≤ Xa − Xmin < 0 | Xa − Xb < −2 | 2/C * Wt < Dexfp ≤ 6/C * Wt |
| 57 | −5 ≤ Xa − Xmin < 0 | Xa − Xb < −2 | 2/C * Wt < Dexfp ≤ 6/C * Wt |
| 58 | −5 ≤ Xa − Xmin < 0 | Xa − Xb < −2 | 6/C * Wt < Dexfp |
| 59 | −5 ≤ Xa − Xmin < 0 | Xa − Xb < −2 | 6/C * Wt < Dexfp |
| 60 | −5 ≤ Xa − Xmin < 0 | Xa − Xb < −2 | 6/C * Wt < Dexfp |
| 61 | −5 ≤ Xa − Xmin < 0 | −2 ≤ Xa − Xb | 0 < Dexfp |
| 62 | −5 ≤ Xa − Xmin < 0 | −2 ≤ Xa − Xb | 0 < Dexfp |
| 63 | −5 ≤ Xa − Xmin < 0 | Xa − Xb < −1 | 0 < Dexfp ≤ 2/C * Wt |
| 64 | −5 ≤ Xa − Xmin < 0 | Xa − Xb < −1 | 2/C * Wt < Dexfp ≤ 6/C * Wt |
| 65 | −5 ≤ Xa − Xmin < 0 | Xa − Xb < −1 | 6/C * Wt < Dexfp |
| 66 | −5 ≤ Xa − Xmin < 0 | −1 ≤ Xa − Xb | 0 < Dexfp |
| 67 | −5 ≤ Xa − Xmin < 0 | Xa − Xb < −1 | Dexfp = 0 |
| 68 | −5 ≤ Xa − Xmin < 0 | −1 ≤ Xa − Xb | Dexfp = 0 |
| 69 | 0 ≤ Xa − Xmin < (Xmax − Xmin)/3 | Xa − Xb ≤ −2 | Dexfp = 0 |
| 70 | 0 ≤ Xa − Xmin < (Xmax − Xmin)/3 | Xa − Xb ≤ −2 | Dexfp = 0 |
| 71 | 0 ≤ Xa − Xmin < (Xmax − Xmin)/3 | Xa − Xb ≤ −2 | Dexfp = 0 |
| 72 | 0 ≤ Xa − Xmin < (Xmax − Xmin)/3 | −2 < Xa − Xb ≤ 3 | Dexfp = 0 |
| 73 | 0 ≤ Xa − Xmin < (Xmax − Xmin)/3 | 3 < Xa − Xb | Dexfp = 0 |
| 74 | 0 ≤ Xa − Xmin < (Xmax − Xmin)/3 | Xa − Xb ≤ −2 | 0 < Dexfp ≤ 2/C * Wt |
| 75 | 0 ≤ Xa − Xmin < (Xmax − Xmin)/3 | Xa − Xb ≤ −2 | 0 < Dexfp ≤ 2/C * Wt |

-continued

| | Glucose Algorithm Table | | |
|---|---|---|---|
| 76 | 0 ≤ Xa − Xmin < (Xmax − Xmin)/3 | Xa − Xb ≤ −2 | 0 < Dexfp ≤ 2/C * Wt |
| 77 | 0 ≤ Xa − Xmin < (Xmax − Xmin)/3 | Xa − Xb ≤ −2 | 2/C * Wt < Dexfp ≤ 6/C * Wt |
| 78 | 0 ≤ Xa − Xmin < (Xmax − Xmin)/3 | Xa − Xb ≤ −2 | 2/C * Wt < Dexfp ≤ 6/C * Wt |
| 79 | 0 ≤ Xa − Xmin < (Xmax − Xmin)/3 | Xa − Xb ≤ −2 | 2/C * Wt < Dexfp ≤ 6/C * Wt |
| 80 | 0 ≤ Xa − Xmin < (Xmax − Xmin)/3 | Xa − Xb ≤ −2 | 6/C * Wt < Dexfp |
| 81 | 0 ≤ Xa − Xmin < (Xmax − Xmin)/3 | Xa − Xb ≤ −2 | 6/C * Wt < Dexfp |
| 82 | 0 ≤ Xa − Xmin < (Xmax − Xmin)/3 | Xa − Xb ≤ −2 | 6/C * Wt < Dexfp |
| 83 | 0 ≤ Xa − Xmin < (Xmax − Xmin)/3 | −2 < Xa − Xb ≤ 3 | 0 < Dexfp |
| 84 | 0 ≤ Xa − Xmin < (Xmax − Xmin)/3 | 3 < Xa − Xb | 0 < Dexfp ≤ 1/C * Wt |
| 85 | 0 ≤ Xa − Xmin < (Xmax − Xmin)/3 | 3 < Xa − Xb | 1/C * Wt < Dexfp |
| 86 | 0 ≤ Xa − Xmin < (Xmax − Xmin)/3 | Xa − Xb ≤ −2 | 0 < Dexfp ≤ 2/C * Wt |
| 87 | 0 ≤ Xa − Xmin < (Xmax − Xmin)/3 | Xa − Xb ≤ −2 | 2/C * Wt < Dexfp ≤ 6/C * Wt |
| 88 | 0 ≤ Xa − Xmin < (Xmax − Xmin)/3 | Xa − Xb ≤ −2 | 6/C * Wt < Dexfp |
| 89 | 0 ≤ Xa − Xmin < (Xmax − Xmin)/3 | −2 < Xa − Xb ≤ 3 | 0 < Dexfp |
| 90 | 0 ≤ Xa − Xmin < (Xmax − Xmin)/3 | 3 < Xa − Xb | 0 < Dexfp ≤ 1/C * Wt |
| 91 | 0 ≤ Xa − Xmin < (Xmax − Xmin)/3 | 3 < Xa − Xb | 1/C * Wt < Dexfp |
| 92 | 0 ≤ Xa − Xmin < (Xmax − Xmin)/3 | Xa − Xb ≤ −3 | Dexfp = 0 |
| 93 | 0 ≤ Xa − Xmin < (Xmax − Xmin)/3 | −3 < Xa − Xb ≤ 3 | Dexfp = 0 |
| 94 | 0 ≤ Xa − Xmin < (Xmax − Xmin)/3 | 3 < Xa − Xb | Dexfp = 0 |
| 95 | (Xmax − Xmin)/3 ≤ Xa − Xmin < 2(Xmax − Xmin)/3 | Xa − Xb ≤ −3 | Dexfp = 0 |
| 96 | (Xmax − Xmin)/3 ≤ Xa − Xmin < 2(Xmax − Xmin)/3 | Xa − Xb ≤ −3 | Dexfp = 0 |
| 97 | (Xmax − Xmin)/3 ≤ Xa − Xmin < 2(Xmax − Xmin)/3 | Xa − Xb ≤ −3 | Dexfp = 0 |
| 98 | (Xmax − Xmin)/3 ≤ Xa − Xmin < 2(Xmax − Xmin)/3 | −3 < Xa − Xb ≤ 3 | Dexfp = 0 |
| 99 | (Xmax − Xmin)/3 ≤ Xa − Xmin < 2(Xmax − Xmin)/3 | 3 < Xa − Xb | Dexfp = 0 |
| 100 | (Xmax − Xmin)/3 ≤ Xa − Xmin < 2(Xmax − Xmin)/3 | 3 < Xa − Xb | Dexfp = 0 |
| 101 | (Xmax − Xmin)/3 ≤ Xa − Xmin < 2(Xmax − Xmin)/3 | 3 < Xa − Xb | Dexfp = 0 |
| 102 | (Xmax − Xmin)/3 ≤ Xa − Xmin < 2(Xmax − Xmin)/3 | Xa − Xb ≤ −3 | 0 < Dexfp |
| 103 | (Xmax − Xmin)/3 ≤ Xa − Xmin < 2(Xmax − Xmin)/3 | Xa − Xb ≤ −3 | 0 < Dexfp |
| 104 | (Xmax − Xmin)/3 ≤ Xa − Xmin < 2(Xmax − Xmin)/3 | Xa − Xb ≤ −3 | 0 < Dexfp |
| 105 | (Xmax − Xmin)/3 ≤ Xa − Xmin < 2(Xmax − Xmin)/3 | −3 < Xa − Xb ≤ 3 | 0 < Dexfp |
| 106 | (Xmax − Xmin)/3 ≤ Xa − Xmin < 2(Xmax − Xmin)/3 | 3 < Xa − Xb | 0 < Dexfp ≤ 1/C * Wt |
| 107 | (Xmax − Xmin)/3 ≤ Xa − Xmin < 2(Xmax − Xmin)/3 | 3 < Xa − Xb | 0 < Dexfp ≤ 1/C * Wt |
| 108 | (Xmax − Xmin)/3 ≤ Xa − Xmin < 2(Xmax − Xmin)/3 | 3 < Xa − Xb | 0 < Dexfp ≤ 1/C * Wt |
| 109 | (Xmax − Xmin)/3 ≤ Xa − Xmin < 2(Xmax − Xmin)/3 | 3 < Xa − Xb | 1/C * Wt < Dexfp ≤ 6/C * Wt |
| 110 | (Xmax − Xmin)/3 ≤ Xa − Xmin < 2(Xmax − Xmin)/3 | 3 < Xa − Xb | 1/C * Wt < Dexfp ≤ 6/C * Wt |
| 111 | (Xmax − Xmin)/3 ≤ Xa − Xmin < 2(Xmax − Xmin)/3 | 3 < Xa − Xb | 1/C * Wt < Dexfp ≤ 6/C * Wt |
| 112 | (Xmax − Xmin)/3 ≤ Xa − Xmin < 2(Xmax − Xmin)/3 | 3 < Xa − Xb | 6/C * Wt < Dexfp |
| 113 | (Xmax − Xmin)/3 ≤ Xa − Xmin < 2(Xmax − Xmin)/3 | 3 < Xa − Xb | 6/C * Wt < Dexfp |
| 114 | (Xmax − Xmin)/3 ≤ Xa − Xmin < 2(Xmax − Xmin)/3 | 3 < Xa − Xb | 6/C * Wt < Dexfp |
| 115 | (Xmax − Xmin)/3 ≤ Xa − Xmin < 2(Xmax − Xmin)/3 | Xa − Xb ≤ −3 | 0 < Dexfp ≤ 1/C * Wt |
| 116 | (Xmax − Xmin)/3 ≤ Xa − Xmin < 2(Xmax − Xmin)/3 | Xa − Xb ≤ −3 | 1/C * Wt < Dexfp ≤ 6/C * Wt |
| 117 | (Xmax − Xmin)/3 ≤ Xa − Xmin < 2(Xmax − Xmin)/3 | Xa − Xb ≤ −3 | 6/C * Wt < Dexfp |
| 118 | (Xmax − Xmin)/3 ≤ Xa − Xmin < 2(Xmax − Xmin)/3 | −3 < Xa − Xb ≤ 3 | 0 < Dexfp |
| 119 | (Xmax − Xmin)/3 ≤ Xa − Xmin < 2(Xmax − Xmin)/3 | 3 < Xa − Xb | 0 < Dexfp ≤ 1/C * Wt |
| 120 | (Xmax − Xmin)/3 ≤ Xa − Xmin < 2(Xmax − Xmin)/3 | 3 < Xa − Xb | 1/C * Wt < Dexfp |
| 121 | (Xmax − Xmin)/3 ≤ Xa − Xmin < 2(Xmax − Xmin)/3 | Xa − Xb ≤ 2 | Dexfp = 0 |
| 122 | (Xmax − Xmin)/3 ≤ Xa − Xmin < 2(Xmax − Xmin)/3 | 2 < Xa − Xb | Dexfp = 0 |
| 123 | (2(Xmax − Xmin)/3) ≤ Xa − Xmin < (Xmax − Xmin) | Xa − Xb ≤ −5 | Dcxfp = 0 |
| 124 | (2(Xmax − Xmin)/3) ≤ Xa − Xmin < (Xmax − Xmin) | Xa − Xb ≤ −5 | Dexfp = 0 |
| 125 | (2(Xmax − Xmin)/3) ≤ Xa − Xmin < (Xmax − Xmin) | Xa − Xb ≤ −5 | Dexfp = 0 |
| 126 | (2(Xmax − Xmin)/3) ≤ Xa − Xmin < (Xmax − Xmin) | −5 < Xa − Xb ≤ 0 | Dexfp = 0 |
| 127 | (2(Xmax − Xmin)/3) ≤ Xa − Xmin < (Xmax − Xmin) | 0 < Xa − Xb | Dexfp = 0 |
| 128 | (2(Xmax − Xmin)/3) ≤ Xa − Xmin < (Xmax − Xmin) | 0 < Xa − Xb | Dexfp = 0 |
| 129 | (2(Xmax − Xmin)/3) ≤ Xa − Xmin < (Xmax − Xmin) | 0 < Xa − Xb | Dexfp = 0 |
| 130 | (2(Xmax − Xmin)/3) ≤ Xa − Xmin < (Xmax − Xmin) | Xa − Xb ≤ −5 | 0 < Dexfp |
| 131 | (2(Xmax − Xmin)/3) ≤ Xa − Xmin < (Xmax − Xmin) | Xa − Xb ≤ −5 | 0 < Dexfp |
| 132 | (2(Xmax − Xmin)/3) ≤ Xa − Xmin < (Xmax − Xmin) | −5 < Xa − Xb ≤ 0 | 0 < Dexfp |
| 133 | (2(Xmax − Xmin)/3) ≤ Xa − Xmin < (Xmax − Xmin) | 0 < Xa − Xb | 0 < Dexfp ≤ 1/C * Wt |
| 134 | (2(Xmax − Xmin)/3) ≤ Xa − Xmin < (Xmax − Xmin) | 0 < Xa − Xb | 0 < Dexfp ≤ 1/C * Wt |
| 135 | (2(Xmax − Xmin)/3) ≤ Xa − Xmin < (Xmax − Xmin) | 0 < Xa − Xb | 0 < Dexfp ≤ 1/C * Wt |
| 136 | (2(Xmax − Xmin)/3) ≤ Xa − Xmin < (Xmax − Xmin) | 0 < Xa − Xb | 1/C * Wt < Dexfp ≤ 6/C * Wt |
| 137 | (2(Xmax − Xmin)/3) ≤ Xa − Xmin < (Xmax − Xmin) | 0 < Xa − Xb | 1/C * Wt < Dexfp ≤ 6/C * Wt |
| 138 | (2(Xmax − Xmin)/3) ≤ Xa − Xmin < (Xmax − Xmin) | 0 < Xa − Xb | 1/C * Wt < Dexfp ≤ 6/C * Wt |
| 139 | (2(Xmax − Xmin)/3) ≤ Xa − Xmin < (Xmax − Xmin) | 0 < Xa − Xb | 6/C * Wt < Dexfp |
| 140 | (2(Xmax − Xmin)/3) ≤ Xa − Xmin < (Xmax − Xmin) | 0 < Xa − Xb | 6/C * Wt < Dexfp |
| 141 | (2(Xmax − Xmin)/3) ≤ Xa − Xmin < (Xmax − Xmin) | 0 < Xa − Xb | 6/C * Wt < Dexfp |
| 142 | (2(Xmax − Xmin)/3) ≤ Xa − Xmin < (Xmax − Xmin) | Xa − Xb ≤ −3 | 0 < Dexfp |
| 143 | (2(Xmax − Xmin)/3) ≤ Xa − Xmin < (Xmax − Xmin) | −3 < Xa − Xb ≤ 0 | 0 < Dexfp ≤ 1/C * Wt |
| 144 | (2(Xmax − Xmin)/3) ≤ Xa − Xmin < (Xmax − Xmin) | −3 < Xa − Xb ≤ 0 | 1/C * Wt < Dexfp |
| 145 | (2(Xmax − Xmin)/3) ≤ Xa − Xmin < (Xmax − Xmin) | 0 < Xa − Xb | 0 < Dexfp ≤ 1/C * Wt |
| 146 | (2(Xmax − Xmin)/3) ≤ Xa − Xmin < (Xmax − Xmin) | 0 < Xa − Xb | 1/C * Wt < Dexfp |
| 147 | (2(Xmax − Xmin)/3) ≤ Xa − Xmin < (Xmax − Xmin) | Xa − Xb ≤ 0 | Dexfp = 0 |
| 148 | (2(Xmax − Xmin)/3) ≤ Xa − Xmin < (Xmax − Xmin) | 0 < Xa − Xb | Dexfp = 0 |
| 149 | 0 ≤ Xa − Xmax < 10 | Xa − Xb ≤ −4 | Dexfp = 0 |
| 150 | 0 ≤ Xa − Xmax < 10 | Xa − Xb ≤ −4 | Dexfp = 0 |
| 151 | 0 ≤ Xa − Xmax < 10 | −4 < Xa − Xb ≤ 1 | Dexfp = 0 |
| 152 | 0 ≤ Xa − Xmax < 10 | −4 < Xa − Xb ≤ 1 | Dexfp = 0 |

-continued

Glucose Algorithm Table

| | | | |
|---|---|---|---|
| 153 | $0 \leq Xa - Xmax < 10$ | $-4 < Xa - Xb \leq 1$ | $Dexfp = 0$ |
| 154 | $0 \leq Xa - Xmax < 10$ | $1 < Xa - Xb$ | $Dexfp = 0$ |
| 155 | $0 \leq Xa - Xmax < 10$ | $1 < Xa - Xb$ | $Dexfp = 0$ |
| 156 | $0 \leq Xa - Xmax < 10$ | $1 < Xa - Xb$ | $Dexfp = 0$ |
| 157 | $0 \leq Xa - Xmax < 10$ | $Xa - Xb \leq -4$ | $0 < Dexfp \leq 1/C * Wt$ |
| 158 | $0 \leq Xa - Xmax < 10$ | $Xa - Xb \leq -4$ | $1/C * Wt < Dexfp$ |
| 159 | $0 \leq Xa - Xmax < 10$ | $-4 < Xa - Xb \leq 0$ | $0 < Dexfp \leq 1/C * Wt$ |
| 160 | $0 \leq Xa - Xmax < 10$ | $-4 < Xa - Xb \leq 0$ | $1/C * Wt < Dexfp$ |
| 161 | $0 \leq Xa - Xmax < 10$ | $0 < Xa - Xb$ | $0 < Dexfp \leq 1/C * Wt$ |
| 162 | $0 \leq Xa - Xmax < 10$ | $0 < Xa - Xb$ | $0 < Dexfp \leq 1/C * Wt$ |
| 163 | $0 \leq Xa - Xmax < 10$ | $0 < Xa - Xb$ | $0 < Dexfp \leq 1/C * Wt$ |
| 164 | $0 \leq Xa - Xmax < 10$ | $0 < Xa - Xb$ | $1/C * Wt < Dexfp$ |
| 165 | $0 \leq Xa - Xmax < 10$ | $0 < Xa - Xb$ | $1/C * Wt < Dexfp$ |
| 166 | $0 \leq Xa - Xmax < 10$ | $0 < Xa - Xb$ | $1/C * Wt < Dexfp$ |
| 167 | $0 \leq Xa - Xmax < 10$ | $Xa - Xb \leq 0$ | $0 < Dexfp \leq 1/C * Wt$ |
| 168 | $0 \leq Xa - Xmax < 10$ | $Xa - Xb \leq 0$ | $1/C * Wt < Dexfp$ |
| 169 | $0 \leq Xa - Xmax < 10$ | $0 < Xa - Xb$ | $0 < Dexfp \leq 1/C * Wt$ |
| 170 | $0 \leq Xa - Xmax < 10$ | $0 < Xa - Xb$ | $1/C * Wt < Dexfp$ |
| 171 | $0 \leq Xa - Xmax < 10$ | $Xa - Xb \leq -3$ | $Dexfp = 0$ |
| 172 | $0 \leq Xa - Xmax < 10$ | $-3 < Xa - Xb$ | $Dexfp = 0$ |
| 173 | $10 \leq Xa - Xmax < 30$ | $Xa - Xb \leq -6$ | $Dexfp = 0$ |
| 174 | $10 \leq Xa - Xmax < 30$ | $Xa - Xb \leq -6$ | $Dexfp = 0$ |
| 175 | $10 \leq Xa - Xmax < 30$ | $-6 < Xa - Xb \leq 0$ | $Dexfp = 0$ |
| 176 | $10 \leq Xa - Xmax < 30$ | $-6 < Xa - Xb \leq 0$ | $Dexfp = 0$ |
| 177 | $10 \leq Xa - Xmax < 30$ | $-6 < Xa - Xb \leq 0$ | $Dexfp = 0$ |
| 178 | $10 \leq Xa - Xmax < 30$ | $0 < Xa - Xb$ | $Dexfp = 0$ |
| 179 | $10 \leq Xa - Xmax < 30$ | $0 < Xa - Xb$ | $Dexfp = 0$ |
| 180 | $10 \leq Xa - Xmax < 30$ | $0 < Xa - Xb$ | $Dexfp = 0$ |
| 181 | $10 \leq Xa - Xmax < 30$ | $Xa - Xb \leq -6$ | $0 < Dexfp \leq 2/C * Wt$ |
| 182 | $10 \leq Xa - Xmax < 30$ | $Xa - Xb \leq -6$ | $2/C * Wt < Dexfp \leq 6/C * Wt$ |
| 183 | $10 \leq Xa - Xmax < 30$ | $Xa - Xb \leq -6$ | $6/C * Wt < Dexfp$ |
| 184 | $10 \leq Xa - Xmax < 30$ | $-6 < Xa - Xb$ | $0 < Dexfp \leq 2/C * Wt$ |
| 185 | $10 \leq Xa - Xmax < 30$ | $-6 < Xa - Xb$ | $0 < Dexfp \leq 2/C * Wt$ |
| 186 | $10 \leq Xa - Xmax < 30$ | $-6 < Xa - Xb$ | $0 < Dexfp \leq 2/C * Wt$ |
| 187 | $10 \leq Xa - Xmax < 30$ | $-6 < Xa - Xb$ | $2/C * Wt < Dexfp$ |
| 188 | $10 \leq Xa - Xmax < 30$ | $-6 < Xa - Xb$ | $2/C * Wt < Dexfp$ |
| 189 | $10 \leq Xa - Xmax < 30$ | $-6 < Xa - Xb$ | $2/C * Wt < Dexfp$ |
| 190 | $10 \leq Xa - Xmax < 30$ | $Xa - Xb \leq 1$ | $0 < Dexfp \leq 1/C * Wt$ |
| 191 | $10 \leq Xa - Xmax < 30$ | $Xa - Xb \leq 1$ | $1/C * Wt < Dexfp$ |
| 192 | $10 \leq Xa - Xmax < 30$ | $1 < Xa - Xb$ | $0 < Dexfp \leq 1/C * Wt$ |
| 193 | $10 \leq Xa - Xmax < 30$ | $1 < Xa - Xb$ | $1/C * Wt < Dexfp$ |
| 194 | $10 \leq Xa - Xmax < 30$ | $Xa - Xb \leq -3$ | $Dexfp = 0$ |
| 195 | $10 \leq Xa - Xmax < 30$ | $-3 < Xa - Xb$ | $Dexfp = 0$ |
| 196 | $(Xa - Xmax) \geq 30$ | $Xa - Xb \leq -15$ | $Dexfp = 0$ |
| 197 | $(Xa - Xmax) \geq 30$ | $-15 < Xa - Xb$ | $Dexfp = 0$ |
| 198 | $(Xa - Xmax) \geq 30$ | $-15 < Xa - Xb$ | $Dexfp = 0$ |
| 199 | $(Xa - Xmax) \geq 30$ | $-15 < Xa - Xb$ | $Dexfp = 0$ |
| 200 | $(Xa - Xmax) \geq 30$ | $Xa - Xb \leq -15$ | $0 < Dexfp \leq 2/C * Wt$ |
| 201 | $(Xa - Xmax) \geq 30$ | $Xa - Xb \leq -15$ | $0 < Dexfp \leq 2/C * Wt$ |
| 202 | $(Xa - Xmax) \geq 30$ | $Xa - Xb \leq -15$ | $0 < Dexfp \leq 2/C * Wt$ |
| 203 | $(Xa - Xmax) \geq 30$ | $Xa - Xb \leq -15$ | $2/C * Wt < Dexfp$ |
| 204 | $(Xa - Xmax) \geq 30$ | $Xa - Xb \leq -15$ | $2/C * Wt < Dexfp$ |
| 205 | $(Xa - Xmax) \geq 30$ | $Xa - Xb \leq -15$ | $2/C * Wt < Dexfp$ |
| 206 | $(Xa - Xmax) \geq 30$ | $-15 < Xa - Xb$ | $0 < Dexfp \leq 2/C * Wt$ |
| 207 | $(Xa - Xmax) \geq 30$ | $-15 < Xa - Xb$ | $0 < Dexfp \leq 2/C * Wt$ |
| 208 | $(Xa - Xmax) \geq 30$ | $-15 < Xa - Xb$ | $0 < Dexfp \leq 2/C * Wt$ |
| 209 | $(Xa - Xmax) \geq 30$ | $-15 < Xa - Xb$ | $2/C * Wt < Dexfp$ |
| 210 | $(Xa - Xmax) \geq 30$ | $-15 < Xa - Xb$ | $2/C * Wt < Dexfp$ |
| 211 | $(Xa - Xmax) \geq 30$ | $-15 < Xa - Xb$ | $2/C * Wt < Dexfp$ |
| 212 | $(Xa - Xmax) \geq 30$ | $Xa - Xb \leq -15$ | $0 < Dexfp \leq 1/C * Wt$ |
| 213 | $(Xa - Xmax) \geq 30$ | $Xa - Xb \leq -15$ | $1/C * Wt < Dexfp$ |
| 214 | $(Xa - Xmax) \geq 30$ | $-15 < Xa - Xb$ | $0 < Dexfp \leq 2/C * Wt$ |
| 215 | $(Xa - Xmax) \geq 30$ | $-15 < Xa - Xb$ | $2/C * Wt < Dexfp$ |
| 216 | $(Xa - Xmax) \geq 30$ | $Xa - Xb \leq -15$ | $Dexfp = 0$ |
| 217 | $(Xa - Xmax) \geq 30$ | $-15 < Xa - Xb$ | $Dexfp = 0$ |
| 218 | If $(Xa \geq (Xmax + 20)$ mg/dL) and $(Xa < Xmax + 50$ mg/dL) and $Xa - Xb > -5$ then (give bolus dose insulin = (0.04 units * Wt) over 10 minutes | | |
| 219 | in addition to INSfn as calculated by algorithm If $(Xa \geq (Xmax + 50)$ mg/dL) and $(Xa < Xmax + 90$ mg/dL) and and $Xa - Xb > -15$ then (give bolus dose insulin = (0.04 units * Wt) over 10 minutes | | |
| 220 | in addition to INSfn as calculated by algorithm If $(Xa \geq Xmax + 90$ mg/dL) and $Xa - Xb > -20$ then (give bolus dose insulin = (0.08 units * Wt) over 10 minutes in addition to INSfn as calculated by algorithm | | |
| 221 | If $(Dexfn \geq DexSh)$ then $Dexfn = DexSh$ and activate alarm "Maximum Dextrose Infusion Rate" | | |
| 222 | If $(INSfn \geq INSSh)$ then $INSfn = INSSh$ and activate alarm "Maximum Insulin Infusion Rate" | | |
| 223 | $MIVFR = TIVFR - (Dexfn + (INSfn * Conc^{-1}))$ | | |

-continued

| | Glucose Algorithm Table | | | |
|---|---|---|---|---|
| | AND INSfp (units/hr) | THEN | Dexfn = (mL/hr) | AND INSfn = (units/hr) |
| 1 | 0 < INSfp | | 6/C * Wt | INSfp * 0.5 |
| 2 | 0 < INSfp ≤ 0.05 * Wt | | Dexfp * 1.7 | 0 |
| 3 | INSfp > 0.05 * Wt | | Dexfp * 1.7 | INSfp * 0.85 |
| 4 | 0 < INSfp < 0.05 * Wt | | Dexfp * 1.2 | 0 |
| 5 | INSfp ≥ 0.05 * Wt | | Dexfp * 1.2 | INSfp * 0.85 |
| 6 | 0 < INSfp < 0.05 * Wt | | Dexfp * 1.1 | 0 |
| 7 | INSfp ≥ 0.05 * Wt | | Dexfp * 1.1 | INSfp * 0.85 |
| 8 | 0 < INSfp ≤ 0.02 * Wt | | Dexfp * 1.3 | 0 |
| 9 | 0.02 * Wt < INSfp | | Dexfp * 1.3 | INSfp * 0.85 |
| 10 | 0 < INSfp ≤ 0.02 * Wt | | Dexfp * 1.2 | 0 |
| 11 | 0.02 * Wt < INSfp | | Dexfp * 1.2 | INSfp * 0.85 |
| 12 | 0 < INSfp ≤ 0.02 * Wt | | Dexfp * 1.1 | 0 |
| 13 | 0.02 * Wt < INSfp | | Dexfp * 1.1 | INSfp * 0.75 |
| 14 | INSfp = 0 | | Dexfp * 1.7 | INSfp |
| 15 | INSfp = 0 | | Dexfp * 1.4 | INSfp |
| 16 | INSfp = 0 | | Dexfp * 1.2 | INSfp |
| 17 | INSfp = 0 | | Dexfp * 1.5 | INSfp |
| 18 | INSfp = 0 | | Dexfp * 1.3 | INSfp |
| 19 | INSfp = 0 | | Dexfp * 1.2 | INSfp |
| 20 | INSfp = 0 | | 6/C * Wt | INSfp |
| 21 | 0 < INSfp ≤ 0.01 * Wt | | 3/C * Wt | 0 |
| 22 | 0.01 * Wt < INSfp ≤ 0.1 * Wt | | 3/C * Wt | INSfp * 0.85 |
| 23 | 0.1 * Wt < INSfp | | 3/C * Wt | INSfp * 0.9 |
| 24 | 0 < INSfp ≤ 0.01 * Wt | | Dexfp | 0 |
| 25 | 0.01 * Wt < INSfp ≤ 0.1 * Wt | | Dexfp | INSfp * 0.9 |
| 26 | 0.1 * Wt < INSfp | | Dexfp | INSfp * 0.85 |
| 27 | 0 < INSfp ≤ 0.01 * Wt | | Dexfp * 1.5 | 0 |
| 28 | 0.01 * Wt < INSfp ≤ 0.1 * Wt | | Dexfp * 1.5 | INSfp * 0.8 |
| 29 | 0.1 * Wt < INSfp | | Dexfp * 1.5 | INSfp * 0.9 |
| 30 | 0 < INSfp ≤ 0.01 * Wt | | Dexfp * 1.3 | 0 |
| 31 | 0.01 * Wt < INSfp ≤ 0.1 * Wt | | Dexfp * 1.3 | INSfp * 0.8 |
| 32 | 0.1 * Wt < INSfp | | Dexfp * 1.3 | INSfp * 0.9 |
| 33 | 0 < INSfp ≤ 0.01 * Wt | | Dexfp * 1.2 | 0 |
| 34 | 0.01 * Wt < INSfp ≤ 0.1 * Wt | | Dexfp * 1.1 | INSfp * 0.8 |
| 35 | 0.1 * Wt < INSfp | | Dexfp * 1.1 | INSfp * 0.9 |
| 36 | 0 < INSfp ≤ 0.01 * Wt | | Dexfp * 1.1 | 0 |
| 37 | 0.01 * Wt < INSfp ≤ 0.1 * Wt | | Dexfp * 1.1 | INSfp * 0.85 |
| 38 | 0.1 * Wt < INSfp | | Dexfp * 1.1 | INSfp * 0.95 |
| 39 | 0 < INSfp | | Dexfp * 1.1 | INSfp * 0.95 |
| 40 | INSfp = 0 | | Dexfp * 1.5 | INSfp |
| 41 | INSfp = 0 | | Dexfp * 1.3 | INSfp |
| 42 | INSfp = 0 | | Dexfp * 1.1 | INSfp |
| 43 | INSfp = 0 | | Dexfp * 1.1 | INSfp |
| 44 | INSfp = 0 | | 3/C * Wt | INSfp |
| 45 | INSfp = 0 | | 2/C * Wt | INSfp |
| 46 | 0 < INSfp ≤ 0.01 * Wt | | 2/C * Wt | 0 |
| 47 | 0.01 * Wt < INSfp ≤ 0.1 * Wt | | 2/C * Wt | INSfp * 0.8 |
| 48 | 0.1 * Wt < INSfp | | 2/C * Wt | INSfp * 0.9 |
| 49 | 0 < INSfp ≤ 0.01 * Wt | | Dexfp | 0 |
| 50 | 0.01 * Wt < INSfp ≤ 0.1 * Wt | | Dexfp | INSfp * 0.85 |
| 51 | 0.1 * Wt < INSfp | | Dexfp | INSfp * 0.95 |
| 52 | 0 < INSfp ≤ 0.01 * Wt | | Dexfp * 1.5 | 0 |
| 53 | 0.01 * Wt < INSfp ≤ 0.1 * Wt | | Dexfp * 1.5 | INSfp * 0.85 |
| 54 | 0.1 * Wt < INSfp | | Dexfp * 1.5 | INSfp * 0.9 |
| 55 | 0 < INSfp ≤ 0.01 * Wt | | Dexfp * 1.25 | 0 |
| 56 | 0.01 * Wt < INSfp ≤ 0.1 * Wt | | Dexfp * 1.25 | INSfp * 0.85 |
| 57 | 0.1 * Wt < INSfp | | Dexfp * 1.25 | INSfp * 0.9 |
| 58 | 0 < INSfp ≤ 0.01 * Wt | | Dexfp * 1.1 | 0 |
| 59 | 0.01 * Wt < INSfp ≤ 0.1 * Wt | | Dexfp * 1.1 | INSfp * 0.85 |
| 60 | 0.1 * Wt < INSfp | | Dexfp * 1.1 | INSfp * 0.9 |
| 61 | 0 < INSfp ≤ 0.01 * Wt | | Dexfp | 0 |
| 62 | 0.01 * Wt < INSfp | | Dexfp | INSfp * 0.95 |
| 63 | INSfp = 0 | | Dexfp * 1.5 | INSfp |
| 64 | INSfp = 0 | | Dexfp * 1.25 | INSfp |
| 65 | INSfp = 0 | | Dexfp * 1.1 | INSfp |
| 66 | INSfp = 0 | | Dexfp | INSfp |
| 67 | INSfp = 0 | | 2/C * Wt | INSfp |
| 68 | INSfp = 0 | | Dexfp | INSfp |
| 69 | 0 < INSfp ≤ 0.01 * Wt | | Dexfp | 0 |
| 70 | 0.01 * Wt < INSfp < 0.1 * Wt | | Dexfp | INSfp * 0.85 |
| 71 | 0.1 * Wt < INSfp | | Dexfp | INSfp * 0.9 |
| 72 | 0 < INSfp | | Dexfp | INSfp |
| 73 | 0 < INSfp | | Dexfp | INSfp * 1.05 |

-continued

Glucose Algorithm Table

| | | | |
|---|---|---|---|
| 74 | 0 < INSfp ≤ 0.01 * Wt | Dexfp * 1.5 | 0 |
| 75 | 0.01 * Wt < INSfp ≤ 0.1 * Wt | Dexfp * 1.5 | INSfp * 0.85 |
| 76 | 0.1 * Wt < INSfp | Dexfp * 1.5 | INSfp * 0.9 |
| 77 | 0 < INSfp ≤ 0.01 * Wt | Dexfp * 1.25 | 0 |
| 78 | 0.01 * Wt < INSfp ≤ 0.1 * Wt | Dexfp * 1.25 | INSfp * 0.85 |
| 79 | 0.1 * Wt < INSfp | Dexfp * 1.25 | INSfp * 0.9 |
| 80 | 0 < INSfp ≤ 0.01 * Wt | Dexfp * 1.1 | 0 |
| 81 | 0.01 * Wt < INSfp ≤ 0.1 * Wt | Dexfp * 1.1 | INSfp * 0.85 |
| 82 | 0.1 * Wt < INSfp | Dexfp * 1.1 | INSfp * 0.9 |
| 83 | 0 < INSfp | Dexfp | INSfp |
| 84 | 0 < INSfp | 0 | INSfp * 1.05 |
| 85 | 0 < INSfp | Dexfp * 0.95 | INSfp * 1.05 |
| 86 | INSfp = 0 | Dexfp * 1.5 | INSfp |
| 87 | INSfp = 0 | Dexfp * 1.25 | INSfp |
| 88 | INSfp = 0 | Dexfp * 1.1 | INSfp |
| 89 | INSfp = 0 | Dexfp | INSfp |
| 90 | INSfp = 0 | 0 | 0.01 * Wt |
| 91 | INSfp = 0 | Dexfp * 0.95 | 0.01 * Wt |
| 92 | INSfp = 0 | 2/C * Wt | INSfp |
| 93 | INSfp = 0 | Dexfp | INSfp |
| 94 | INSfp = 0 | Dexfp | 0.01 * Wt |
| 95 | 0 < INSfp ≤ 0.01 * Wt | Dexfp | 0 |
| 96 | 0.01 * Wt < INSfp ≤ 0.1 * Wt | Dexfp | INSfp * 0.9 |
| 97 | 0.1 * Wt < INSfp | Dexfp | INSfp * 0.95 |
| 98 | 0 < INSfp | Dexfp | INSfp |
| 99 | 0 < INSfp ≤ 0.01 * Wt | Dexfp | INSfp * 1.5 |
| 100 | 0.01 * Wt < INSfp ≤ 0.1 * Wt | Dexfp | INSfp * 1.15 |
| 101 | 0.1 * Wt < INSfp | Dexfp | INSfp * 1.1 |
| 102 | 0 < INSfp ≤ 0.01 * Wt | Dexfp | 0 |
| 103 | 0.01 * Wt < INSfp ≤ 0.1 * Wt | Dexfp | INSfp * 0.9 |
| 104 | 0.1 * Wt < INSfp | Dexfp | INSfp * 0.95 |
| 105 | 0 < INSfp | Dexfp | INSfp |
| 106 | 0 < INSfp ≤ 0.01 * Wt | 0 | INSfp * 1.5 |
| 107 | 0.01 * Wt < INSfp ≤ 0.1 * Wt | 0 | INSfp * 1.15 |
| 108 | 0.1 * Wt < INSfp | 0 | INSfp * 1.05 |
| 109 | 0 < INSfp ≤ 0.01 * Wt | Dexfp * 0.85 | INSfp * 1.5 |
| 110 | 0.01 * Wt < INSfp ≤ 0.1 * Wt | Dexfp * 0.85 | INSfp * 1.15 |
| 111 | 0.1 * Wt < INSfp | Dexfp * 0.85 | INSfp * 1.05 |
| 112 | 0 < INSfp ≤ 0.01 * Wt | Dexfp * 0.9 | INSfp * 1.5 |
| 113 | 0.01 * Wt < INSfp ≤ 0.0 * Wt | Dexfp * 0.9 | INSfp * 1.15 |
| 114 | 0.1 * Wt < INSfp | Dexfp * 0.9 | INSfp * 1.05 |
| 115 | INSfp = 0 | Dexfp * 1.3 | INSfp |
| 116 | INSfp = 0 | Dexfp * 1.1 | INSfp |
| 117 | INSfp = 0 | Dexfp * 1.05 | INSfp |
| 118 | INSfp = 0 | Dexfp | INSfp |
| 119 | INSfp = 0 | 0 | 0.02 * Wt |
| 120 | INSfp = 0 | Dexfp * 0.9 | 0.02 * Wt |
| 121 | INSfp = 0 | Dexfp | INSfp |
| 122 | INSfp = 0 | Dexfp | 0.02 * Wt |
| 123 | 0 < INSfp ≤ 0.01 * Wt | Dexfp | 0 |
| 124 | 0.01 * Wt < INSfp ≤ 0.1 * Wt | Dexfp | INSfp * 0.85 |
| 125 | 0.1 * Wt < INSfp | Dexfp | INSfp * 0.9 |
| 126 | 0 < INSfp | Dexfp | INSfp |
| 127 | 0 < INSfp ≤ 0.02 * Wt | Dexfp | INSfp * 1.5 |
| 128 | 0.02 * Wt < INSfp ≤ 0.1 * Wt | Dexfp | INSfp * 1.15 |
| 129 | 0.1 * Wt < INSfp | Dexfp | INSfp * 1.05 |
| 130 | 0 < INSfp ≤ 0.01 * Wt | Dexfp | 0 |
| 131 | 0.01 * Wt < INSfp | Dexfp | INSfP * 0.95 |
| 132 | 0 < INSfp | Dexfp | INSfp |
| 133 | 0 < INSfp ≤ 0.01 * Wt | 0 | INSfp * 1.5 |
| 134 | 0.01 * Wt < INSfp ≤ 0.1 * Wt | 0 | INSfp * 1.15 |
| 135 | 0.1 * Wt < INSfp | 0 | INSfp * 1.05 |
| 136 | 0 < INSfp ≤ 0.01 * Wt | Dexfp * 0.8 | INSfp * 1.5 |
| 137 | 0.01 * Wt < INSfp ≤ 0.1 * Wt | Dexfp * 0.8 | INSfp * 1.15 |
| 138 | 0.1 * Wt < INSfp | Dexfp * 0.8 | INSfp * 1.05 |
| 139 | 0 < INSfp ≤ 0.01 * Wt | Dexfp * 0.85 | INSfp * 1.5 |
| 140 | 0.01 * Wt < INSfp ≤ 0.1 * Wt | Dexfp * 0.85 | INSfp * 1.15 |
| 141 | 0.1 * Wt < INSfp | Dexfp * 0.85 | INSfp * 1.05 |
| 142 | INSfp = 0 | Dexfp | INSfp |
| 143 | INSfp = 0 | 0 | INSfp |
| 144 | INSfp = 0 | Dexfp * 0.95 | INSfp |
| 145 | INSfp = 0 | 0 | 0.02 * Wt |
| 146 | INSfp = 0 | Dexfp * 0.9 | 0.02 * Wt |
| 147 | INSfp = 0 | Dexfp | INSfp |
| 148 | INSfp = 0 | Dexfp | 0.02 * Wt |
| 149 | 0 < INSfp ≤ 0.1 * Wt | Dexfp | INSfp * 0.9 |
| 150 | 0.1 * Wt < INSfp | Dexfp | INSfp * 0.95 |

| | Glucose Algorithm Table | | |
|---|---|---|---|
| 151 | 0 < INSfp ≤ 0.02 * Wt | Dexfp | INSfp * 1.3 |
| 152 | 0.02 * Wt < INSfp ≤ 0.1 * Wt | Dexfp | INSfp * 1.15 |
| 153 | 0.1 * Wt < INSfp | Dexfp | INSfp * 1.05 |
| 154 | 0 < INSfp ≤ 0.01 * Wt | Dexfp | INSfp * 1.5 |
| 155 | 0.01 * Wt < INSfp ≤ 0.1 * Wt | Dexfp | INSfp * 1.3 |
| 156 | 0.1 * Wt < INSfp | Dexfp | INSfp * 1.1 |
| 157 | 0 < INSfp | 0 | INSfp |
| 158 | 0 < INSfp | Dexfp * 0.95 | INSfp * 1.05 |
| 159 | 0 < INSfp | 0 | INSfp * 1.05 |
| 160 | 0 < INSfp | Dexfp * 0.9 | INSfp * 1.05 |
| 161 | 0 < INSfp ≤ 0.01 * Wt | 0 | INSfp * 1.5 |
| 162 | 0.01 * Wt < INSfp ≤ 0.1 * Wt | 0 | INSfp * 1.3 |
| 163 | 0.1 * Wt < INSfp | 0 | INSfp * 1.1 |
| 164 | 0 < INSfp ≤ 0.01 * Wt | Dexfp * 0.8 | INSfP * 1.5 |
| 165 | 0.01 * Wt < INSfp ≤ 0.1 * Wt | Dexfp * 0.8 | INSfp * 1.3 |
| 166 | 0.1 * Wt < INSfp | Dexfp * 0.8 | INSfp * 1.1 |
| 167 | INSfp = 0 | 0 | INSfp |
| 168 | INSfp = 0 | Dexfp * 0.9 | INSfp |
| 169 | INSfp = 0 | 0 | 0.02 * Wt |
| 170 | INSfp = 0 | Dexfp * 0.8 | 0.02 * Wt |
| 171 | INSfp = 0 | Dexfp | INSfp |
| 172 | INSfp = 0 | Dexfp | 0.02 * Wt |
| 173 | 0 < INSfp ≤ 0.1 * Wt | Dexfp | INSfp * 0.9 |
| 174 | 0.1 * Wt < INSfp | Dexfp | INSfp * 0.95 |
| 175 | 0 < INSfp ≤ 0.02 * Wt | Dexfp | INSfp * 1.4 |
| 176 | 0.02 * Wt < INSfp ≤ 0.1 * Wt | Dexfp | INSfp * 1.2 |
| 177 | 0.1 * Wt < INSfp | Dexfp | INSfp * 1.1 |
| 178 | 0 < INSfp ≤ 0.02 * Wt | Dexfp | INSfp * 1.5 |
| 179 | 0.02 * Wt < INSfp ≤ 0.1 * Wt | Dexfp | INSfp * 1.3 |
| 180 | 0.1 * Wt < INSfp | Dexfp | INSfp * 1.1 |
| 181 | 0 < INSfp | 0 | INSfp * 1.1 |
| 182 | 0 < INSfp | Dexfp * 0.8 | INSfp * 1.1 |
| 183 | 0 < INSfp | Dexfp * 0.9 | INSfp * 1.1 |
| 184 | 0 < INSfp ≤ 0.02 * Wt | 0 | INSfp * 1.5 |
| 185 | 0.02 * Wt < INSfp ≤ 0.1 * Wt | 0 | INSfp * 1.3 |
| 186 | 0.1 * Wt < INSfp | 0 | INSfp * 1.1 |
| 187 | 0 < INSfp ≤ 0.02 * Wt | Dexfp * 0.8 | INSfp * 1.5 |
| 188 | 0.02 * Wt < INSfp ≤ 0.1 * Wt | Dexfp * 0.8 | INSfp * 1.3 |
| 189 | 0.1 * Wt < INSfp | Dexfp * 0.8 | INSfp * 1.1 |
| 190 | INSfp = 0 | 0 | 0.03 * Wt |
| 191 | INSfp = 0 | Dexfp * 0.8 | 0.03 * Wt |
| 192 | INSfp = 0 | 0 | 0.03 * Wt |
| 193 | INSfp = 0 | Dexfp * 0.7 | 0.03 * Wt |
| 194 | INSfp = 0 | Dexfp | 0.02 * Wt |
| 195 | INSfp = 0 | Dexfp | 0.03 * Wt |
| 196 | 0 < INSfp | Dexfp | INSfp |
| 197 | 0 < INSfp ≤ 0.02 * Wt | Dexfp | INSfp * 1.6 |
| 198 | 0.02 * Wt < INSfp ≤ 0.1 * Wt | Dexfp | INSfp * 1.4 |
| 199 | 0.1 * Wt < INSfp | Dexfp | INSfp * 1.1 |
| 200 | 0 < INSfp ≤ 0.02 * Wt | 0 | INSfp * 1.5 |
| 201 | 0.02 * Wt < INSfp ≤ 0.1 * Wt | 0 | INSfp * 1.2 |
| 202 | 0.1 * Wt < INSfp | 0 | INSfp * 1.05 |
| 203 | 0 < INSfp ≤ 0.02 * Wt | Dexfp * 0.9 | INSfp * 1.5 |
| 204 | 0.02 * Wt < INSfp ≤ 0.1 * Wt | Dexfp * 0.9 | INSfp * 1.2 |
| 205 | 0.1 * Wt < INSfp | Dexfp * 0.9 | INSfp * 1.05 |
| 206 | 0 < INSfp ≤ 0.02 * Wt | 0 | INSfp * 1.7 |
| 207 | 0.02 * Wt < INSfp ≤ 0.1 * Wt | 0 | INSfp * 1.3 |
| 208 | 0.1 * Wt < INSfp | 0 | INSfp * 1.1 |
| 209 | 0 < INSfp ≤ 0.02 * Wt | Dexfp * 0.8 | INSfp * 1.7 |
| 210 | 0.02 * Wt < INSfp ≤ 0.1 * Wt | Dexfp * 0.8 | INSfp * 1.3 |
| 211 | 0.1 * Wt < InSfp | Dexfp * 0.75 | INSfp * 1.1 |
| 212 | INSfp = 0 | 0 | 0.01 * Wt |
| 213 | INSfp = 0 | Dexfp * 0.9 | 0.01 * Wt |
| 214 | INSfp = 0 | 0 | 0.03 * Wt |
| 215 | INSfp = 0 | Dexfp * 0.7 | 0.03 * Wt |
| 216 | INSfp = 0 | Dexfp | 0.01 * Wt |
| 217 | INSfp = 0 | Dexfp | 0.03 * Wt |
| 218 | If ($X_a$ ≥ ($X_{max}$ + 20) mg/dL) and ($X_a$ < $X_{max}$ + 50 mg/dL) and $X_a$ − $X_b$ > −5 then (give bolus dose insulin = (0.04 units * Wt) over 10 minutes | | |
| 219 | in addition to INSfn as calculated by algorithm If ($X_a$ ≥ ($X_{max}$ + 50) mg/dL) and ($X_a$ < $X_{max}$ + 90 mg/dL) and and $X_a$ − $X_b$ > −15 then (give bolus dose insulin = (0.04 units * Wt) over 10 minutes | | |

| Glucose Algorithm Table |
|---|
| 220 in addition to INSfn as calculated by algorithm<br>If (Xa ≥ Xmax + 90 mg/dL) and (Xa − Xb > −20 then<br>(give bolus dose insulin = (0.08 units * Wt) over 10 minutes in<br>addition to INSfn as calculated by algorithm<br>221 If (Dexfn ≥ DexSh) then Dexfn = DexSh and activate alarm<br>"Maximum Dextrose Infusion Rate"<br>222 If (INSfn ≥ INSSh) then INSfn = INSSh and activate alarm<br>"Maximum Insulin Infusion Rate"<br>223 MIVFR = TIVFR − (Dexfn + (INSfn * Conc$^{-1}$) |

OSMOLALITY ALGORITHM—Definitions and Charactersistes

1. Yt=Osmolality value measured at time t with time measured in seconds
2. Ya=Average osmolality value measured over previous 10 minutes
3. Ya=(Y0+Y30+Y60+Y90+Y120+Y150+Y180+Y210+Y240+Y270+Y300+Y330+Y360+Y390+Y420+Y450+Y480+Y510+Y540+Y570)/20, whereby these are osmolality values measured every 30 seconds over the previous 10 minute period
4. For all values of Yt whereby Yt<Ya−2 standard deviations or >Ya+2 standard deviations, then Yt not included in calculation of Ya
5. Yb=Average osmolality value measured over 10 minute period immediately prior to Ya.
6: OsmS1=Set point for "Low End of Osmolality Range"
7. OsmSh=Set point for "High End of Osmolality Range"
8. HTSSh=Set point for "Maximum Hypertonic Saline Infusion Rate"
9. HTSf=Hypertonic saline flow rate in mL/hour
10. HTSfp=Hypertonic saline flow rate in mL/hour over previous 10 minutes
11. HTSfn=Hypertonic saline flow rate in mL/hour over next 10 minutes
12. Wt=Patients weight in Kilograms
13. On start up initial HTSf set by nurse/physician=HTSfp
14. Algorithm begins on start up after two average (Ya & Yb) osmolality values obtained.
15. Osmolality average values calculated and algorithm adjusts HTSfn every 10 minutes (12:00, 12:10, 12:20, etc)
16. Temp=intravascular temperature measured by thermistor
17. Nurse/Physician selects Hypertonic Saline concentration on start up (3%, 7.5%, etc) and in calculating initial hypertonic saline infusion rate entered hypertonic saline concentration number (3, 7.5, etc) is considered variable "Z".
18. If OsmS1<270 mOsm/Kg then OsmS1=270 mOsm/Kg
19. If OsmSh>360 mOsm/Kg then OsmSh=360 mOsm/Kg
20. If (OsmSh−Osms1)<10 mOsm/Kg then OsmS1=OsmSh−10 mOsm/Kg
21. HTSSh=Maximum hypertonic saline rate in mL/hour set by nurse/physician
22. MIVFR=Maintenance intravenous fluid rate calculated by algorithm
23. TIVFR=Total intravenous fluid rate set by nurse/physician
24. Osmolality algorithm assumes two separate infusions will be used which will consist of: 1) Hypertonic saline solution, 2) Maintenance intravenous fluid
25. Osmolality value as measured by conductivity sensor on catheter will be calibrated against blood osmolality obtained from patient and measured in hospital laboratory at least every 12 hours
26. Alarm "High Osmolality, Hypertonic Saline Off, Assess Patient" displayed when measured osmolality is >(OsmSh+5 mOsm/Kg) and Hypertonic Saline flow is zero. Nurse is to assess patient including: intake & output, insensible fluid losses and composition of electrolytes in all infused fluids including infused medications Alarm Events 1. "Low Osmolality"–Alarm sounded when measured Osmolality is less than "Lower Osmolality Alarm Limit" which may be the same or less than OsmS1. This lower Osmolality alarm limit is set by the nurse/physician.
2. "High Osmolality"—Alarm sounded when measured Osmolality is greater than "Upper Osmolality Alarm Limit" which may be the same or greater than OsmSh. This upper Osmolality alarm limit is set by the nurse/physician.
3. "Maximum Hypertonic Saline Infusion Rate"—Alarm sounded when HTSfn is greater than HTSSh indicating the algorithm is calling for a hypertonic saline infusion rate that is greater than the maximal allowed rate.
4. "High Osmolality, Hypertonic Saline Off, Assess Patient"–Alarm sounded when measured Osmolality is >(OsmSh+5 mOsm/Kg) and Hypertonic Saline flow is zero.
5. "Check Catheter Position"–Alarm sounded when measured Osmolality is <"Lower Osmolality Alarm Limit" and temperature is <32 degrees celcius.

Osmolality Algorithm—User Sets Low & High Osmolality to Determine Target Range

1. If (Ya<OsmS1−5 mOsm/Kg) and (Ya−Yb<−2 mOsm/Kg) and (HTSfp=0 mL/hour) then HTSfn=(0.2*Wt*3/Z) mL/hour
2. If (Ya<OsmS1−5 mOsm/Kg) and (Ya−Yb<−2 mOsm/Kg) and (HTSfp>0 mL/hour) and (HTSfp−(0.2*Wt*3/Z) mL/hour) then HTSfn=(HTSfp*1.4)
3. If (Ya<OsmS1−5 mOsm/Kg) and (Ya−Yb<−2 mOsm/Kg) and (HTSfp>(0.2*Wt*3/Z) mL/hour) and (HTSfp≤(0.6*Wt*3/Z) mL/hour) then HTSfn=(HTSfp*1.1)
4. If (Ya<OsmS1−5 mOsm/Kg) and (Ya−Yb<−2 mOsm/Kg) and (HTSfp>(0.6*Wt*3/Z) mL/hour) and (HTSfp≤(1*Wt*3/Z) mL/hour) then HTSfn=(HTSfp*1.05)
5. If (Ya<OsmS1−5 mOsm/Kg) and (Ya−Yb<−2 mOsm/Kg) and (HTSfp>(1*Wt*3/Z) mL/hour) then HTSfn=(HTSfp*1.04)
6. If (Ya<OsmS1−5 mOsm/Kg) and (Ya−Yb≥−2 mOsm/Kg) and (Ya−Yb<2 mOsm/Kg) and (HTSfp=0 mL/hour) then HTSfn=(0.12*Wt*3/Z) mL/hour
7. If (Ya<OsmS1−5 mOsm/Kg) and (Ya−Yb≥−2 mOsm/Kg) and (Ya−Yb<2 mOsm/Kg) and (HTSfp>0 mL/hour) and (HTSfp≤(0.2*Wt*3/Z) mL/hour) then HTSfn=(HTSfp*1.25)
8. If (Ya<OsmS1−5 mOsm/Kg) and (Ya−Yb≥−2 mOsm/Kg) and (Ya−Yb<2 mOsm/Kg) and (HTSfp>(0.2*Wt*3/Z) mL/hour) and (HTSfp≤(0.6*Wt*3/Z) mL/hour) then HTSfn=(HTSfp 1.07)

9. If (Ya<OsmS1−5 mOsm/Kg) and (Ya−Yb≥−2 mOsm/Kg) and (Ya−Yb<2 mOsm/Kg) and (HTSfp>(0.6*Wt*3/Z) mL/hour) and (HTSfp≤(1*Wt*3/Z) mL/hour) then HTSfn=(HTSfp*1.04)

10. If (Ya<OsmS1−5 mOsm/Kg) and (Ya−Yb≥−2 mOsm/Kg) and (Ya−Yb<2 mOsm/Kg) and (HTSfp>(1*Wt*3/Z) mL/hour) then HTSfn=(HTSfp*1.03)

11. If (Ya<OsmS1−5 mOsm/Kg) and (Ya−Yb≥2 mOsm/Kg) and (HTSfp=0 mL/hour) then HTSfn=(0.08*Wt*3/Z) mL/hour 12. If (Ya<OsmS1−5 mOsm/Kg) and (Ya−Yb≥2 mOsm/Kg) and (HTSfp>0 mL/hour) then HTSfn=HTSfp 13. If (Ya≥OsmS1−5 mOsm/Kg) and (Ya<OsmS1) and (Ya−Yb<−2 mOsm/Kg) and (HTSfp=0 mL/hour) then HTSfn=(0.15*Wt*3/Z) mL/hour 14. If (Ya≥OsmS1−5 mOsm/Kg) and (Ya<OsmS1) and (Ya−Yb<−2 mOsm/Kg) and (HTSfp>0 mL/hour) and (HTSfp≤(0.2*Wt*3/Z) mL/hour) then HTSfn=(HTSfp*1.3)

15. If (Ya≥OsmS1−5 mOsm/Kg) and (Ya<OsmS1) and (Ya−Yb<−2 mOsm/Kg) and (HTSfp>(0.2*Wt*3/Z) mL/hour) and (HTSfp≤(0.6*Wt*3/Z) mL/hour) then HTSfn=(HTSfp*1.07)

16. If (Ya≥OsmS1−5 mOsm/Kg) and (Ya<OsmS1) and (Ya−Yb<−2 mOsm/Kg) and (HTSfp>(0.6*Wt*3/Z) mL/hour) and (HTSfp≤(1*Wt*3/Z) mL/hour) then HTSfn=(HTSfp*1.04)

17. If (Ya≥OsmS1−5 mOsm/Kg) and (Ya<OsmS1) and (Ya−Yb<−2 mOsm/Kg) and (HTSfp>(1*Wt*3/Z) mL/hour) then HTSfn=(HTSfp*1.03)

18. If (Ya≤OsmS1−5 mOsm/Kg) and (Ya<OsmS1) and (Ya−Yb≥−2 mOsm/Kg) and (Ya−Yb<2 mOsm/Kg) and (HTSfp=0 mL/hour) then HTSfn=(0.08*Wt*3/Z) mL/hour 19. If (Ya≥OsmS1−5 mOsm/Kg) and (Ya<OsmS1) and (Ya−Yb≥−2 mOsm/Kg) and (Ya−Yb<2 mOsm/Kg) and (HTSfp>0 mL/hour) and (HTSfp<(0.2*Wt*3/Z) mL/hour) then HTSfn=(HTSfp*1.2)

20. If (Ya≥OsmS1−5 mOsm/Kg) and (Ya<OsmS1) and (Ya−Yb≥−2 mOsm/Kg) and (Ya−Yb<2 mOsm/Kg) and (HTSfp>(0.2*Wt*3/Z) mL/hour) and (HTSfp<(0.6*Wt*3/Z) mL/hour) then HTSfn=(HTSfp*1.05)

21. If (Ya≥OsmS1−5 mOsm/Kg) and (Ya<OsmS1) and (Ya−Yb≥−2 mOsm/Kg) and (Ya−Yb<2 mOsm/Kg) and (HTSfp>(0.6*Wt*3/Z) mL/hour) and (HTSfp<(1*Wt*3/Z) mL/hour) then HTSfn=(HTSfp*1.03)

22. If (Ya≥OsmS1−5 mOsm/Kg) and (Ya<OsmS1) and (Ya−Yb≥−2 mOsm/Kg) and (Ya−Yb<2 mOsm/Kg) and (HTSfp>(1*Wt*3/Z) mL/hour) then HTSfn=(HTSfp*1.02)

23. If (Ya>OsmS1−5 mOsm/Kg) and (Ya<OsmS1) and (Ya−Yb≥2 mOsm/Kg) and (HTSfp=0 mL/hour) then HTSfn=HTSfp 24. If (Ya>OsmS1−5 mOsm/Kg) and (Ya<OsmS1) and (Ya−Yb≥2 mOsm/Kg) and (HTSfp>0 mL/hour) then HTSfn=HTSfp 25. If (Ya≥OsmS1) and (Ya<OsmS1+((OsmSh−OsmS1)/3)) and (Ya−Yb<−2 mOsm/Kg) and (HTSfp=0 mL/hour) then HTSfn=(0.1*Wt*3/Z) mL/hour 26. If (Ya≥OsmS1) and (Ya<OsmS1+((OsmSh−OsmS1)/3)) and (Ya−Yb<−2 mOsm/Kg) and (HTSfp>0 mL/hour) and (HTSfp≤(0.2*Wt*3/Z) mL/hour) then HTSfn=(HTSfp*1.24)

27. If (Ya≥OsmS1) and (Ya<OsmS1+((OsmSh−OsmS1)/3)) and (Ya−Yb<−2 mOsm/Kg) and (HTSfp>(0.2*Wt*3/Z) mL/hour) and (HTSfp≤(0.6*Wt*3/Z) mL/hour) then HTSfn=(HTSfp*1.06)

28. If (Ya>OsmS1) and (Ya<OsmS1+((OsmSh−OsmS1)/3)) and (Ya−Yb<−2 mOsm/Kg) and (HTSfp>(0.6*Wt*3/Z) mL/hour) and (HTSfp≤(1*Wt*3/Z) mL/hour) then HTSfn=(HTSfp*1.03)

29. If (Ya≥OsmS1) and (Ya<OsmS1+((OsmSh−OsmS1)/3)) and (Ya−Yb<−2 mOsm/Kg) and (HTSfp>(1*Wt*3/Z) mL/hour) then HTSfn=(HTSfp*1.02)

30. If (Ya≥OsmS1) and (Ya<OsmS1+((OsmSh−OsmS1)/3)) and (Ya−Yb≥−2 mOsm/Kg) and (Ya−Yb<2 mOsm/Kg) and (HTSfp=0 mL/hour) then HTSfn=(0.06*Wt*3/Z) mL/hour 31. If (Ya≥OsmS1) and (Ya<OsmS1+((OsmSh−OsmS1)/3)) and (Ya−Yb≥−2 mOsm/Kg) and (Ya−Yb<2 mOsm/Kg) and (HTSfp>0 mL/hour) and (HTSfp≤(0.2*Wt*3/Z) mL/hour) then HTSfn=(HTSfp*1.15)

32. If (Ya≥OsmS1) and (Ya<OsmS1+((OsmSh−OsmS1)/3)) and (Ya−Yb≥−2 mOsm/Kg) and (Ya−Yb<2 mOsm/Kg) and (HTSfp>(0.2*Wt*3/Z) mL/hour) and (HTSfp≤(0.6*Wt*3/Z) mL/hour) then HTSfn=(HTSfp*1.04)

33. If (Ya≥OsmS1) and (Ya<OsmS1+((OsmSh−OsmS1)/3)) and (Ya−Yb≥−2 mOsm/Kg) and (Ya−Yb<2 mOsm/Kg) and (HTSfp>(0.6*Wt*3/Z) mL/hour) and (HTSfp≤(1*Wt*3/Z) mL/hour) then HTSfn=(HTSfp*1.02)

34. If (Ya≥OsmS1) and (Ya<OsmS1+((OsmSh−OsmS1)/3)) and (Ya−Yb≥−2 mOsm/Kg) and (Ya−Yb<2 mOsm/Kg) and (HTSfp>(1*Wt*3/Z) mL/hour) then HTSfn=(HTSfp*1.02)

35. If (Ya≥OsmS1) and (Ya<OsmS1+((OsmSh−OsmS1)/3)) and (Ya−Yb≥2 mOsm/Kg) and (HTSfp=0 mL/hour) then HTSfn=HTSfp 36. If (Ya≥OsmS1) and (Ya<OsmS1+((OsmSh−OsmS1)/3)) and (Ya−Yb≥2 mOsm/Kg) and (HTSfp>0 mL/hour) then HTSfn=HTSfp 37. If (Ya≥OsmS1+((OsmSh−OsmS1)/3)) and (Ya<OsmS1+(2(OsmSh−OsmS1)/3)) and (Ya−Yb<−2 mOsm/Kg) and (HTSfp=0 mL/hour) then HTSfn=(0.07*Wt*3/Z) mL/hour 38. If (Ya≥OsmS1+((OsmSh−OsmS1)/3)) and (Ya<OsmS1+(2(OsmSh−OsmS1)/3)) and (Ya−Yb<−2 mOsm/Kg) and (HTSfp>0 mL/hour) and (HTSfp≥(0.2*Wt*3/Z) mL/hour) then HTSfn=(HTSfp*1.2)

39. If (Ya≥OsmS1+((OsmSh−OsmS1)/3)) and (Ya<OsmS1+(2(OsmSh−OsmS1)/3)) and (Ya−Yb<−2 mOsm/Kg) and (HTSfp>(0.2*Wt*3/Z) mL/hour) and (HTSfp≤(0.6*Wt*3/Z) mL/hour) then HTSfn=(HTSfp*1.05)

40. If (Ya≥OsmS1+((OsmSh−OsmS1)/3)) and (Ya<OsmS1+(2(OsmSh−OsmS1)/3)) and (Ya−Yb<−2 mOsm/Kg) and (HTSfp>(0.6*Wt*3/Z) mL/hour) and (HTSfp≤(1*Wt*3/Z) mL/hour) then HTSfn=(HTSfp*1.03)

41. If (Ya≥OsmS1+((OsmSh−OsmS1)/3)) and (Ya<OsmS1+(2(OsmSh−OsmS1)/3)) and (Ya−Yb<−2 mOsm/Kg) and (HTSfp>(1*Wt*3/Z) mL/hour) then HTSfn=(HTSfp*1.02)

42. If (Ya≥OsmS1+((OsmSh−OsmS1)/3)) and (Ya<OsmS1+(2(OsmSh−OsmS1)/3)) and (Ya−Yb≥−2 mOsm/Kg) and (Ya−Yb<2 mOsm/Kg) and (HTSfp=0 mL/hour) then HTSfn=(0.04*Wt*3/Z) mL/hour 43. If (Ya≥OsmS1+((OsmSh−OsmS1)/3)) and (Ya<OsmS1+(2(OsmSh−OsmS1)/3)) and (Ya−Yb≥−2 mOsm/Kg) and (Ya−Yb<2 mOsm/Kg) and (HTSfp>0 mL/hour) and (HTSfp≥(0.2*Wt*3/Z) mL/hour) then HTSfn=(HTSfp*1.1)

44. If (Ya≥OsmS1+((OsmSh−OsmS1)/3)) and (Ya<OsmS1+(2(OsmSh−OsmS1)/3)) and (Ya−Yb≥−2 mOsm/Kg) and (Ya−Yb<2 mOsm/Kg) and (HTSfp>(0.2*Wt*3/Z) mL/hour) and (HTSfp≥(0.6*Wt*3/Z) mL/hour) then HTSfn=(HTSfp*1.03)

45. If (Ya>OsmS1+((OsmSh−OsmS1)/3)) and (Ya<OsmS1+(2(OsmSh−OsmS1)/3)) and (Ya−Yb≥−2 mOsm/Kg) and (Ya−Yb<2 mOsm/Kg) and (HTSfp>(0.6*Wt*3/Z) mL/hour) and (HTSfp≤(1*Wt*3/Z) mL/hour) then HTSfn=(HTSfp*1.02)

46. If (Ya≥OsmS1+((OsmSh−OsmS1)/3)) and (Ya<OsmS1+(2 (OsmSh−OsmS1)/3)) and (Ya−Yb≥−2 mOsm/Kg) and (Ya−Yb<2 mOsm/Kg) and (HTSfp>(1*Wt*3/Z) mL/hour) then HTSfn=(HTSfp*1.01)

47. If (Ya≥OsmS1+((OsmSh−OsmS1)/3)) and (Ya<OsmS1+(2(OsmSh−OsmS1)/3)) and (Ya−Yb≥2 mOsm/Kg) and (HTSfp=0 mL/hour) then HTSfn=HTSfp 48. If (Ya≥OsmS1+((OsmSh−OsmS1)/3)) and (Ya<OsmS1+(2(OsmSh−OsmS1)/3)) and (Ya−Yb≥2 mOsm/Kg) and (HTSfp>0 mL/hour) and (HTSfp≤(0.2*Wt*3/Z) mL/hour) then HTSfn=(HTSfp*0.8)

49. If (Ya≥OsmS1+((OsmSh−OsmS1)/3)) and (Ya<OsmS1+(2(OsmSh−OsmS1)/3)) and (Ya−Yb≥2 mOsm/Kg) and (HTSfp>(0.2*Wt*3/Z) mL/hour) and (HTSfp≤(0.6*Wt*3/Z) mL/hour) then HTSfn=(HTSfp*0.95)

50. If (Ya≥OsmS1+((OsmSh−OsmS1)/3)) and (Ya<OsmS1+(2(OsmSh−OsmS1)/3)) and (Ya−Yb≥2 mOsm/Kg) and (HTSfp>(0.6*Wt*3/Z) mL/hour) and (HTSfp<(1*Wt*3/Z) mL/hour) then HTSfn=(HTSfp*0.97)

51. If (Ya≥OsmS1+((OsmSh−OsmS1)/3)) and (Ya<OsmS1+(2(OsmSh−OsmS1)/3)) and (Ya−Yb≥2 mOsm/Kg) and (HTSfp>(1*Wt*3/Z) mL/hour) then HTSfn=(HTSfp*0.98)

52. If (Ya≥OsmS1+(2(OsmSh−OsmS1)/3)) and (Ya<OsmSh) and (Ya−Yb<−2 mOsm/Kg) and (HTSfp=0 mL/hour) then HTSfn=(0.05*Wt*3/Z) mL/hour 53. If (Ya≥OsmS1+(2(Osmsh−OsmS1)/3)) and (Ya<OsmSh) and (Ya−Yb<−2 mOsm/Kg) and (HTSfp>0 mL/hour) and (HTSfp<(0.2*Wt*3/Z) mL/hour) then HTSfn=(HTSfp*1.15)

54. If (Ya≥OsmS1+(2(OsmSh−OsmS1)/3)) and (Ya<OsmSh) and (Ya−Yb<−2 mOsm/Kg) and (HTSfp>(0.2*Wt*3/Z) mL/hour) and (HTSfp<(0.6*Wt*3/Z) mL/hour) then HTSfn=(HTSfp*1.04)

55. If (Ya>OsmS1+(2(OsmSh−OsmS1)/3)) and (Ya<OsmSh) and (Ya−Yb<−2 mOsm/Kg) and (HTSfp>(0.6*Wt*3/Z) mL/hour) and (HTSfp≤(1*Wt*3/Z) mL/hour) then HTSfn=(HTSfp*1.02)

56. If (Ya≥OsmS1+(2(OsmSh−OsmS1)/3)) and (Ya<OsmSh) and (Ya−Yb<−2 mOsm/Kg) and (HTSfp>(1*Wt*3/Z) mL/hour) then HTSfn=(HTSfp*1.02)

57. If (Ya≥OsmS1+(2(OsmSh−OsmS1)/3)) and (Ya<OsmSh) and (Ya−Yb≥−2 mOsm/Kg) and (Ya−Yb<2 mOsm/Kg) then HTSfn=HTSfp 58. If (Ya≥OsmS1+(2(OsmSh−OsmS1)/3)) and (Ya<OsmSh) and (Ya−Yb≥2 mOsm/Kg) and (HTSfp=0 mL/hour) then HTSfn=HTSfp 59. If (Ya≥OsmS1+(2(OsmSh−OsmS1)/3)) and (Ya<OsmSh) and (Ya−Yb≥2 mOsm/Kg) and (HTSfp>0 mL/hour) and (HTSfp≥(0.2*Wt*3/Z) mL/hour) then HTSfn=(HTSfp*0.7)

60. If (Ya≥OsmS1+(2(OsmSh−OsmS1)/3)) and (Ya<OsmSh) and (Ya−Yb≥2 mOsm/Kg) and (HTSfp>(0.2*Wt*3/Z) mL/hour) and (HTSfp≤(0.6*Wt*3/Z) mL/hour) then HTSfn=(HTSfp*0.92)

61. If (Ya≥OsmS1+(2(OsmSh−OsmS1)/3)) and (Ya<OsmSh) and (Ya−Yb≥2 mOsm/Kg) and (HTSfp>(0.6*Wt*3/Z) mL/hour) and (HTSfp≤(1*Wt*3/Z) mL/hour) then HTSfn=(HTSfp*0.96)

62. If (Ya≥OsmS1+(2(OsmSh−OsmS1)/3)) and (Ya<OsmSh) and (Ya−Yb≥2 mOsm/Kg) and (HTSfp>(1*Wt*3/Z) mL/hour) then HTSfn=(HTSfp*0.97)

63. If (Ya≥OsmSh) and (Ya<OsmSh+5 mOsm/Kg) and (Ya−Yb<−2 mOsm/Kg) then HTSfn=HTSfp 64. If (Ya≥OsmSh) and (Ya<OsmSh+5 mOsm/Kg) and (Ya−Yb≥−2 mOsm/Kg) and (Ya−Yb<2 mOsm/Kg) and (HTSfp=0 mL/hour) then HTSfn=HTSfp 65. If (Ya≥OsmSh) and (Ya<OsmSh+5 mOsm/Kg) and (Ya−Yb≥−2 mOsm/Kg) and (Ya−Yb<2 mOsm/Kg) and (HTSfp>0 mL/hour) and (HTSfp≤(0.2*Wt*3/Z) mL/hour) then HTSfn=(HTSfp*0.85)

66. If (Ya≥OsmSh) and (Ya<OsmSh+5 mOsm/Kg) and (Ya−Yb≥−2 mOsm/Kg) and (Ya−Yb<2 mOsm/Kg) and (HTSfp>(0.2*Wt*3/Z) mL/hour) and (HTSfp≤(0.6*Wt*3/Z) mL/hour) then HTSfn=(HTSfp*0.96)

67. If (Ya≥OsmSh) and (Ya<OsmSh+5 mOsm/Kg) and (Ya−Yb≥−2 mOsm/Kg) and (Ya−Yb<2 mOsm/Kg) and (HTSfp>(0.6*Wt*3/Z) mL/hour) and (HTSfp<(1*Wt*3/Z) mL/hour) then HTSfn=(HTSfp*0.98)

68. If (Ya≥OsmSh) and (Ya<OsmSh+5 mOsm/Kg) and (Ya−Yb≥−2 mOsm/Kg) and (Ya−Yb<2 mOsm/Kg) and (HTSfp>(1*Wt*3/Z) mL/hour) then HTSfn=(HTSfp*0.98)

69. If (Ya≥OsmSh) and (Ya<OsmSh+5 mOsm/Kg) and (Ya−Yb≥2 mOsm/Kg) and (HTSfp=0 mL/hour) then HTSfn=HTSfp 70. If (Ya≥OsmSh) and (Ya<OsmSh+5 mOsm/Kg) and (Ya−Yb≥2 mOsm/Kg) and (HTSfp>0 mL/hour) and (HTSfp≤(0.2*Wt*3/Z) mL/hour) then HTSfn=(HTSfp*0.6)

71. If (Ya≥OsmSh) and (Ya<OsmSh+5 mOsm/Kg) and (Ya−Yb≥2 mOsm/Kg) and (HTSfp>(0.2*Wt*3/Z) mL/hour) and (HTSfp≤(0.6*Wt*3/Z) mL/hour) then HTSfn=(HTSfp*0.9)

72. If (Ya≥OsmSh) and (Ya<OsmSh+5 mOsm/Kg) and (Ya−Yb≥2 mOsm/Kg) and (HTSfp>(0.6*Wt*3/Z) mL/hour) and (HTSfp≤(1*Wt*3/Z) mL/hour) then HTSfn=(HTSfp*0.95)

73. If (Ya≥OsmSh) and (Ya<OsmSh+5 mOsm/Kg) and (Ya−Yb≥2 mOsm/Kg) and (HTSfp>(1*Wt*3/Z) mL/hour) then HTSfn=(HTSfp*0.96)

74. If (Ya≥OsmSh+5 mOsm/Kg) and (Ya−Yb<−2 mOsm/Kg) and (HTSfp=0 mL/hour) then HTSfn=HTSfp 75. If (Ya≥OsmSh+5 mOsm/Kg) and (Ya−Yb<−2 mOsm/Kg) and (HTSfp>0 mL/hour) then HTSfn=HTSfp 76. If (Ya≥OsmSh+5 mOsm/Kg) and (Ya−Yb≥−2 mOsm/Kg) and (Ya−Yb<2 mOsm/Kg) and (HTSfp=0 mL/hour) then HTSfn=HTSfp 77. If (Ya≥OsmSh+5 mOsm/Kg) and (Ya−Yb≥−2 mOsm/Kg) and (Ya−Yb<2 mOsm/Kg) and (HTSfp>0 mL/hour) and (HTSfp≥(0.2*Wt*3/Z) mL/hour) then HTSfn=(HTSfp*0.86)

78. If (Ya≥OsmSh+5 mOsm/Kg) and (Ya−Yb≥−2 mOsm/Kg) and (Ya−Yb<2 mOsm/Kg) and (HTSfp>(0:2*Wt*3/Z) mL/hour) and (HTSfp≤(0.6*Wt*3/Z) mL/hour) then HTSfn=(HTSfp*0.97)

79. If (Ya≥OsmSh+5 mOsm/Kg) and (Ya−Yb≤−2 mOsm/Kg) and (Ya−Yb<2 mOsm/Kg) and (HTSfp>(0.6*Wt*3/Z) mL/hour) and (HTSfp<(1*Wt*3/Z) mL/hour) then HTSfn=(HTSfp*0.99)

80. If (Ya≥OsmSh+5 mOsm/Kg) and (Ya−Yb≤−2 mOsm/Kg) and (Ya−Yb<2 mOsm/Kg) and (HTSfp>(1*Wt*3/Z) mL/hour) then HTSfn=(HTSfp*0.99)

81. If (Ya≥OsmSh+5 mOsm/Kg) and (Ya−Yb≥2 mOsm/Kg) and (HTSfp=0 mL/hour) then HTSfn=HTSfp and activate alarm "High Osmolality, Hypertonic Saline Off, Assess Patient"

82. If (Ya≥OsmSh+5 mOsm/Kg) and (Ya−Yb≤2 mOsm/Kg) and (HTSfp>0 mL/hour) and (HTSfp≤(0.2*Wt*3/Z) mL/hour) then HTSfn=(HTSfp*0.5)

83. If (Ya≥OsmSh+5 mOsm/Kg) and (Ya−Yb≤2 mOsm/Kg) and (HTSfp>(0.2*Wt*3/Z) mL/hour) and (HTSfp≤(0.6*Wt*3/Z) mL/hour) then HTSfn=(HTSfp*0.87)
84. If (Ya≥OsmSh+5 mOsm/Kg) and (Ya−Yb≥2 mOsm/Kg) and (HTSfp>(0.6*Wt*3/Z) mL/hour) and (HTSfp≤(1*Wt*3/Z) mL/hour) then HTSfn=(HTSfp*0.94)
85. If (Ya≥OsmSh+5 mOsm/Kg) and (Ya−Yb≥2 mOsm/Kg) and (HTSfp>(1*Wt*3/Z) mL/hour) then HTSfn=(HTSfp*0.95)
86. If HTSfn<(0.01*Wt*3/Z) then HTSfn=0 mL/hour
87. If HTSfn>HTSSh then HTSfn=HTSSh and activate alarm "Maximum Hypertonic Saline Flow Rate"
88. MIVFR=(TIVFR−HTSfn)

If Glucose algorithm and Osmolality algorithms are run concurrently then eliminate "223" from Glucose algorithm and replace "88" from Osmolality algorithm with:

$$MIVFR = TIVFR - (Dexfn + (INSfn * Conc^{-1}) + HTSfn)$$

Osmolality Algorithm Table

| | Ya (mOsm/Kg) | AND Ya − Yb (mOsm/Kg) | AND HTSfp (mL/hr) | THEN | HTSfn = (mL/hr) |
|---|---|---|---|---|---|
| 1 | Ya − OsmSl < −5 | Ya − Yb < −2 | HTSfp = 0 | | 0.2 * Wt * 3/Z |
| 2 | Ya − OsmSl < −5 | Ya − Yb < −2 | 0 < HTSfp ≤ 0.2 * Wt * 3/Z | | HTSfp * 1.4 |
| 3 | Ya − OsmSl < −5 | Ya − Yb < −2 | 0.2 * Wt * 3/Z < HTSfp ≤ 0.6 * Wt * 3/Z | | HTSfp * 1.1 |
| 4 | Ya − OsmSl < −5 | Ya − Yb < −2 | 0.6 * Wt * 3/Z < HTSfp ≤ 1* Wt * 3/Z | | HTSfp * 1.05 |
| 5 | Ya − OsmSl < −5 | Ya − Yb < −2 | 1 * Wt * 3/Z < HTSfp | | HTSfp * 1.04 |
| 6 | Ya − OsmSl < −5 | −2 ≤ Ya − Yb < 2 | HTSfp = 0 | | 0.12 * Wt * 3/Z |
| 7 | Ya − OsmSl < −5 | −2 ≤ Ya − Yb < 2 | 0 < HTSfp ≤ 0.2 * Wt * 3/Z | | HTSfp * 1.25 |
| 8 | Ya − OsmSl < −5 | −2 ≤ Ya − Yb < 2 | 0.2 * Wt * 3/Z < HTSfp ≤ 0.6 * Wt * 3/Z | | HTSfp * 1.07 |
| 9 | Ya − OsmSl < −5 | −2 ≤ Ya − Yb < 2 | 0.6 * Wt * 3/Z < HTSfp ≤ 1* Wt * 3/Z | | HTSfp * 1.04 |
| 10 | Ya − OsmSl < −5 | −2 ≤ Ya − Yb < 2 | 1* Wt * 3/Z < HTSfp | | HTSfp * 1.03 |
| 11 | Ya − OsmSl < −5 | 2 ≤ Ya − Yb | HTSfp = 0 | | 0.08 * Wt * 3/Z |
| 12 | Ya − OsmSl < −5 | 2 ≤ Ya − Yb | 0 < HTSfp | | HTSfp |
| 13 | −5 ≤ Ya − OsmSl < 0 | Ya − Yb < −2 | HTSfp = 0 | | 0.15 * Wt * 3/Z |
| 14 | −5 ≤ Ya − OsmSl < 0 | Ya − Yb < −2 | 0 < HTSfp ≤ 0.2 * Wt * 3/Z | | HTSfp * 1.3 |
| 15 | −5 ≤ Ya − OsmSl < 0 | Ya − Yb < −2 | 0.2 * Wt * 3/Z < HTSfp ≤ 0.6 * Wt * 3/Z | | HTSfp * 1.07 |
| 16 | −5 ≤ Ya − OsmSl < 0 | Ya − Yb < −2 | 0.6 * Wt * 3/Z < HTSfp ≤ 1* Wt * 3/Z | | HTSfp * 1.04 |
| 17 | −5 ≤ Ya − OsmSl < 0 | Ya − Yb < −2 | 1 * Wt * 3/Z < HTSfp | | HTSfp * 1.03 |
| 18 | −5 ≤ Ya − OsmSl < 0 | −2 ≤ Ya − Yb < 2 | HTSfp = 0 | | 0.08 * Wt * 3/Z |
| 19 | −5 ≤ Ya − OsmSl < 0 | −2 ≤ Ya − Yb < 2 | 0 < HTSfp ≤ 0.2 * Wt * 3/Z | | HTSfp * 1.2 |
| 20 | −5 ≤ Ya − OsmSl < 0 | −2 ≤ Ya − Yb < 2 | 0.2 * Wt * 3/Z < HTSfp ≤ 0.6 * Wt * 3/Z | | HTSfp * 1.05 |
| 21 | −5 ≤ Ya − OsmSl < 0 | −2 ≤ Ya − Yb < 2 | 0.6 * Wt * 3/Z < HTSfp ≤ 1* Wt * 3/Z | | HTSfp * 1.03 |
| 22 | −5 ≤ Ya − OsmSl < 0 | −2 ≤ Ya − Yb < 2 | 1 * Wt * 3/Z < HTSfp | | HTSfp * 1.02 |
| 23 | −5 ≤ Ya − OsmSl < 0 | 2 ≤ Ya − Yb | HTSfp = 0 | | HTSfp |
| 24 | −5 ≤ Ya − OsmSl < 0 | 2 ≤ Ya − Yb | 0 < HTSfp | | HTSfp |
| 25 | 0 ≤ Ya − OsmSl < (OsmSh − OsmSl)/3 | Ya − Yb < −2 | HTSfp = 0 | | 0.1 * Wt * 3/Z |
| 26 | 0 ≤ Ya − OsmSl < (OsmSh − OsmSl)/3 | Ya − Yb < −2 | 0 < HTSfp ≤ 0.2 * Wt * 3/Z | | HTSfp * 1.24 |
| 27 | 0 ≤ Ya − OsmSl < (OsmSh − OsmSl)/3 | Ya − Yb < −2 | 0.2 * Wt * 3/Z < HTSfp ≤ 0.6 * Wt * 3/Z | | HTSfp * 1.06 |
| 28 | 0 ≤ Ya − OsmSl < (OsmSh − OsmSl)/3 | Ya − Yb < −2 | 0.6 * Wt * 3/Z < HTSfp ≤ 1* Wt * 3/Z | | HTSfp * 1.03 |
| 29 | 0 ≤ Ya − OsmSl < (OsmSh − OsmSl)/3 | Ya − Yb < −2 | 1 * Wt * 3/Z < HTSfp | | HTSfp * 1.02 |
| 30 | 0 ≤ Ya − OsmSl < (OsmSh − OsmSl)/3 | −2 ≤ Ya − Yb < 2 | HTSfp = 0 | | 0.006 * Wt * 3/Z |
| 31 | 0 ≤ Ya − OsmSl < (OsmSh − OsmSl)/3 | −2 ≤ Ya − Yb < 2 | 0 < HTSfp ≤ 0.2 * Wt * 3/Z | | HTSfp * 1.15 |
| 32 | 0 ≤ Ya − OsmSl < (OsmSh − OsmSl)/3 | −2 ≤ Ya − Yb < 2 | 0.2 * Wt * 3/Z < HTSfp ≤ 0.6 * Wt * 3/Z | | HTSfp * 1.04 |
| 33 | 0 ≤ Ya − OsmSl < (OsmSh − OsmSl)/3 | −2 ≤ Ya − Yb < 2 | 0.6 * Wt * 3/Z < HTSfp ≤ 1* Wt * 3/Z | | HTSfp * 1.02 |
| 34 | 0 ≤ Ya − OsmSl < (OsmSh − OsmSl)/3 | −2 ≤ Ya − Yb < 2 | 1 * Wt * 3/Z < HTSfp | | HTSfp * 1.02 |
| 35 | 0 ≤ Ya − OsmSl < (OsmSh − OsmSl)/3 | 2 ≤ Ya − Yb | HTSfp = 0 | | HTSfp |
| 36 | 0 ≤ Ya − OsmSl < (OsmSh − OsmSl)/3 | 2 ≤ Ya − Yb | 0 < HTSfp | | HTSfp |
| 37 | (OsmSh − OsmSl)/3 ≤ Ya − OsmSl < 2(OsmSh − OsmSl)/3 | Ya − Yb < −2 | HTSfp = 0 | | 0.07 * Wt * 3/Z |
| 38 | (OsmSh − OsmSl)/3 ≤ Ya − OsmSl < 2(OsmSh − OsmSl)/3 | Ya − Yb < −2 | 0 < HTSfp ≤ 0.2 * Wt * 3/Z | | HTSfp * 1.2 |
| 39 | (OsmSh − OsmSl)/3 ≤ Ya − OsmSl < 2(OsmSh − OsmSl)/3 | Ya − Yb < −2 | 0.2 * Wt * 3/Z < HTSfp ≤ 0.6 * Wt * 3/Z | | HTSfp * 1.05 |
| 40 | (OsmSh − OsmSl)/3 ≤ Ya − OsmSl < 2(OsmSh − OsmSl)/3 | Ya − Yb < −2 | 0.6 * Wt * 3/Z < HTSfp ≤ 1* Wt * 3/Z | | HTSfp * 1.03 |
| 41 | (OsmSh − OsmSl)/3 ≤ Ya − OsmSl < 2(OsmSh − OsmSl)/3 | Ya − Yb < −2 | 1 * Wt * 3/Z < HTSfp | | HTSfp * 1.02 |
| 42 | (OsmSh − OsmSl)/3 ≤ Ya − OsmSl < 2(OsmSh − OsmSl)/3 | −2 ≤ Ya − Yb < 2 | HTSpf = 0 | | 0.05 * Wt *3/Z |
| 43 | (OsmSh − OsmSl)/3 ≤ Ya − OsmSl < 2(OsmSh − OsmSl)/3 | −2 ≤ Ya − Yb < 2 | 0 < HTSfp ≤ 0.2 * Wt * 3/Z | | HTSfp * 1.1 |
| 44 | (OsmSh − OsmSl)/3 ≤ Ya − OsmSl < 2(OsmSh − OsmSl)/3 | −2 ≤ Ya − Yb < 2 | 0.2 * Wt * 3/Z < HTSfp ≤ 0.6 * Wt * 3/Z | | HTSfp * 1.03 |
| 45 | (OsmSh − OsmSl)/3 ≤ Ya − OsmSl < 2(OsmSh − OsmSl)/3 | −2 ≤ Ya − Yb < 2 | 0.6 * Wt * 3/Z < HTSfp ≤ 1* Wt * 3/Z | | HTSfp * 1.02 |
| 46 | (OsmSh − OsmSl)/3 ≤ Ya − OsmSl < 2(OsmSh − OsmSl)/3 | −2 ≤ Ya − Yb < 2 | 1 * Wt * 3/Z < HTSfp | | HTSfp * 1.01 |
| 47 | (OsmSh − OsmSl)/3 ≤ Ya − OsmSl < 2(OsmSh − OsmSl)/3 | 2 ≤ Ya − Yb | HTSfp = 0 | | HTSfp |
| 48 | (OsmSh − OsmSl)/3 ≤ Ya − OsmSl < 2(OsmSh − OsmSl)/3 | 2 ≤ Ya − Yb | 0 < HTSfp ≤ 0.2 * Wt * 3/Z | | HTSfp * 0.08 |

-continued

Osmolality Algorithm Table

| | Ya (mOsm/Kg) | AND Ya − Yb (mOsm/Kg) | AND HTSfp (mL/hr) | THEN | HTSfn = (mL/hr) |
|---|---|---|---|---|---|
| 49 | (OsmSh − OsmSl)/3 ≤ Ya − OsmSl < (OsmSh − OsmSl)/3 | 2 ≤ Ya − Yb | 0.2 * Wt * 3/Z < HTSfp ≤ 0.6 * Wt * 3/Z | | HTSfp * 0.95 |
| 50 | (OsmSh − OsmSl)/3 ≤ Ya − OsmSl < 2 (OsmSh − OsmSl)/3 | 2 ≤ Ya − Yb | 0.6 * Wt * 3/Z < HTSfp ≤ 1* Wt * 3/Z | | HTSfp * 0.97 |
| 51 | (OsmSh − OsmSl)/3 ≤ Ya − OsmSl < 2 (OsmSh − OsmSl)/3 | 2 ≤ Ya − Yb | 1 * Wt * 3/Z < HTSfp | | HTSfp * 0.98 |
| 52 | 2(OsmSh − OsmSl)/3 ≤ Ya − OsmSl < OsmSh − OsmSl | Ya − Yb < −2 | HTSfp = 0 | | 0.05 * Wt * 3/Z |
| 53 | 2(OsmSh − OsmSl)/3 ≤ Ya − OsmSl < OsmSh − OsmSl | Ya − Yb < −2 | 0 < HTSfp ≤ 0.2 * Wt * 3/Z | | HTSfp * 1.15 |
| 54 | 2(OsmSh − OsmSl)/3 ≤ Ya − OsmSl < OsmSh − OsmSl | Ya − Yb < −2 | 0.2 * Wt * 3/Z < HTSfp ≤ 0.6 * Wt * 3/Z | | HTSfp * 1.04 |
| 55 | 2(OsmSh − OsmSl)/3 ≤ Ya − OsmSl < OsmSh − OsmSl | Ya − Yb < −2 | 0.6 * Wt * 3/Z < HTSfp ≤ 1 * Wt * 3/Z | | HTSfp * 1.02 |
| 56 | 2(OsmSh − OsmSl)/3 ≤ Ya − OsmSl < OsmSh − OsmSl | Ya − Yb < −2 | 1 * Wt * 3/Z < HTSfp | | HTSfp * 1.02 |
| 57 | 2(OsmSh − OsmSl)/3 ≤ Ya − OsmSl < OsmSh − OsmSl | −2 ≤ Ya − Yb < 2 | — | | HTSfp |
| 58 | 2(OsmSh − OsmSl)/3 ≤ Ya − OsmSl < OsmSh − OsmSl | 2 ≤ Ya − Yb | HTSfp = 0 | | HTSfp |
| 59 | 2(OsmSh − OsmSl)/3 ≤ Ya − OsmSl < OsmSh − OsmSl | 2 ≤ Ya − Yb | 0 < HTSfp ≤ 0.2 * Wt * 3/Z | | HTSfp * 0.7 |
| 60 | 2(OsmSh − OsmSl)/3 ≤ Ya − OsmSl < OsmSh − OsmSl | 2 ≤ Ya − Yb | 0.2 * Wt * 3/Z < HTSfp ≤ 0.6 * Wt * 3/Z | | HTSfp * 0.92 |
| 61 | 2(OsmSh − OsmSl)/3 ≤ Ya − OsmSl < OsmSh − OsmSl | 2 ≤ Ya − Yb | 0.6 * Wt * 3/Z < HTSfp ≤ 1 * Wt * 3/Z | | HTSfp * 0.96 |
| 62 | 2(OsmSh − OsmSl)/3 ≤ Ya − OsmSl < OsmSh − OsmSl | 2 ≤ Ya − Yb | 1 * Wt * 3/Z < HTSfp | | HTSfp * 0.97 |
| 63 | (OsmSh − OsmSl) ≤ Ya − OsmSl < (OsmSh − OsmSl) + 5 | Ya − Yb < −2 | — | | HTSfp |
| 64 | (OsmSh − OsmSl) ≤ Ya − OsmSl < (OsmSh − OsmSl) + 5 | −2 ≤ Ya − Yb < 2 | HTSfp = 0 | | HTSfp |
| 65 | (OsmSh − OsmSl) ≤ Ya − OsmSl < (OsmSh − OsmSl) + 5 | −2 ≤ Ya − Yb < 2 | 0 < HTSfp ≤ 0.2 * Wt * 3/Z | | HTSfp * 0.85 |
| 66 | (OsmSh − OsmSl) ≤ Ya − OsmSl < (OsmSh − OsmSl) + 5 | −2 ≤ Ya − Yb < 2 | 0.2 * Wt * 3/Z < HTSfp ≤ 0.6 * Wt * 3/Z | | HTSfp * 0.96 |
| 67 | (OsmSh − OsmSl) ≤ Ya − OsmSl < (OsmSh − OsmSl) + 5 | −2 ≤ Ya − Yb < 2 | 0.6 * Wt * 3/Z < HTSfp ≤ 1* Wt * 3/Z | | HTSfp * 0.98 |
| 68 | (OsmSh − OsmSl) ≤ Ya − OsmSl < (OsmSh − OsmSl) + 5 | −2 ≤ Ya − Yb < 2 | 1 * Wt * 3/Z < HTSfp | | HTSfp * 0.98 |
| 69 | (OsmSh − OsmSl) ≤ Ya − OsmSl < (OsmSh − OsmSl) + 5 | 2 ≤ Ya − Yb | HTSfp = 0 | | HTSfp |
| 70 | (OsmSh − OsmSl) ≤ Ya − OsmSl < (OsmSh − OsmSl) + 5 | 2 ≤ Ya − Yb | 0 < HTSfp ≤ 0.2 * Wt * 3/Z | | HTSfp * 0.6 |
| 71 | (OsmSh − OsmSl) ≤ Ya − OsmSl < (OsmSh − OsmSl) + 5 | 2 ≤ Ya − Yb | 0.2 * Wt * 3/Z < HTSfp ≤ 0.6 * Wt * 3/Z | | HTSfp * 0.9 |
| 72 | (OsmSh − OsmSl) ≤ Ya − OsmSl < (OsmSh − OsmSl) + 5 | 2 ≤ Ya − Yb | 0.6 * Wt * 3/Z < HTSfp ≤ 1 * Wt * 3/Z | | HTSfp * 0.95 |
| 73 | (OsmSh − OsmSl) ≤ Ya − OsmSl < (OsmSh − OsmSl) + 5 | 2 ≤ Ya − Yb | 1 * Wt * 3/Z < HTSfp | | HTSfp * 0.96 |
| 74 | (OsmSh − OsmSl) + 5 ≤ Ya − OsmSl | Ya − Yb < −2 | HTSfp = 0 | | HTSfp |
| 75 | (OsmSh − OsmSl) + 5 ≤ Ya − OsmSl | Ya − Yb < −2 | HTSfp > 0 | | HTSfp |
| 76 | (OsmSh − OsmSl) + 5 ≤ Ya − OsmSl | −2 ≤ Ya − Yb < 2 | HTSfp = 0 | | HTSfp |
| 77 | (OsmSh − OsmSl) + 5 ≤ Ya − OsmSl | −2 ≤ Ya − Yb < 2 | 0 < HTSfp ≤ 0.2 * Wt * 3/Z | | HTSft * 0.86 |
| 78 | (OsmSh − OsmSl) + 5 ≤ Ya − OsmSl | −2 ≤ Ya − Yb < 2 | 0.2 * Wt * 3/Z < HTSfp ≤ 0.6 * Wt * 3/Z | | HTSfp * 0.97 |
| 79 | (OsmSh − OsmSl) + 5 ≤ Ya − OsmSl | −2 ≤ Ya − Yb < 2 | 0.6 * Wt * 3/Z < HTSfp ≤ 1* Wt * 3/Z | | HTSfp * 0.99 |
| 80 | (OsmSh − OsmSl) + 5 ≤ Ya − OsmSl | −2 ≤ Ya − Yb < 2 | 1 * Wt * 3/Z < HTSfp | | HTSfp * 0.99 |
| 81 | (OsmSh − OsmSl) + 5 ≤ Ya − OsmSl | 2 ≤ Ya − Yb | HTSfp = 0 | | HTSfp ALARM |
| 82 | (OsmSh − OsmSl) + 5 ≤ Ya − OsmSl | 2 ≤ Ya − Yb | 0 < HTSfp ≤ 0.2 * Wt * 3/Z | | HTSfp * 0.5 |
| 83 | (OsmSh − OsmSl) + 5 ≤ Ya − OsmSl | 2 ≤ Ya − Yb | 0.2 * Wt * 3/Z < HTSfp ≤ 0.6 * Wt * 3/Z | | HTSfp * 0.87 |
| 84 | (OsmSh − OsmSl) + 5 ≤ Ya − OsmSl | 2 ≤ Ya − Yb | 0.6 * Wt * 3/Z < HTSfp ≤ 1 * Wt * 3/Z | | HTSfp * 0.94 |
| 85 | (OsmSh − OsmSl) + 5 ≤ Ya − OsmSl | 2 ≤ Ya − Yb | 1 * Wt * 3/Z < HTSfp | | HTSfp * 0.95 |
| 86 | If HTSfn < (0.01 * Wt * 3/Z) then HTSfn = 0 mL/hour | | | | |
| 87 | If HTSfn > HTSSh then HTSfn = HTSSh and activate Alarm "Maximum Hypertonic Saline Flow Rate" | | | | |
| 88 | MIVFR = (TIVFR − HTSfn) | | | | |

If Glucose algorithm and Osmolality algorithm are run concurrently then eliminate "223" from Glucose algorithm and replace "88" from Osmolality algorithm with: MIVFR = TIVFR − (Dexfn + (INSfn * Conc − 1) + HTSfn)

Rules for Secondary Controller
1. If (Xmin≥80 mg/dL) and (Xa<Xmin) and (Xa−Xb≤−6 mg/dL) then INSfn$_{2c}$=(INSfn*0.75)
2. If (Xa<Xmin) and (Xa−Xb≤−6 mg/dL) and (Dexfp>0 mL/hour) then Dexfn$_{2c}$=(Dexfn*1.2)
3. If (Xa<60 mg/dL) and (INSfn>0 units/hour) then INSfn$_{2c}$=0 units/hour
4. If (Xa>60 mg/dL) and (Xa<70 mg/dL) and (Xa−Xb≥−10 mg/dL) and (Xa−Xb<−5 mg/dL) and (INSfn>0 units/hour) then INSfn$_{2c}$=(INSfn*0.8)
5. If (Xa≥60 mg/dL) and (Xa<70 mg/dL) and (Xa−Xb<−10 mg/dL) and (INSfn>0 units/hour) then INSfn$_{2c}$=0 units/hour
6. If (Xa≥Xmin) and (Xa<Xmax) and (Xa−Xb≤−8 mg/dL) then INSfn$_{2c}$=(INSfn*0.8)
7. If (Xa≥Xmin) and (Xa<Xmax) and (Xa−Xb≥10 mg/dL) and (Xa−Xb<15 mg/dL) then INSfn$_{2c}$=(INSfn*1.1)
8. If (Xa≥Xmin) and (Xa<Xmax) and (Xa−Xb≥15 mg/dL) then INSfn$_{2c}$=(INSfn*1.2)
9. If (Xa<100 mg/dL) and (Xa−Xb<−12 mg/dL) and (Dexfn=0 mL/hour) then Dexfn$_{2c}$=(2/C*Wt) mL/hour
10. If (Xa≥Xmin) and (Xa<Xmax) and (Xa−Xb<−12 mg/dL) and (Dexfn>0 mL/hour) then Dexfn$_{2c}$=(Dexfn*1.2)
11. If (Xa≥Xmin) and (Xa−Xb>10 mg/dL) and (Dexfn>0 mL/hour) then Dexfn$_{2c}$=(Dexfn*0.8)
12. If (Xa≥Xmax) and (Xa<Xmax+30 mg/dL) and (Xa−Xb≥−20 mg/dL) and (Xa−Xb<−10 mg/dL) and (no bolus given) then INSfn$_{2c}$=(INSfn*0.75)
13. If (Xa≥Xmax) and (Xa<(Xmax+30 mg/dL)) and (Xa−Xb<−20 mg/dL) and (Xa−Xc<−30 mg/dL) then INSfn$_{2c}$=(INSfn*0.65)
14. If (Xa≥Xmax) and (Xa−Xb>10 mg/dL) and (INSfn<(0.08*Wt) units/hour) then INSfn$_{2c}$=(INSfn*1.3)
15. If (Xa≥Xmax) and (Xa−Xb>10 mg/dL) and (INSfn>(0.08*Wt) units/hour) then INSfn$_{2c}$=(INSfn*1.1)
16. If (Xa≥(Xmax+30 mg/dL)) and (Xa<(Xmax+60 mg/dL)) and (Xa−Xb<−20 mg/dL) then INSfn$_{2c}$=(INSfp*0.7)
17. If (Xa≥(Xmax+30 mg/dL)) and (Xa<(Xmax+60 mg/dL)) and (Xa−Xb≥−20 mg/dL) and (Xa−Xb<−15 mg/dL) then INSfn$_{2c}$=(INSfn*0.75)
18. If (Xa≥(Xmax+30 mg/dL)) and (Xa≤(Xmax+60 mg/dL)) and (Xa−Xb≥−15 mg/dL) and (Xa−Xb<−10 mg/dL) then INSfn$_{2c}$=INSfp
19. If (Xa≥(Xmax+60 mg/dL)) and (Xa−Xb<−20 mg/dL) and (Xa−Xc<−40 mg/dL) then INSfn$_{2c}$=(INSfn*0.65)
20. If (Xa<Xmin) then change algorithm cycle interval to every 5 minutes
21. If (Xa≥(Xmin) and (Xa<Xmax) and (Xa−Xb≤−10 mg/dL) then change algorithm cycle interval to every 5 minutes
22. If (Xa≥(Xmin) and (Xa<Xmax) and (Xa−Xb≥10 mg/dL) then change algorithm cycle interval to every 5 minutes
23. If (Xa≥Xmax) and (Xa<Xmax+30 mg/dL) and (Xa−Xb<−10 mg/dL) then change cycle interval to every 5 minutes
24. If (Xa≥(Xmax+30 mg/dL)) and (Xa−Xb<−20 mg/dL) then change algorithm cycle interval to every 5 minutes
25. If (Xa≥Xmin) and (Xa<Xmax) and (Xa−Xb≥−10 mg/dL) and (Xa−Xb<10 mg/dL) then cycle interval=every 10 minutes
26. If (Xa≥Xmax) and (Xa<(Xmax+30 mg/dL)) and (Xa−Xb≥−10 mg/dL) then cycle interval=every 10 minutes
27. If (Xa≥(Xmax+30 mg/dL)) and (Xa−Xb≥−20 mg/dL) then cycle interval=every 10 minutes
28. Secondary controller rules modify rules 1-217, but do not modify rules 218-220.

The invention claimed is:

1. A computerized glucose adjustment system for intravenously controlling a patient's blood chemistry on a real time basis, said system comprising:
a glucose sensor measuring a patient's glucose level;
a pump connected to a source of insulin and a source of dextrose for distributing insulin and dextrose into a patient's bloodstream;
a computer processor in electronic communication with said sensor and said pump, said processor receiving an electronic signal from said sensor for calculating the patient's real time average glucose level over a specified time period;
a glucose control module stored in said processor, said glucose control module (i) determining where the patient's real time average blood glucose level lies along a continuum of glucose values; (ii) tracking a rate at which the average blood glucose level is changing over time and (iii) iteratively adjusting the dextrose flow rate and insulin flow rate into the patient's body to adjust the real time average glucose level closer to a known normal glucose range by sending output signals to said pump and controlling a pump rate at which said pump distributes insulin and dextrose into the patient, wherein the real time average blood glucose level calculated in the processor is a running average (Xa) over a specified time period, wherein the computer processor records a prior running average blood glucose level (Xb) for a prior time period previous to a just completed specified time period, wherein the glucose control module compares the running average glucose level (Xa) to the prior running average glucose level (Xb) to track a real time average blood glucose level rate of change, wherein said glucose control module comprises pump controlling commands divided into categories, that determine an extent to which a dextrose flow rate and an insulin flow rate from said pump are adjusted; and
wherein said processor assigns each running average blood glucose level (Xa) to one of said categories by grouping (A) a difference between a most recently calculated running average blood glucose value (Xa) and a range of Xmin to Xmax; (B) said real time average blood glucose level rate of change; (C) a value of a previous weight-based insulin flow rate; and (D) a value of a previous weight-based dextrose flow rate, and wherein said processor groups A, B, C, and D each time a new average glucose level Xa is calculated, and
wherein said glucose control module determines an extent to which a dextrose flow rate and an insulin flow rate from said pump are adjusted by said pump controlling commands in said one of said categories.

2. A computerized glucose adjustment system according to claim 1, further comprising a catheter distributing insulin and dextrose into a patient's bloodstream, wherein said glucose sensor is positioned on said catheter and positioned within the patient's bloodstream.

3. A computerized glucose adjustment system according to claim 1, wherein said glucose sensor is positioned within the patient's subcutaneous tissues.

4. A computerized glucose adjustment system according to claim 1, wherein said glucose sensor is in an extracorporeal position.

5. A computerized glucose adjustment system according to claim 1, wherein said dextrose flow rate is a function of the patient's weight in kilograms.

6. A computerized glucose adjustment system according to claim 1, wherein said insulin flow rate is a function of the patient's weight in kilograms.

7. A computerized glucose adjustment system according to claim 1, wherein said processor accepts as an input an initial concentration of said dextrose.

8. A computerized glucose adjustment system according to claim 1, wherein said processor accepts as an input an initial concentration of said insulin.

9. A computerized glucose adjustment system according to claim 7, wherein said initial concentration of said dextrose is selected from the group consisting of 5, 10, 12.5, 15, 20, and 25 in percent weight per volume.

10. A computerized glucose adjustment system according to claim 1, wherein said glucose control module operates continuously on a real time basis with updated glucose measurements.

11. A computerized glucose adjustment system according to claim 1, wherein a user sets said known normal glucose range between Xmin and Xmax, the system further comprising a "Low Glucose" alarm set point and a "High Glucose" alarm set point both of which are set by medical personnel.

12. A computerized glucose adjustment system according to claim 11, wherein said glucose control module calculates and stores said average blood glucose level Xa in units of milligrams per deciliter over said specified time period.

13. A computerized glucose adjustment system according to claim 12, wherein said glucose control module calculates and stores blood glucose value Xt in milligrams per deciliter every 30 seconds and calculates the average glucose level Xa in milligrams per deciliter over said specified time period equal to 10 minutes.

14. A computerized glucose adjustment system according to claim 13, wherein said pump controlling commands are divided into categories defined by glucose value ranges along a glucose value continuum.

15. A computerized glucose adjustment system, according to claim 14, wherein said pump controlling command category is selected from the group consisting of:
  Category 1: Xa−Xmin<−10 mg/dl;
  Category 2: −10≤Xa−Xmin<−5 mg/dl
  Category 3: −5≤Xa−Xmin<0 mg/dl
  Category 4: 0≤Xa−Xmin<(Xmax−Xmin)/3
  Category 5: Xmax−Xmin)/3≤Xa−Xmin<2(Xmax−Xmin)/3
  Category 6: 2(Xmax−Xmin)/3≤Xa−Xmin<Xmax−Xmin
  Category 7: 0≤Xa−Xmax<10
  Category 8: 10≤Xa−Xmax<30
  Category 9: Xa−Xmax≥30.

16. A computerized glucose adjustment system according to claim 15, wherein said controller calculates the category for the current average glucose measurement Xa.

17. A computerized glucose adjustment system according to claim 16, wherein said controller compares a current glucose measurement Xa to a prior average glucose measurement Xb to determine the rate at which the average glucose level is changing.

18. A computerized glucose adjustment system according to claim 16, wherein said controller compares a current glucose measurement Xa to a prior glucose measurement Xc to determine the rate at which the average glucose level is changing over an extended time period.

19. A computerized glucose adjustment system according to claim 17, wherein said pump controlling commands adjust said pump output to control the flow rates of insulin (INSf) and dextrose (Dexf) according to the category in which the current glucose measurement fits and the rate at which the glucose level is changing.

20. A computerized glucose adjustment system according to claim 16, wherein for each category, the next insulin (INSfn) and next dextrose (Dexfh) flow rates are adjusted for condition Xa−Xb (mg/dl), wherein said condition is selected from the group consisting of Xa−Xb≤−15; −15<Xa−Xb≤3; and Xa−Xb>3.

21. A computerized glucose adjustment system according to claim 20, wherein the value for Xa−Xb is selected from the group consisting of:
  a) Xa−Xb≤−15 mg/dL
  b) Xa−Xb>−15 mg/dL
  c) Xa−Xb≤−6 mg/dL
  d) Xa−Xb>−6 mg/dL
  e) Xa−Xb>−6 and ≤0 mg/dL
  f) Xa−Xb≤−5 mg/dL
  g) Xa−Xb>−5 and ≤0 mg/dL
  h) Xa−Xb≤−4 mg/dL
  i) Xa−Xb>−4 mg/dL and ≤1 mg/dL
  j) Xa−Xb<−3 mg/dL
  k) Xa−Xb≤−3 mg/dL
  l) Xa−Xb≥−3 mg/dL
  m) Xa−Xb>−3 mg/dL
  n) Xa−Xb≥3 mg/dL and ≤1 mg/dL
  o) Xa−Xb>−3 mg/dL and ≤0 mg/dL
  p) Xa−Xb>−3 mg/dL and ≤3 mg/dL
  q) Xa−Xb<−2 mg/dL
  r) Xa−Xb≤−2 mg/dL
  s) Xa−Xb≥−2 mg/dL
  t) Xa−Xb>−2 mg/dL and ≤3 mg/dL
  u) Xa−Xb<−1 mg/dL
  v) Xa−Xb≥−1 mg/dL
  w) Xa−Xb<0 mg/dL
  x) Xa−Xb≤0 mg/dL
  y) Xa−Xb≤0 and >−4 mg/dL
  z) Xa−Xb≥0 mg/dL
  aa) Xa−Xb>0 mg/dL
  bb) Xa−Xb≤1 mg/dL
  cc) Xa−Xb>1 mg/dL
  dd) Xa−Xb≤2 mg/dL
  ee) Xa−Xb>2 mg/dL
  ff) Xa−Xb>3 mg/dL.

22. A computerized glucose adjustment system according to claim 20, wherein said pump controlling commands adjust said next insulin (INSfn) and next dextrose (Dexfn) flow rates as a function of the previous insulin (INSfp) and dextrose (Dexfp) flow rates within said specified time period.

23. A computerized glucose adjustment system according to claim 21, wherein said previous insulin flow rate (INSfp) is selected from the group consisting of:
  (i) INSfp=0 units/hour;
  (ii) INSfp>0 units/hour;
  (iii) 0<INSfp≤(0.01*Wt) units/hour
  (iv) INSfp<(0.05*Wt) units/hour
  (v) 0<INSfp≤(0.02*Wt) units/hour;
  (vi) 0<INSfp≤(0.05*Wt) units/hour
  (vii) 0<INSfp<(0.05*Wt) units/hour
  (viii) 0<INSfp≤(0.1*Wt) units/hour
  (ix) INSfp>(0.01*Wt) units/hour
  (x) (0.01*Wt) units/hour<INSfp≤(0.1*Wt) units/hour;
  (xi) INSfp>(0.02*Wt) units/hour
  (xii) (0.02*Wt) units/hour<INSfp≤(0.1*Wt) units/hour
  (xiii) INSfp>(0.05*Wt) units per hour;
  (xiv) INSfp≥(0.05*Wt) units per hour (xv) $INSfp > (0.1*Wt)$ units/hour, wherein the value of Wt is the patient's weight in kilograms.

24. A computerized glucose adjustment system according to claim 21, wherein the initial concentration of said dextrose solution is C, and said previous dextrose flow rate (DEXfp) is selected from the group consisting of:
  (i) $DEXfp=0$;
  (ii) $DEXfp>0$ mL/hour;
  (iii) $0$ mL/hour $< DEXfp \leq (1/C*Wt)$ mL/hour;
  (iv) $0$ mL/hour $< DEXfp ((2/C)*Wt)$ mL/hour;
  (v) $DEXfp > (1/C*Wt)$ mL/hour;
  (vi) $(1/C*Wt)$ mL/hour $< DEXfp \leq ((6/C)*Wt)$ mL/hour;
  (vii) $((2/C)*Wt)$ mL/hour $< DEXfp \leq ((6/C)*Wt)$ mL/hour;
  (viii) $((2/C)*Wt)$ mL/hour $< DEXfp$
  (ix) $DEXfp > ((6/C)*Wt)$ mL/hour, wherein the value of Wt is the patient's weight in kilograms.

25. A computerized glucose adjustment system according to claim 20, wherein said controller activates an alarm if the differential between Xa and Xb is greater than 25 or less than −25 mg/dL.

26. A computerized glucose adjustment system according to claim 20 further comprising a secondary controller for adjusting the output of said glucose control module by multiplying the next insulin flow rate INSfn by a secondary adjustment factor.

27. A computerized glucose adjustment system according to claim 1, further compromising a secondary controller for adjusting a cycle time for algorithm data collection and for calculating a rate at which the average blood glucose level changes from one specified time period to the next.

\* \* \* \* \*